United States Patent
Krishnan et al.

(10) Patent No.: US 10,818,379 B2
(45) Date of Patent: Oct. 27, 2020

(54) METHODS AND SYSTEMS FOR ANALYTE INFORMATION PROCESSING

(71) Applicant: Biological Dynamics, Inc., San Diego, CA (US)

(72) Inventors: Rajaram Krishnan, San Diego, CA (US); Iryna Clark, Del Mar, CA (US); Robert Turner, San Diego, CA (US); Robert Kovelman, La Jolla, CA (US); Juan Pablo Hinestrosa Salazar, San Diego, CA (US); David Liu, San Diego, CA (US)

(73) Assignee: BIOLOGICAL DYNAMICS, INC., San Diego, CA (US)

( * ) Notice: Subject to any disclaimer, the term of this patent is extended or adjusted under 35 U.S.C. 154(b) by 0 days.

(21) Appl. No.: 15/974,591

(22) Filed: May 8, 2018

(65) Prior Publication Data

US 2018/0322941 A1    Nov. 8, 2018

Related U.S. Application Data

(60) Provisional application No. 62/503,174, filed on May 8, 2017.

(51) Int. Cl.
| | | |
|---|---|---|
| *G16H 10/40* | (2018.01) | |
| *G16H 10/20* | (2018.01) | |
| *G01N 27/447* | (2006.01) | |
| *B01L 3/00* | (2006.01) | |
| *G01N 33/53* | (2006.01) | |
| *G16H 30/20* | (2018.01) | |

(52) U.S. Cl.
CPC ........ *G16H 10/40* (2018.01); *B01L 3/502715* (2013.01); *G01N 27/44791* (2013.01); *G01N 33/53* (2013.01); *G16H 10/20* (2018.01); *G16H 30/20* (2018.01); *B01L 3/5027* (2013.01); *B01L 2300/023* (2013.01); *B01L 2400/0424* (2013.01)

(58) Field of Classification Search
CPC ................. G16H 10/40; B01L 2400/0424
See application file for complete search history.

(56) References Cited

U.S. PATENT DOCUMENTS

| | | |
|---|---|---|
| 5,632,957 A | 5/1997 | Heller et al. |
| 5,958,791 A | 9/1999 | Roberts et al. |
| 6,149,789 A | 11/2000 | Benecke et al. |

(Continued)

FOREIGN PATENT DOCUMENTS

| | | |
|---|---|---|
| CN | 1337580 A | 2/2002 |
| CN | 1348100 A | 5/2002 |

(Continued)

OTHER PUBLICATIONS

Asbury et al. Trapping of DNA by dielectrophoresis. Electrophoresis 23:2658-2666 (2002).

(Continued)

*Primary Examiner* — Robert A Sorey
*Assistant Examiner* — Kristine K Rapillo
(74) *Attorney, Agent, or Firm* — Wilson Sonsini Goodrich & Rosati

(57) ABSTRACT

Systems, devices, media, methods, and kits are disclosed to integrate and exchange information of analyte analysis kits. Analyte analysis can be performed and presented using in association with advertising or questions.

19 Claims, 8 Drawing Sheets

(56) References Cited

U.S. PATENT DOCUMENTS

| | | |
|---|---|---|
| 6,203,683 B1 | 3/2001 | Austin et al. |
| 6,280,590 B1 | 8/2001 | Cheng et al. |
| 6,289,590 B1 | 9/2001 | McDonald |
| 6,294,063 B1 | 9/2001 | Becker et al. |
| 6,403,367 B1 | 6/2002 | Cheng et al. |
| 6,557,575 B1 | 5/2003 | Gerhardt et al. |
| 6,749,736 B1 | 6/2004 | Fuhr et al. |
| 6,824,664 B1 | 11/2004 | Austin et al. |
| 6,887,362 B2 | 5/2005 | Huang et al. |
| 7,081,189 B2 | 7/2006 | Squires et al. |
| 7,105,081 B2 | 9/2006 | Gascoyne et al. |
| 7,709,262 B2 | 5/2010 | Cantor et al. |
| 8,425,750 B2 | 4/2013 | Sugioka |
| 8,603,791 B2 | 12/2013 | Krishnan et al. |
| 8,815,554 B2 | 8/2014 | Krishnan et al. |
| 8,815,555 B2 | 8/2014 | Krishnan et al. |
| 8,871,481 B2 | 10/2014 | Krishnan et al. |
| 8,877,470 B2 | 11/2014 | Krishnan et al. |
| 8,932,447 B2 | 1/2015 | Heller et al. |
| 8,932,815 B2 | 1/2015 | Krishnan et al. |
| 8,969,059 B2 | 3/2015 | Krishnan et al. |
| 9,005,941 B2 | 4/2015 | Krishnan et al. |
| 9,034,578 B2 | 5/2015 | Krishnan et al. |
| 9,034,579 B2 | 5/2015 | Krishnan et al. |
| 9,206,416 B2 | 12/2015 | Krishnan et al. |
| 9,387,489 B2 | 7/2016 | Charlot et al. |
| 9,499,812 B2 | 11/2016 | Krishnan et al. |
| 9,682,385 B2 | 6/2017 | Charlot et al. |
| 9,827,565 B2 | 11/2017 | Krishnan et al. |
| 9,918,702 B2 * | 3/2018 | Tariyal ............... A61F 13/2045 |
| 2001/0045359 A1 | 11/2001 | Cheng et al. |
| 2002/0036142 A1 | 3/2002 | Gascoyne et al. |
| 2003/0146100 A1 | 8/2003 | Huang et al. |
| 2004/0011650 A1 | 1/2004 | Zenhausern et al. |
| 2004/0011651 A1 | 1/2004 | Becker et al. |
| 2004/0052689 A1 | 3/2004 | Yao |
| 2004/0086872 A1 | 5/2004 | Childers et al. |
| 2004/0178068 A1 | 9/2004 | Gascoyne et al. |
| 2004/0238052 A1 | 12/2004 | Karp et al. |
| 2006/0063183 A1 | 3/2006 | Segawa et al. |
| 2006/0096367 A1 | 5/2006 | Meyer et al. |
| 2006/0102482 A1 | 5/2006 | Auerswald et al. |
| 2006/0257993 A1 | 11/2006 | McDevitt et al. |
| 2006/0289341 A1 | 12/2006 | Muller et al. |
| 2007/0080062 A1 | 4/2007 | Harnett et al. |
| 2007/0095669 A1 | 5/2007 | Lau et al. |
| 2007/0107910 A1 | 5/2007 | McGuire et al. |
| 2007/0125650 A1 | 6/2007 | Scurati et al. |
| 2007/0131554 A1 | 6/2007 | Yu et al. |
| 2007/0141605 A1 | 6/2007 | Vann et al. |
| 2007/0152206 A1 | 7/2007 | Cho et al. |
| 2007/0240495 A1 | 10/2007 | Hirahara |
| 2007/0284254 A1 | 12/2007 | Cho et al. |
| 2007/0289341 A1 | 12/2007 | Hollenhorst et al. |
| 2008/0120278 A1 | 5/2008 | Roe et al. |
| 2009/0314644 A1 | 12/2009 | Golan et al. |
| 2009/0325813 A1 | 12/2009 | Wang et al. |
| 2010/0090178 A1 | 4/2010 | Kosowsky et al. |
| 2010/0155246 A1 | 6/2010 | Schnelle et al. |
| 2010/0224493 A1 | 9/2010 | Davalos et al. |
| 2011/0009724 A1 | 1/2011 | Hill et al. |
| 2011/0020785 A1 * | 1/2011 | Lowery, Jr. ............ G16H 50/80 435/5 |
| 2011/0100820 A1 | 5/2011 | Bachmann et al. |
| 2011/0108422 A1 | 5/2011 | Heller et al. |
| 2011/0139620 A1 | 6/2011 | Stumber et al. |
| 2011/0192726 A1 | 8/2011 | Chen et al. |
| 2012/0048403 A1 | 3/2012 | Chappel et al. |
| 2012/0110620 A1 | 5/2012 | Kilar et al. |
| 2013/0052748 A1 | 2/2013 | Campbell et al. |
| 2013/0189794 A1 | 7/2013 | Emeric et al. |
| 2013/0237431 A1 | 9/2013 | Lo et al. |
| 2013/0260372 A1 | 10/2013 | Buermann et al. |
| 2013/0273640 A1 | 10/2013 | Krishnan et al. |
| 2014/0054172 A1 | 2/2014 | Jonsson et al. |
| 2014/0093871 A1 | 4/2014 | Shieh et al. |
| 2014/0138260 A1 | 5/2014 | Briman |
| 2014/0170679 A1 | 6/2014 | Aitchison et al. |
| 2014/0206412 A1 | 7/2014 | Dejohn et al. |
| 2014/0296089 A1 | 10/2014 | Holmes et al. |
| 2014/0367260 A1 | 12/2014 | Dickerson et al. |
| 2015/0004077 A1 | 1/2015 | Wikswo et al. |
| 2015/0037786 A1 | 2/2015 | Salsman |
| 2015/0136604 A1 | 5/2015 | Nielsen et al. |
| 2015/0197784 A1 | 7/2015 | Williams et al. |
| 2015/0266022 A1 | 9/2015 | Eltoukhy et al. |
| 2015/0283553 A1 | 10/2015 | Charlot et al. |
| 2015/0301031 A1 | 10/2015 | Zin et al. |
| 2016/0011115 A1 | 1/2016 | Chen et al. |
| 2016/0175840 A1 | 6/2016 | Ingber et al. |
| 2016/0232562 A1 | 8/2016 | Esayian et al. |
| 2016/0327549 A1 | 11/2016 | Charlot et al. |
| 2017/0039344 A1 | 2/2017 | Bitran et al. |
| 2017/0072395 A1 | 3/2017 | Krishnan et al. |
| 2017/0137870 A1 | 5/2017 | Krishnan et al. |
| 2017/0161452 A1 * | 6/2017 | Bain ................. G06Q 30/0269 |
| 2017/0184545 A1 * | 6/2017 | Azpiroz ........... G01N 27/44756 |
| 2017/0189904 A1 | 7/2017 | Aravanis et al. |
| 2017/0220736 A1 | 8/2017 | Lo et al. |
| 2017/0229149 A1 * | 8/2017 | Rothschild ........... G11B 27/031 |
| 2017/0274378 A1 | 9/2017 | Turner et al. |
| 2017/0370836 A1 * | 12/2017 | Gerion ................ G01N 21/253 |
| 2018/0052093 A1 | 2/2018 | Shi et al. |
| 2019/0210023 A1 | 7/2019 | Turner et al. |

FOREIGN PATENT DOCUMENTS

| | | |
|---|---|---|
| CN | 102037351 A | 4/2011 |
| CN | 102320559 A | 1/2012 |
| EP | 1775589 A1 | 4/2007 |
| GB | 2516666 A | 2/2015 |
| JP | 2001500252 A | 1/2001 |
| JP | 2002502047 A | 1/2002 |
| JP | 2004532968 A | 10/2004 |
| JP | 2008298575 A | 12/2008 |
| JP | 2011516867 A | 5/2011 |
| WO | WO-9804355 A1 | 2/1998 |
| WO | WO-9938612 A1 | 8/1999 |
| WO | WO-0196025 A2 | 12/2001 |
| WO | WO-2005012872 A2 | 2/2005 |
| WO | WO-2005031300 A2 | 4/2005 |
| WO | WO-2005121767 A1 | 12/2005 |
| WO | WO-2006018981 A1 | 2/2006 |
| WO | WO-2007106552 A2 | 9/2007 |
| WO | WO-2007107910 A1 | 9/2007 |
| WO | WO-2009146143 A2 | 12/2009 |
| WO | WO-2014015187 A1 | 1/2014 |
| WO | WO-2014028222 A1 | 2/2014 |
| WO | WO-2015157217 A1 | 10/2015 |
| WO | WO-2015196141 A1 | 12/2015 |
| WO | WO-2017165852 A1 | 9/2017 |
| WO | WO-2017181030 A2 | 10/2017 |
| WO | WO-2018208820 A1 | 11/2018 |
| WO | WO-2019195196 A1 | 10/2019 |

OTHER PUBLICATIONS

Asbury et al. Trapping of DNA in Nonuniform Oscillating Electric Fields. Biophys J. 74:1024-1030 (1998).

Becker et al. Separation of Human Breast Cancer Cells From Blood by Differential Dielectric Affinity. Proceedings of the National Academy of Sciences 92:860-864 (1995).

Becker et al. The removal of human leukemia cells from blood using interdigitated microelectrodes. J Phys. D: Appl. Phys. 27:2659-2662 (1994).

Bettegowda et al. Detection of Circulating Tumor DNA in Early- and Late-Stage Human Malignancies. Sci Transl Med. 6:224 (2014).

Board et al. DNA Methylation in Circulating Tumour DNA as a Biomarker for Cancer. Biomark Insights 2:307-319 (2007).

Board et al. Isolation and extraction of circulating tumor DNA from patients with small cell lung cancer. Ann. N. Y. Acad. Sci. 1137:98-107 (Aug. 2008).

(56) References Cited

OTHER PUBLICATIONS

Cairns. Detection of promoter hypermethylation of tumor suppressor genes in urine from kidney cancer patients. Ann N Y Acad Sci. 1022:40-43 (Jun. 2004).
Casciano et al. Circulating Tumor Nucleic Acids: Perspective in Breast Cancer. Breast Care 5:75-80 (2010).
Catarino et al. Quantification of Free circulating tumor DNA as a diagnostic marker for breast cancer. DNA Cell Biol. 27(8):415-421 (Aug. 2008).
Chan. Circulating EBV DNA as a tumor marker for nasopharyngeal carcinoma. Semin Cancer Biol. 12(6):489-496 (Dec. 2002).
Chan et al. Nasopharyngeal carcinoma. Annals of Oncology 13:1007-1015 (2002).
Chan et al. Persistent Aberrations in Circulating DNA Integrity after Radiotherapy Are Associated with Poor Prognosis in Nasopharyngeal Carcinoma Patients. Clinical Cancer Research 14(13):4141-4145 (2008).
Chan et al. Quantitative Analysis of Circulating Methylated DNA as a Biomarker for Hepatocellular Carcinoma. Clinical Chemistry 54(9):1528-1536 (2008).
Chan et al. Radiological, pathological and DNA remission in recurrent metastatic nasopharyngeal carcinoma. BMC Cancer 6:259 (Oct. 31, 2006).
Cheng et al. Isolation of Cultured Cervical Carcinoma Cells Mixed with Peripheral Blood Cells on a Bioelectronic Chip. Analytical Chemistry 70(11):2321-2326 (1998).
Cheng et al. Preparation and Hybridization Analysis of DNA/A from *E. coli* on Microfabricated Bioelectronic Chips. Nature Biotechnology 16:541-546 (1998).
Cheng et al. Quantification of circulating cell-free DNA in the plasma of cancer patients during radiation therapy. Cancer Science 100(2):303-309 (Feb. 2009).
Chuang et al. Detectable BRAF mutation n serum DNA samples from patients with papillary thyroid carcinomas. Head Neck 32(2):229-234 (2010).
Chun et al. Circulating tumour-associated plasma DNA represents an independent and informative predictor of prostate cancer. BJU International 98(3):544-548 (2006).
Combaret et al. Circulating MYCN DNA as a Tumor-specific Marker in Neuroblastoma Patients. Cancer Research 62:3646-3648 (Jul. 1, 2002).
Cortese et al. Epigenetic markers of prostate cancer in plasma circulating DNA. Human Molecular Genetics 21:3619-3631 (2012).
Da Silva et al. Circulating cell-free DNA in serum as a biomarker of colorectal cancer. Journal of Clinical Pathology 66(9):775-778 (Sep. 2013).
Daniotti et al. Detection of mutated BRAFV600E variant in circulating DNA of stage III-IV melanoma patients. Int. J. Cancer 120:2439-2444 (Jun. 1, 2007).
Dawson et al. Analysis of circulating tumor DNA to monitor metastatic breast cancer. N Engl J Med 368:1199-1209 (2013).
De Maio et al. Circulating and stool nucleic acid analysis for colorectal cancer diagnosis. World Journal of Gastroenterology 20(4):957-967 (Jan. 28, 2014).
Delgado. Characterization of cell-free circulating DNA in plasma in patients with prostate cancer. Tumor Biol. 34(2):983-986 (Apr. 2013).
Deligezer et al. Effect of adjuvant chemotherapy on integrity of free serum DNA in patients with breast cancer. Ann N Y Acad Sci. 1137:175-179 (Aug. 2008).
Devos et al. Circulating Methylated SEPT9 DNA in Plasma Is a Biomarker for Colorectal Cancer. Clinical Chemistry 55(7):1337-1346 (Jul. 2009).
Dobrzycka. Circulating free DNA and p53 antibodies in plasma of patients with ovarian epithelial cancers. Annals of Oncology 22(5):1133-1140 (May 2011).
Dobrzycka. Circulating free DNA, p53 antibody and mutations of KRAS gene in endometrial cancer. 127(3):612-621 (Aug. 1, 2010).

El Tarhouny et al. Comparison of serum VEGF and its soluble receptor sVEGFR1 with serum cell-free DNA in patients with breast tumor. Cytokine 44(1):65-69 (Oct. 2008).
Ellinger et al. Cell-free circulating DNA: diagnostic value in patients with testicular germ cell cancer. J. Urol. 181(1):363-371 (Jan. 2009).
Ellinger et al. CpG island hypermethylation of cell-free circulating serum DNA in patients with testicular cancer. J. Urol. 182(1):324-329 (Jul. 2009).
Ellinger et al. Noncancerous PTGS2 DNA fragments of apoptotic origin in sera of prostate cancer patients qualify as diagnostic and prognostic indicators. Int. J. Cancer 122(1):138-143 (Jan. 1, 2008).
Elshimali et al. The Clinical Utilization of Circulating Cell Free DNA (CCFDNA) in Blood of Cancer Patients. Int. J. Mol. Sci. 14(9):18925-18958 (Sep. 13, 2013).
Fuhr et al. Cell manipulation and cultivation under a.c. electric field influence in highly conductive culture media. Biochimica et Biophysica Acta 1201:353-360 (1994).
Gahan et al. Circulating nucleic acids in plasma and serum: diagnosis and prognosis in cancer. EPMA Journal 1(3):503-512 (Sep. 2010).
Ganepola et al. Use of blood-based biomarkers for early diagnosis and surveillance of colorectal cancer. World Journal of Gastrointestinal Oncology 6(4):83-97 (Apr. 15, 2014).
Gautschi et al. Circulating deoxyribonucleic Acid as prognostic marker in non-small-cell lung cancer patients undergoing chemotherapy. J Clin Oncol. 22(20):4157-4164 (2004).
Goessl et al. DNA Alterations in Body Fluids as Molecular Tumor Markers for Urological Malignancies. European Urology 41(6):668-676 (Jun. 2002).
Gornik et al. Free serum DNA is an early predictor of severity of acute pancreatitis. Clin Biochem. 42(1-2):38-43 (Jan. 2009).
Green et al. Ac electrokinetics: a survey of sub-micrometre paricle dynamics. J. Phys. D: Appl. Phys. 33:632-641 (2000).
Guan et al. Analysis of circulating DNA level in the plasma of cervical cancer patients. Nan fang Yi Ke Da Xue Xue Bao 28(9):1663-1667 (Aug. 2008) (English Abstract).
Hashad et al. Free circulating tumor DNA as a diagnostic marker for breast cancer. J Clin Lab Anal. 26(6):467-472 (Nov. 2012).
Higgins et al. Variant Ciz1 is a circulating biomarker for early-stage lung cancer. PNAS USA 109(45):E3128-3135 (Nov. 6, 2012).
Higuchi. Chromosomal DNA fragmentation inapoptosis and necrosis induced by oxidative stress. Biochem Pharacol. 66:1527-1535(2003).
Higuchi et al. Appearance of 1-2 Mbp giant DNA fragments as an early common response leading to cell death induced by various substances that cause oxidative stress. Free Radical Biology & Medicine 23:90-99 (1997).
Hoffmann et al. Methylated DAPK and APC promoter DNA detection in peripheral blood is significantly associated with apparent residual tumor and outcome. J Cancer Res Clin Oncol. 135(89):1231-1237 (Sep. 2009).
Hoffmann et al. Universal protocol for grafting PCR primers onto various lab-on-a-chip substrates for solid-phase PCR. RSC Advances 2:3885-3889 (2012).
Hohaus et al. Cell-free circulating DNA in Hodgkin's and non-Hodgkin's lymphomas. Annals of Oncology 20(8):1408-1413 (2009).
Holdhoff et al. Blood-based biomarkers for malignant gliomas. J Neurooncol 113:345-352 (2013).
Holzel et al. Trapping Single Molecules by Dielectrophoresis. Phys. Rev. Lett. 95:128102 (2005).
Hosny et al. Ser-249 TP53 and CTNNB1 mutations in circulating free DNA of Egyptian patients with hepatocellular carcinoma versus chronic liver diseases. Cancer Lett. 264(2):201-208 (Jun. 18, 2008).
Huang et al. Dielectrophoretic Cell Separation and Gene Expression Profiling on Microelectronic Chip Arrays. Analytical Chem. 74:3362-3371 (2002).
Huang et al. Electric Manipulation of Bioparticles and Macromolecules on Microfabricated Electrodes. Analytical Chemistry (73):1549-1559 (2001).
Huang et al. Functionalization of Surfaces by Water-Accelerated Atom-Transfer Radical Polymerization of Hydroxyethyl Methacrylate and Subsequent Derivatization. Macromolecules 35:1175-1179 (2002).

(56) References Cited

OTHER PUBLICATIONS

Hughes. Chapter 16: Nanoparticle Manipulation by Electrostatic Forces. Handbook of Nanoscience, Engineering and Technology 2nd Ed., WA Goddard III, DW Brenner, S. Lyshenski & G. Iafrate (eds.) (CRC Press 2007), pp. 16-1 to 16-32.
Hughes et al. Dielectrophoretic Characterization and Separation of Antibody-Coated Submicrometer Latex Spheres. Anal Chem 71:3441-3445 (1999).
Hughes et al. Dielectrophoretic Manipulation and Characterization of Herpes Simplex Virus-1 Capsids. Eur Biophys J 30:268-272 (2001).
Hughes. Strategies for Dielectrophoretic Separation in Laboratory-on-a-chip Systems. Electrophoresis 23:2569-2582 (2002).
Iida et al. Relation between serum levels of cell-free DNA and inflammation status in hepatitis C virus-related hepatocellular carcinoma. Oncology Reports 20(4):761-765 (Oct. 2008).
Iizuka et al. Elevated Levels of Circulating Cell-free DNA in the Blood of Patients with Hepatitis C Virus-associated Hepatocellular Carcinoma. Anticancer Research 26(6C):4713-4720 (2006).
Jiang et al. Dynamic monitoring of plasma circulating DNA in patients with acute myeloid leukemia and its clinical significance. Zhingguo Shi Yan Xue Ye Xue Za Zhi 20(1):53-56 (Feb. 2012) (Abstract).
Jiang et al. Increased plasma DNA integrity index in head and neck cancer patients. Int. J. Cancer 119(11):2673-2676 (Dec. 2006).
Jin et al. Circulating DNA-Important Biomarker of Cancer. Journal of Molecular Biomarkers & Diagnosis S2 (2012) (7 pgs.).
Kakimoto et al. Microsatellite analysis of serum DNA in patients with oral squamous cell carcinoma. Oncology Reports 20(5):1195-1200 (Nov. 2008).
Kolesnikova et al. Circulating DNA in the blood of gastric cancer patients. Ann N Y Acad Sci. 1137:226-231 (Aug. 2008).
Krishnan et al. Alternating current electrokinetic separation and detection of DNA nanoparticles in high-conductance solutions. Electrophoresis 29(9):1765-1774 (2008).
Krishnan et al. An AC electrokinetic method for enhanced detection of DNA nanoparticles. J. Biophotonics 2(4):253-261 (2009).
Krishnan et al. Interaction of nanoparticles at the DEP microelectrode interface under high conductance conditions. Electrochem. Comm. 11(8):1661-1666 (2009).
Kuhlmann et al. LOH at 6q and 10q in fractionated circulating DNA of ovarian cancer patients is predictive for tumor cell spread and overall survival. BMC Cancer 12:3525 (Jul. 31, 2012).
Lavon et al. Serum DNA can define tumor-specific genetic and epigenetic markers in gliomas of various grades. Neuro-Oncology 12(2):173-180 (2010).
Lee et al. Methylation of TMEFF2 Gene in Tissue and Serum DNA from Patients with Non-Small Cell Lung Cancer. Molecules and Cells 34(2):171-176 (Aug. 31, 2012).
Liggett et al. Differential Methylation of Cell-Free Circulating DNA Among Patients With Pancreatic Cancer Versus Chronic Pancreatitis. Cancer 116(7):1674-1680 (Apr. 1, 2010).
Liggett et al. Methylation patterns in cell-free plasma DNA reflect removal of the primary tumor and drug treatment of breast cancer patients. Int. J. Cancer 128(2):492-499 (Jan. 15, 2011).
Lo Nigro et al. Methylated Tissue Factor Pathway Inhibitor 2 (TFPI2) DNA in Serum Is a Biomarker of Metastatic Melanoma. Journal of Investigative Dermatology 133(5):1278-1285 (May 2013).
Lofton-Day et al. DNA Methylation Biomarkers for Blood-Based Colorectal Cancer Screening. Clinical Chemistry 54(2):414-423 (Feb. 2008).
Ma et al. Detection of circulating hypermethylated tumor-specific RASSF1A DNA in ovarian cancer patients. Zhonghua Bing Li Xue Za Zhi. 34(12):785-787 (Dec. 2005) (Abstract).
Ma et al. Methylated DNA and microRNA in Body Fluids as Biomarkers for Cancer Detection. International Journal of Molecular Sciences 14(5):10307-10331 (May 16, 2013).
Majchrzak et al. Detection of MGMT, RASSF1A, p15INK4B, and p14ARF promoter methylation in circulating tumor-derived DNA of central nervous system cancer patients. J. Appl. Genetics 54:335-344 (2013).
Melnikov et al. Methylation profile of circulating plasma DNA in patients with pancreatic cancer. J Surg Oncol. 99(2):119-122 (Feb. 2009).
Menachery et al. Controlling cell destruction using dielectrophoretic forces. IEE Proc.—Nanobiotechnol. 152(4):145-149 (2005).
Mirza et al. Clinical significance of promoter hypermethylation of ERβ and RARβ2 in tumor and serum DNA in Indian breast cancer patients. Ann Surg Oncol. 19(9):3107-3115 (Sep. 2012).
Misale et al. Emergence of KRAS mutations and acquired resistance to anti EGFR therapy in colorectal cancer. Nature 486(7404):532-536 (Jun. 28, 2012).
Misawa et al. RASSF1A hypermethylation in pretreatment serum DNA of neuroblastoma patients: a prognostic marker. British Journal of Cancer 100:399-404 (2009).
Morgan et al. Separation of Sub micron Bioparticles by Dielectrophoresis Biophysical Journal. 77:516-525 (1999).
Mouliere et al. Circulating Cell-Free DNA from Colorectal Cancer Patients May Reveal High KRAS or BRAF Mutation Load. Translational Oncology 6(3):319-328 (Jun. 2013).
Muller et al. DNA Methylation in Serum of Breast Cancer Patients: An Independent Prognostic Marker. Cancer Research 63(22):7641-7645 (Nov. 15, 2003).
Muller et al. Identification of Loss of Heterozygosity on Circulating Free DNA in Peripheral Blood of Prostate Cancer Patients: Potential and Technical Improvements. Clinical Chemistry 54(4):688-696 (Apr. 2008).
Nakagawa et al. Fabrication of amino Silane-Coated Microchip for DNA extraction from Whole Blood. Journal of Biotechnology 116(2):105-111 (2005).
Nakamoto et al. Detection of Microsatellite Alterations in Plasma DNA of Malignant Mucosal Melanoma Using Whole Genome Amplification. Bull Tokyo Dent. Coll. 49(2):77-87 (May 2008).
Nakamura et al. Application of a Highly Sensitive Detection System for Epidermal Growth Factor Receptor Mutations in Plasma DNA. Journal of Thoracic Oncology 7(9):1369-1381 (Sep. 2012).
Nakayama et al. A Highly Sensitive Method for the Detection of p16 Methylation in the Serum of Colorectal Cancer Patients. Anticancer Research 27(3B):1459-1464 (2007).
Page et al. Detection of HER2 amplification in circulating free DNA in patients with breast cancer. British Journal of Cancer 104:1342-1348 (2011).
Pang et al. Microsatellite alterations of circulating DNA in the plasma of patients with hepatocellular carcinoma. Zhonghua Yi Xue Za Zhi. 86(24):1662-1665 (Jun. 27, 2006) (Abstract).
Papadopoulou et al. Cell-free DNA and RNA in Plasma as a New Molecular Marker for Prostate and Breast Cancer, Ann. NY, Acad. Sci. 1075:235-243 (2006).
PCT/US2009/039565 International Preliminary Report on Patentability and Written Opinion dated Oct. 5, 2010.
PCT/US2009/039565 International Search Report dated Dec. 23, 2009.
PCT/US2013/036845 International Preliminary Report on Patentability and Written Opinion dated Oct. 30, 2014.
PCT/US2013/036845 International Search Report and Written Opinion dated Aug. 6, 2013.
PCT/US2015/024624 International Preliminary Report on Patentability dated Oct. 20, 2016.
PCT/US2015/024624 International Search Report and Written Opinion dated Aug. 21, 2015.
PCT/US2015/036789 International Preliminary Report on Patentability dated Dec. 29, 2016.
PCT/US2015/036789 International Search Report and Written Opinion dated Sep. 29, 2015.
PCT/US2017/024149 International Search Report and Written Opinion dated Jul. 18, 2017.
PCT/US2017/024149 Invitation to Pay Additional Fees dated May 15, 2017.

(56) References Cited

OTHER PUBLICATIONS

Pethig. Dielectrophoresis: Using Inhomogenous AC Electrical Fields to Separate and Manipulate Cells, CRC Critical Reviews in Biotechnology, CRC Press, Boca Raton, FL, US. 16(4):331-348 (Jan. 1, 1996).
Ponomaryova et al. Potentialities of aberrantly methylated circulating DNA for diagnostics and post-treatment follow-up of lung cancer patients. Lung Cancer. 81(3):397-403 (Sep. 2013).
Ramos et al. Ac electrokinetics: a review of forces in microelectrode structures. J Phys. D: Appl. Phys. 31:2338-2353 (1998).
Ren et al. Circulating DNA level is negatively associated with the long-term survival of hepatocellular carcinoma patients. World Journal of Gastroenterology 12(24):3911-3914 (Jun. 28, 2006).
Sai et al. Quantification of Plasma Cell-free DNA in Patients with Gastric Cancer. Anticancer Research 27(4C):2747-2752 (2007).
Sakakura et al. Quantitative Analysis of Tumor-derived Methylated RUNX3 Sequences in the Serum of Gastric Cancer Patients. Anticancer Research 29:2619-2626 (2009).
Salkeni et al. Detection of EGFRvIII mutant DNA in the peripheral blood of brain tumor patients. J. Neurooncol. 115(1):27-35 (Oct. 2013).
Sawabu et al. Serum tumor markers and molecular biological diagnosis in pancreatic cancer. Pancreas 28(3):263-267 (Apr. 2004).
Schwarzenbach. Detection and monitoring of cell-free DNA in blood of patients with colorectal cancer. Ann N Y Acad Sci. 1137:190-196 (Aug. 2008).
Schwarzenbach. Loss of Heterozygosity at Tumor Suppressor Genes Detectable on Fractionated Circulating Cell-Free Tumor DNA as Indicator of Breast Cancer Progression. Clinical Cancer Research 18:5719-5730 (Sep. 25, 2012).
Sharma et al. DNA methylation of circulating DNA: a marker for monitoring efficacy of neoadjuvant chemotherapy in breast cancer patients. Tumour Biol. 33(6):1837-1843 (Dec. 2012).
Shaw et al. Genomic analysis of circulating cell-free DNA infers breast cancer dormancy. Genome Research 22(2):220-231 (Feb. 2012).
Sonnenberg et al. Dielectrophoretic isolation and detection of cfc-DNA nanoparticulate biomarkers and virus from blood. Electrophoresis 34(7):1076-1084 (2013).
Sonnenberg et al. Dielectrophoretic Isolation of DNA and Nonoparticles from Blood. Electrophoresis 33(16):2482-2490 (2012).
Sorenson. Detection of Mutated KRAS2 Sequences as Tumor Markers in Plasma/Serum of Patients with Gastrointestinal Cancer. Clin Cancer Res 6:2129-2137 (2000).
Sosnowski et al. Rapid determination of single base mismatch mutations in DNA hybrids by direct electric field control. PNAS USA 94:1119-1123 (Feb. 1997).
Stephens et al. The dielectrophoresis enrichment of CD34+ cells from peripheral blood stern cell harvests. Bone Marrow Transplant. 18:777-782 (1996).
Stroun et al. Isolation and characterization of DNA from the plasma of cancer patients. Eur J Cancer Clin Oneol 23:707-712 (1987).
Swanson. A fully multiplexed CMOS biochip for DNA analysis. Sensors and Actuators B 64:22-30 (Jun. 2000).
Tamkovich et al. Cell-surface-bound circulating DNA as a prognostic factor in lung cancer. Ann N Y Acad Sci. 1137:214-217 (Aug. 2008).
Tanaka et al. Role of circulating free alu DNA in endometrial cancer. Int J Gynecol Cancer 22(1):82-86 (Jan. 2012).
Tangkijvanich et al. Serum LINE-1 hypomethylation as a potential prognostic marker for hepatocellular carcinoma. Clin Chim Acta. 379(1-2):127-133 (Apr. 2007).
Tani et al. An early detection of recurrence using reverse transcriptase-polymerase chain reaction (RT-PCP) and methylation-specific plymerase chain reaction (MSP) from peripheral blood in patients after gastrectomy. Gan to Kagaku Ryoho 33(12):1720-1722 (Nov. 2006) (Abstract).
Tomita et al. Quantification of Circulating Plasma DNA Fragments as Tumor Markers in Patients with Esophageal Cancer, Anticancer Research 27(4C):2737-2742 (2007).
Toner et al. Blood-on-a-chip. Annual Review of Biomedical Engineering 7:77-103 (2005).
Tong et al. Diagnostic developments involving cell-free (circulating) nucleic acids. Clinica Chimica Acta. 363:187-96 (2006).
Toth et al. Free circulating DNA based colorectal cancer screening from peripheral blood: the possibility of the methylated septin 9 gene marker. Orv. Hetil. 150(21):969-977(May 24, 2009) (English Abstract).
Trevisiol et al. Prognostic value of circulating KRAS2 gene mutations in colorectal cancer with distant metastases. Int J Biol Markers. 21(4):223-228 (Oct.-Dec. 2006).
Tuukanen et al. Carbon nanotubes as electrodes for dielectrophoresis of DNA. Nano Letters. 6:1339-1343 (2006).
Umetani et al. Increased Integrity of Free Circulating DNA in Sera of Patients with Colorectal or Periampullary Cancer: Direct Quantitative PCR for ALU Repeats. Clinical Chemistry 52(6):1062-1069 (Jun. 2006).
Umetani et al. Prediction of Breast Tumor Progression by Integrity of Free Circulating DNA in Serum. Journal of Clinical Oncology 24(26):4270-4276 (Sep. 10, 2006).
U.S. Appl. No. 12/936,147 Office Action dated Apr. 27, 2015.
U.S. Appl. No. 12/936,147 Office Action dated Aug. 12, 2015.
U.S. Appl. No. 12/936,147 Office Action dated Dec. 11, 2012.
U.S. Appl. No. 12/936,147 Office Action dated Jul. 18, 2013.
U.S. Appl. No. 12/936,147 Office Action dated Mar. 17, 2017.
U.S. Appl. No. 12/936,147 Office Action dated Oct. 31, 2012.
U.S. Appl. No. 12/936,147 Office Action dated Sep. 22, 2016.
U.S. Appl. No. 13/864,179 Office Action dated Aug. 15, 2013.
U.S. Appl. No. 14/063,884 Office Action dated Aug. 28, 2014.
U.S. Appl. No. 14/063,884 Office Action dated Feb. 12, 2014.
U.S. Appl. No. 14/067,841 Office Action dated Mar. 16, 2015.
U.S. Appl. No. 14/194,566 Office Action dated May 15, 2014.
U.S. Appl. No. 14/201,715 Office Action dated May 15, 2014.
U.S. Appl. No. 14/201,726 Office Action dated May 16, 2014.
U.S. Appl. No. 14/271,337 Office Action dated Jun. 12, 2014.
U.S. Appl. No. 14/311,037 Office Action dated Sep. 5, 2014.
U.S. Appl. No. 14/477,800 Office Action dated Dec. 15, 2014.
U.S. Appl. No. 14/477,800 Office Action dated Feb. 2, 2015.
U.S. Appl. No. 14/509,022 Office Action dated Jan. 15, 2015.
U.S. Appl. No. 14/512,356 Office Action dated Feb. 5, 2015.
U.S. Appl. No. 14/680,819 Office Action dated Dec. 3, 2015.
U.S. Appl. No. 14/925,157 Office Action dated Mar. 22, 2016.
U.S. Appl. No. 15/171,876 Office Action dated Oct. 12, 2016.
U.S. Appl. No. 15/293,062 Office Action dated Mar. 22, 2017.
U.S. Appl. No. 15/320,730 Office Action dated Oct. 4, 2017.
U.S. Appl. No. 15/469,406 Office Action dated Mar. 28, 2018.
Wallner et al. Methylation of Serum DNA Is an Independent Prognostric Marker in Colorectal Cancer. Clinical Cancer Research 12(24):7347-7352 (Dec. 15, 2006).
Washizu et al. Applications of electrostatic stretch-and-positioning of DNA. Industry Applications. IEEE Transactions on Industry Applications 31:447-456 (1995).
Washizu et al. Electrostatic manipulation of DNA in microfabricated structures. Industry Applications. IEEE Transactions on Industry Applications 26:1165-1172 (1990).
Weaver et al. Methylated tumor-specific DNA as a plasma biomarker in patients with glioma. Cancer Invest. 24(1):35-40 (Feb. 2006).
Weiss et al. Circulating tumor DNA to monitor metastatic breast cancer. New England Journal of Medicine. 369(1):93 (Jul. 4, 2013).
Widschwendter et al. CDH1 and CDH13 Methylation in Serum is an Independent Prognostic Marker in Cervical Cancer Patients. Int. J. Cancer 109(2):163-166 (Mar. 20, 2004).
Wu et al. Cell-free DNA: measurement in various carcinomas and establishment of normal reference range. Clin Chim Acta. 321(1-2):77-87 (2002).
Xie et al. Quantification of plasma DNA as a screening tool for lung cancer. Chinese Medical Journal 117(10):1485-1488 (Oct. 2004).
Yoon et al. Comparison of Circulating Plasma DNA Levels between Lung Cancer Patients and Healthy Controls. Journal of Molecular Diagnostics 11(3):182-185 (May 2009).
Zachariah et al. Circulating cell-free DNA as a potential biomarker for minimal and mild endometriosis. Reprod Biomed Online 18(3):407-411 (Mar. 2009).

(56) References Cited

OTHER PUBLICATIONS

Zachariah et al. Levels of circulating cell-free nuclear and mitochondrial DNA in benign and malignant ovarian tumors. Obstet. Gynecol. 112(4):843-850 (Oct. 2008).

Zhou et al. Circulating cell-free nucleic acids: promising biomarkers of hepatocellular carcinoma. Semin Oncol. 39(4):440-448 (Aug. 2012).

Ziegler et al. Circulating DNA: a new diagnostic gold mine? Cancer Treat Rev. 28:255-271 (2002).

Zurita et al. Hypermethylated 14-3-3-σ and ESR1 gene promoters in serum as candidate biomarkers for the diagnosis and treatment efficacy of breast cancer metastasis. BMC Cancer 10(217) 9 pgs (May 2010).

PCT/US2018/031652 International Search Report and Written Opinion dated Jul. 31, 2018.

U.S. Appl. No. 15/991,717 Office Action dated Nov. 2, 2018.

PCT/US2019/025242 International Search Report and Written Opinion dated Jun. 11, 2019.

U.S. Appl. No. 15/991,717 Office Action dated Jul. 9, 2019.

PCT/US2018/066602 International Search Report and Written Opinion dated Apr. 4, 2019.

PCT/US2018/066605 International Search Report and Written Opinion dated Mar. 25, 2019.

Persat, et al., Purification of Nucleic Acids from Whole Blood Using Isotachophoresis, Analytical Chemistry, 81.22 (Nov. 15, 2009): 9507-9511, supporting materials.

U.S. Appl. No. 16/355,462 Office Action dated Sep. 3, 2020.

\* cited by examiner

METHODS AND SYSTEMS FOR ANALYTE INFORMATION PROCESSING

CROSS-REFERENCE

This application claims the benefit of U.S. Provisional Application Ser. No. 62/503,174, filed May 8, 2017, which is incorporated herein by reference in its entirety.

BACKGROUND OF THE INVENTION

Identification and quantification of analytes is important in diagnosing and treating many conditions that impair human health. Further data analysis on the usage of analytes aids clinical management.

SUMMARY OF THE INVENTION

The present technologies fulfill a need for improved methods of analyzing biological samples. Particular attributes of certain aspects provided herein include methods of analyzing usage of analyte kits and assisting clinical management.

The technologies disclosed herein provide an innovative solution to various challenges facing traditional medical testing. Traditional medical testing is a time-consuming process typically requiring a subject to visit a clinic or hospital to provide a biological sample. The sample is delivered to a test facility, oftentimes at a different location, where the actual sample analysis is performed. The subject then must wait for the test results, which may take days or even weeks. Even in emergency situations when rush testing is requested, a subject may be forced to wait for hours in the emergency room due to various factors beyond his or her control such as the availability of testing resources and personnel at the particular medical location. Alternatively, a subject may collect the sample at home and mail the sample to a test facility. Aside from simple tests that do not require data analysis or specialized equipment and can be performed at home (e.g. home pregnancy test), these routine and conventional medical testing approaches are time-consuming and unpredictable in terms of when the results will be provided.

Accordingly, the systems, devices, media, and methods disclosed herein overcome the limitations of the conventional approach by providing a new paradigm for carrying out analyte testing, analysis, and result sharing.

One advantage provided by the present disclosure is the ability to carry out portable testing that is not limited to the clinic setting unlike conventional testing methods. For example, an analyte analysis apparatus and cartridge can be sized for portability. In addition, the apparatus can be configured for use with another electronic device such as, for example, a mobile phone. The electronic device can then supply the apparatus with power and optionally a camera for use in performing the analyte testing. In addition, the processing power of the electronic device can be leveraged to carry out the analysis of the analyte testing. Alternatively, the apparatus or the electronic device may have a network component enabling access to a network such as the Internet, which allows the testing results to be uploaded to the network (e.g. a cloud computing network via the Internet) for analysis. Finally, the electronic device typically has a display screen that can be used to show the results of the test along with any advertisements or questions. By off-loading power, test equipment (e.g. the camera), and data analysis onto electronic devices or a network, the design of the analyte analysis apparatus may be stream-lined or simplified for greater portability. Alternatively, or in combination, the apparatus may utilize batteries as a primary or secondary power source such as in case of the electronic device being low in battery power. The portability of this testing system is further enhanced through the use of a disposable cartridge, thus avoiding potential challenges in cleaning the apparatus outside of the clinic setting.

Another advantage provided by the present disclosure is the ability to obtain results in real-time, often within minutes of initiating analyte analysis. Whereas conventional medical testing requires a series of steps carried out by multiple personnel with the actual testing typically performed off-site at a test facility or lab, the analyte analysis in the present disclosure can be performed in real-time on location (e.g. at home or the point-of-care). The analyte analysis apparatus can be used by a subject to carry out the testing. The testing data may be automatically uploaded to an electronic device and/or a cloud platform for data analysis. Finally, the results of the analysis may be provided to the subject or a user via the electronic device.

Another advantage provided by the present disclosure is the ability for a single individual to carry out the testing. Conventional medical testing requires multiple personnel in addition to the subject such as the nurse obtaining a biological sample, a technician running the analyte testing, and a doctor explaining the results. This can lead to mislabeling or delays due to the number of personnel involved. In contrast, a subject can use the technologies disclosed herein to conduct solo testing using his or her own sample and be able to access the results without requiring a middleman. Alternatively, in some cases, a healthcare provider may run the test with the subject's sample and access the results immediately such as through a web portal or a software application on an electronic device without requiring a technician.

Another advantage provided by the present disclosure is the integration of subject test data with a network such that the subject, healthcare providers, and optionally third parties are able to access the information in a HIPAA compliant manner upon proper authorization. Thus, regardless of whether the test is conducted at home by the subject or by a healthcare provider at a clinic, the test data/results may be provisioned on a network platform that enables access by both the subject and the healthcare provider. For example, a subject may personally conduct testing at home, and then provide authorization to his family doctor to view the results via a secured online web portal. This presents a significant advantage over conventional systems in which the healthcare provider maintains records of its testing on a proprietary server or database which are available upon patient request. In such conventional systems, there is inadequate means for a subject to share test results with his healthcare provider, and typically requires the subject to physically bring the results to a doctor's visit. Moreover, the combination of mobile or portable on-site testing with network data integration and sharing with authorized healthcare providers or third parties provides an innovative solution to disease management. For example, such testing systems can be distributed to an at-risk population to test for a particular disease, and as real-time data is uploaded onto the network, disease investigators can track the spread of the disease and plan accordingly. This implementation contrasts with the conventional approach that requires healthcare workers to be on-location to test and monitor the disease, which can skew the results (e.g. primarily obtaining data from population centers where testing is conducted) and put these healthcare workers at risk of infection.

Another advantage provided by the present disclosure is the provisioning of advertisements and/or survey questions/information prompts in combination with point-of-care or at-home testing. While the analyte analysis apparatus carries out the testing, the capabilities of the electronic device are leveraged to provide a subject with entertainment or useful information in the form of ads and/or questions. Typically, users can view ads on their personal devices such as smartphones. The conventional approach to advertising involves displaying ads on the phone based on user activity on the phone such as a website visited or a selected video. In contrast, the ads and questions disclosed herein may be presented by the electronic device in conjunction with analyte testing by the analyte analysis apparatus, which is a new and unconventional approach. In some cases, the ads or questions are designed to be shown during the analyte testing and/or analysis for efficient time use. For example, the ads or survey questions may be configured to take no more time than the time required for analyte testing and/or analysis (e.g. a movie trailer is limited to the 2 minute time period required to perform a particular analyte testing). Moreover, the ads or survey questions can be directed to alternative devices aside from the electronic device helping to perform the analyte testing such as, for example, a laptop computer, a tablet, or a TV in communication with the electronic device. In some cases, the ads or survey questions are targeted based on prior analyte testing results (e.g. ads for treatment options available for the condition or disorder indicated by the test results).

In one aspect, disclosed herein are systems comprising: a digital processing device comprising: at least one processor, a memory, a display, and an operating system configured to perform executable instructions; an analyte analysis apparatus reversibly accepting and positioning the digital processing device and an analyte analysis cartridge configured to receive a biological material of an individual; a computer program stored in the memory of the digital processing device, the computer program including instructions executable by the digital processing device to create an application comprising: a software module controlling the cartridge to perform an analyte analysis of the biological material to generate a result; a software module presenting the result on the display of the digital processing device; and a software module selecting one or more ads from a population of ads or one or more questions from a population of questions to present in association with the result. In some embodiments, the analyte analysis apparatus positions the digital processing device and an analyte analysis cartridge relative to each other to perform the analyte analysis. In some embodiments, the digital processing device further comprises a camera and wherein the analyte analysis apparatus positions the analyte analysis cartridge such that the camera of the digital processing device can capture an image of a result field of the cartridge. In some embodiments, the image is analyzed by a machine learning algorithm to generate the result. In some embodiments, the digital processing device or the analyte analysis apparatus provides power to the cartridge. In some embodiments, the cartridge is a dielectrophoresis (DEP) cartridge. In some embodiments, the biological material is a biological fluid. In some embodiments, the biological fluid is whole blood, plasma, serum, saliva, cerebrospinal fluid, lymph fluid, urine, sweat, tears, amniotic fluid, aqueous humor, vitreous humor, pleural fluid, mucus, synovial fluid, exudate, interstitial fluid, peritoneal fluid, pericardial fluid, sebum, semen, or bile. In some embodiments, the one or more ads are selected based on a user profile of the individual, the analyte, the result, a location of the digital processing device, or a combination thereof. In some embodiments, the user profile comprises medical information. In some embodiments, the user profile comprises information pertaining to adherence to treatment regimen. In some embodiments, the one or more ads are targeted to the individual based on the individual undergoing a current treatment. In some embodiments, the software module selecting one or more ads receives instructions from a remote server to select the one or more ads, wherein the selection is based on analysis performed by the remote server. In some embodiments, a response by the individual to the one or more ads is added to a user profile of the individual. In some embodiments, the one or more ads are provided by a third-party ad network. In some embodiments, the application further comprises a software module providing an interface allowing upload of the result to an online database. In some embodiments, the application further comprises a software module providing a query interface allowing search of the online database. In some embodiments, the online database is searchable by a biotechnology or pharmaceutical company. In some embodiments, the online database is accessible to authorized third parties. In some embodiments, a user profile for the individual is stored on the online database. In some embodiments, the online database is encrypted. In some embodiments, third party applications are prevented from accessing private information stored in the online database. In some embodiments, the application further comprises a software module selecting one or more questions from a population of questions to present in association with the result. In some embodiments, the application further comprises a software module providing at least one of a treatment recommendation and a healthcare provider recommendation generated by a machine learning algorithm based on a user profile of the individual, the analyte, the result, a location of the digital processing device, historical treatment outcome data for a cohort of patients matched to the individual, healthcare provider information, or a combination thereof. In some embodiments, the software module selecting one or more questions receives instructions from the remote server to select the one or more questions, wherein the selection is based on analysis performed by the remote server. In some embodiments, the application provides the individual with a choice between the one or more ads and the one or more questions. In some embodiments, a response by the individual to the one or more questions is added to a user profile of the individual. In some embodiments, the result is geotagged with a location of the digital processing device and uploaded to a database. In some embodiments, analyte analysis comprises analyte capture, image acquisition, and data analysis. In some embodiments, data analysis is performed remotely through cloud computing. In some embodiments, the digital processing device sends a communication over a network to another device of the user. In some embodiments, the communication comprises one or more ads displayed on another device. In some embodiments, the another device is a cell phone, a smart phone, a tablet, a laptop, a television, an electronic reader (E-reader), a projector, or a monitor. In some embodiments, the communication comprises an alert that user interaction is needed. In some embodiments, the user interaction is selecting one or more ads for display by the digital processing device, selecting one or more questions for display by the digital processing device, viewing one or more ads, viewing one or more questions, or viewing the result. In some embodiments, the communication comprises one or more questions for display on another device. In some embodiments, the system further comprises a software module for obtaining usage statistics for the digital processing device. In some embodiments, the usage statistics are shared with a third party.

Additionally provided herein are computer-implemented systems comprising: a digital processing device comprising: at least one processor, a memory, and an operating system configured to perform executable instructions; an analyte analysis apparatus reversibly accepting and positioning the digital processing device and an analyte analysis cartridge configured to receive a biological material of an individual; a computer program stored in the memory of the digital processing device, the computer program including instructions executable by the digital processing device to create an application comprising: a software module controlling the cartridge to perform an analyte analysis of the biological material to generate a result; a software module transmitting the result to an online database, the online database searchable via a query interface; and a software module selecting one or more ads from a population of ads or one or more questions from a population of questions to present in association with one or more results in response to a search performed in the query interface by a data consumer.

Further provided herein are computer-implemented systems comprising: a digital processing device comprising: at least one processor, a memory, a display, and an operating system configured to perform executable instructions; an analyte analysis apparatus reversibly accepting and positioning the digital processing device and an analyte analysis cartridge configured to receive a biological material of an individual; a computer program stored in the memory of the digital processing device, the computer program including instructions executable by the digital processing device to create an application comprising: a software module controlling the cartridge to perform an analyte analysis of the biological material to generate a result; a software module presenting the result on the display of the digital processing device; a software module selecting at least one first ad from a population of ads to present in association with the result; a software module transmitting the result to an online database, the online database searchable via a query interface; and a software module selecting at least one second ad from the population of ads to present in association with one or more results in response to a search performed in the query interface by a data consumer.

Also provided herein are computer-implemented methods. Such methods comprising transmitting, by a digital processing device, a control signal to a cartridge of an analyte analysis apparatus to perform an analyte analysis of a biological material of an individual to generate a result; presenting, by the digital processing device, the result on a display of a digital processing device; and selecting, by the digital processing device, one or more ads from a population of ads or one or more questions from a population of questions to present in association with the result.

Also provided herein are non-transitory computer readable storage media encoded with a program including instructions executable by at least one processor of a digital processing device to create an application comprising: a software module transmitting a control signal to a cartridge of an analyte analysis apparatus to perform an analyte analysis of a biological material of an individual to generate a result; a software module presenting the result on a display; and a software module selecting one or more ads from a population of ads or one or more questions from a population of questions to present in association with the result.

Additionally provided herein are computer-implemented method comprising: transmitting, by a digital processing device, a control signal to a cartridge of an analyte analysis apparatus to perform an analyte analysis of a biological material of an individual to generate a result; providing, by the digital processing device, an interface allowing upload of the result to an online database; providing, by the digital processing device, a query interface allowing search of the online database; and selecting, by the digital processing device, one or more ads from a population of ads or one or more questions from a population of questions to present in association with one or more results in response to a search performed in the query interface.

Also provided herein are non-transitory computer readable storage media encoded with a program including instructions executable by at least one processor of a digital processing device to create an application comprising: a software module transmitting a control signal to a cartridge of an analyte analysis apparatus to perform an analyte analysis of a biological material of an individual to generate a result; a software module providing an interface allowing upload of the result to an online database; and a software module selecting one or more ads from a population of ads or one or more questions from a population of questions to present in association with the result.

Further provided herein are computer-implemented methods comprising: transmitting, by a digital processing device, a control signal to a cartridge of an analyte analysis apparatus to perform an analyte analysis of a biological material of an individual to generate a result; presenting, by the digital processing device, the result on a display; selecting, by the digital processing device, at least one first ad from a population of ads to present in association with the result; providing, by the digital processing device, an interface allowing upload of the result to an online database; providing, by the digital processing device, a query interface allowing search of the online database; and selecting, by the digital processing device, at least one second ad from the population of ads to present in association with one or more results in response to a search performed in the query interface.

Also provided herein are non-transitory computer readable storage media encoded with a program including instructions executable by at least one processor of a digital processing device to create an application comprising: a software module transmitting a control signal to a cartridge of an analyte analysis apparatus to perform an analyte analysis of a biological material of an individual to generate a result; a software module presenting the result on a display; a software module selecting at least one first ad from a population of ads to present in association with the result; a software module providing an interface allowing upload of the result to an online database; a software module providing a query interface allowing search of the online database; and a software module selecting at least one second ad from the population of ads to present in association with one or more results in response to a search performed in the query interface.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

DETAILED DESCRIPTION OF THE INVENTION

The technologies disclosed herein relate to a need for improved computer-implemented methods of analyzing and managing usage of analyte tests. Particular attributes of certain aspects provided herein include methods of analyzing and sharing results of analyte tests and assisting clinical management.

Data Analysis Overview

Figure 1:
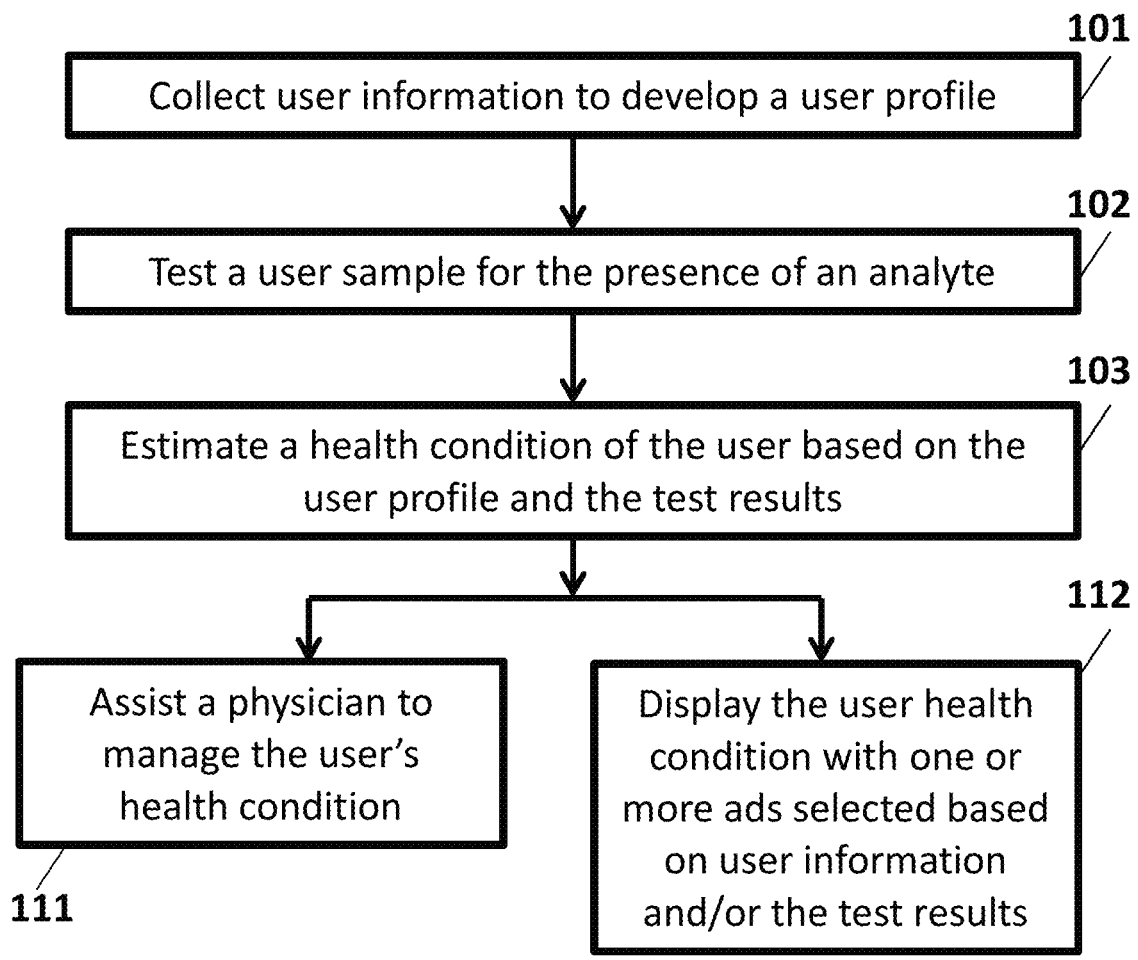
FIG. 1 illustrates an example data analysis flow chart.

In various embodiments, the computing systems, media, method, or kit disclosed herein includes data analysis, realized based on software application or computing hardware or both. An analysis application or system comprises at least a data processing module. FIG. 1 illustrates an overview of a data processing flow. In step 101, a system or a method comprises collecting user information to develop a user profile. In some embodiments, user information comprises one or more of a user name, a user ethnic background, a user age, a user height and weight, and medical information, such as a diagnosis and one or more symptoms. In some embodiments, user information comprises health information or health data. If applicable, standard HIPAA (Health Insurance Portability and Accountability Act of 1996) will govern how this information is stored and disseminated. For example, in some embodiments, health data comprises a "limited data set" of identifiable patient information as defined by HIPAA (e.g., for purposes of protecting patient confidentiality and/or privacy). In some embodiments, the health data is anonymized to remove all identifying information. In some embodiments, patient information is stored on a database. In some embodiments, the database is encrypted. In some embodiments, the database prevents access to patient information by applications unrelated to the systems and methods disclosed herein (e.g. mobile applications installed on a phone).

Referring again to FIG. 1, in some embodiments, operation 102 tests a user sample for the presence of an analyte. In some embodiments, the user sample is tested using an analyte kit. In some embodiments, the analyte kit comprises an analyte analysis apparatus and a cartridge (e.g. a dielectrophoresis and fluidics cartridge). In some embodiments, the analyte kit is configured to interface with a digital processing device utilizing the analyte analysis apparatus and cartridge to carry out imaging of an analyte or sample, analysis of the image or data, provide a power supply to the analyte analysis apparatus, or any combination thereof. In some embodiments, the analyte kit comprises the digital processing device. In some embodiments, the analyte kit isolates an analyte using an assay, such as an immunoassay or a nucleic acid or protein assay. The assay comprises a method of isolating and measuring an analyte. In some cases, the assay is conducted using dielectrophoresis, which allows the analyte to be detected by a probe visualized creating an electrical signal to be detected by one or more sensors. The analyte kit summarizes patterns of the one or more electrical signals. The analyte kit transmits the patterns, or the one or more electrical signals, or both, to the data processing module. In operation 103 the system or the method estimates a health condition of the user based on the user profile 101 and the test results 102. In operation 111, the system or the method assists a physician to manage the subject's health. In operation 112, the system or the method displays the user health condition with one or more ads selected based on the user information and/or the test results. In some embodiments, the systems, devices, and methods described herein further provide one or more recommendations based on the user information and/or test results. In some embodiments, the recommendations comprise an identified local healthcare provider or service near the user (current location and/or user's home/work address) based on test results indicating the user is suffering from a health condition, disease, or disorder. As an illustrative example, a diabetic user performs self-testing using the analyte analysis apparatus and cartridge in combination with his smartphone, and the test results indicate he is suffering from a healthcare condition such as low blood sugar. Accordingly, based on his user profile indicating his diabetic condition and the test result indicating low blood sugar, his smartphone displays the test results, information on treating the condition (e.g. eat some carbohydrates), and identifies a nearby emergency room the user can visit or call for help along with a button for immediately placing a call to the emergency room.

Figure 2:
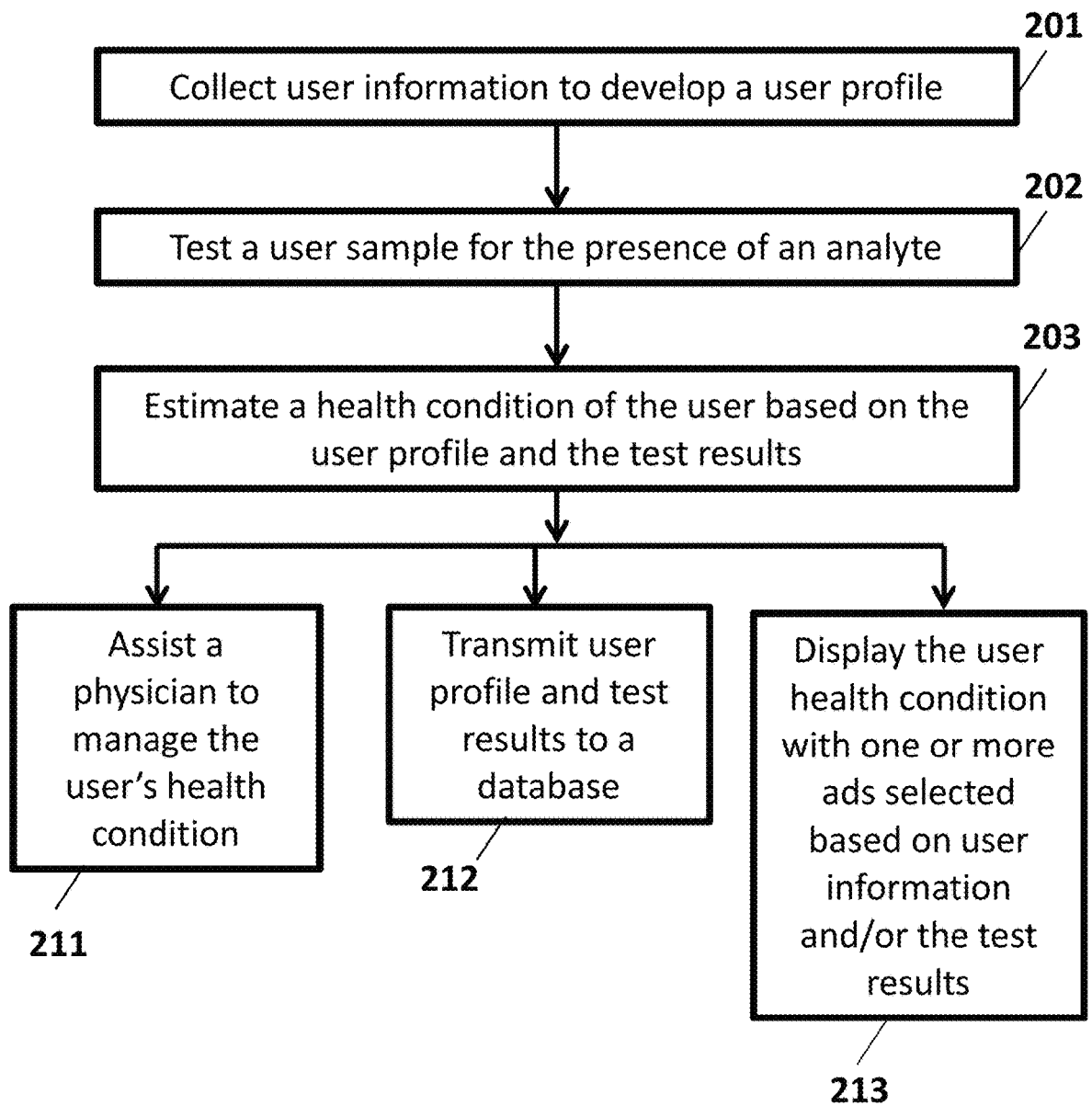
FIG. 2 illustrates an alternative example analysis flow chart.

FIG. 2 illustrates an alternate overview of a data processing flow. In step 201, a system or a method comprises collecting user information to develop a user profile. In some embodiments, user information comprises one or more of a user name, a user ethnic background, a user age, a user height and weight, and medical information, such as a diagnosis and one or more symptoms. In some embodiments, operation 202 tests a user sample for the presence of an analyte. In some embodiments, the user sample is tested using an analyte kit. The analyte kit isolates an analyte using an assay, such as an immunoassay or a nucleic acid or protein assay. The assay comprises a method of isolating and measuring an analyte. In some cases, the assay is dielectrophoresis, which allows the analyte to be detected by a probe visualized creating an electrical signal to be detected by one or more sensors. The analyte kit summarizes patterns of the one or more electrical signals. The analyte kit transmits the patterns, or the one or more electrical signals, or both, to the data processing module. In operation 203 the system or the method estimates a health condition of the user based on the user profile 201 and the test results 202. In operation 211, the system or the method assists a physician to manage the subject's health. In operation 212, the system or the method transmits the user profile and the test results to a database. In operation 213, the system or the method displays the user health condition with one or more ads selected based on the user information and/or the test results.

In certain aspects, described herein are systems and methods coordinating the use of a diagnostic device (e.g. an analyte analysis apparatus) with targeted advertisements and/or a database of users and their results. In some embodiments, the diagnostic device is a consumer-facing device that is usable outside of a clinic setting such as at home. In some embodiments, consumer-operated devices are configured to be compact and/or portable and adapted to be used in combination with a digital processing device such as a mobile phone. For example, a diagnostic device adapted for consumer use can allow for the use of a smartphone comprising a camera for capturing an image of the analyte, a processor for performing data analysis, a hard drive for data storage or communication interface for uploading data for storage via a network, and a display for showing the results of the analysis and optionally ads and/or questions. By offloading these various functions onto the smartphone, the analyte analysis apparatus or diagnostic device can be manufactured using fewer resources so as to be more affordable to consumers. This design also enables the apparatus to be streamlined for greater portability and durability (e.g. more rugged design with thicker outer shell and/or having fewer parts that can break). In addition, the reduction in complexity helps accelerate safety testing for new iterations of the analyte analysis apparatus and overall testing system since they would have already been tested for use with the electronic device such as the smartphone. By limiting the apparatus to the essential test equipment, the apparatus may be environment agnostic. For example, the apparatus can simply plug into a phone that is already configured for the local environment (e.g. adapted for 110 AC or 220 AC), and thus can have universal compatibility with local electric grids and networks since those functions are offloaded onto the electronic device. Moreover, performing the analysis and displaying the results off of the apparatus helps address any potential language barriers since the electronic device would present such information in the local language or dialect (e.g. using translation services such as Google translate).

Another advantage of this innovative setup is that an existing iteration of the analyte analysis apparatus (e.g. an early generation model) can achieve improved performance over time as the electronic device (e.g. smartphones) is updated such as with better cameras providing superior resolution and/or clarity. Thus, an analyte analysis apparatus or diagnostic device can extend its lifespan by piggybacking on improvements to the electronic device of the user. Furthermore, this testing system can also offload functions onto a remote server or cloud-based computing system or network. For example, the battery life of the apparatus and/or electronic device can be extended by uploading the testing data for remote analysis. In addition, the speed of analysis may be improved through remote analysis in case the electronic device has low processing power. In some embodiments, a software application (e.g. installed on the electronic device) decides whether to perform the analysis locally on the electronic device or remotely via the network. In some embodiments, this decision is based on at least one of battery life of the electronic device, processing power of the electronic device, estimated time of analysis by the electronic device, estimated time of analysis of the network, and a user selected setting (e.g. user can specify how analysis is to be carried out by adjusting a setting on the user profile). In some embodiments, the systems and methods disclosed herein utilize suitable electronic devices such as smartphones or other devices providing network audiovisual communications to provide telehealth. For example, a user who has obtained the analysis of his/her test results may wish to speak with a physician or expert for further explanation (e.g. has questions beyond what is addressed in the analysis presented through the electronic device). Accordingly, in certain embodiments, the electronic device comprises a software module allowing a user to communicate with a healthcare provider such as by text messaging, email, phone call, video call, or other digital communications.

In some embodiments, the diagnostic device is adapted for use by a healthcare provider such as in the hospital or clinical setting (as used herein, healthcare provider refers not just to individual healthcare providers such as doctors or nurses but also to healthcare providing organizations and businesses such as hospitals, clinics, and healthcare centers). In some embodiments, the diagnostic device is in communication with one or more computing systems and/or databases of the healthcare provider or organization. In some embodiments, the diagnostic device uploads data obtained from imaging the analyte onto a remote server or cloud-based network, which optionally performs analysis of the image(s) and provides the results of the analysis to the healthcare provider. In some embodiments, the results are provided through a web portal. In some embodiments, the results are provided through a software application via an application programming interface (API) of a remote server or cloud-based computing system. In some embodiments, the web portal or software application provides secured user login for the healthcare provider and access to encrypted patient data uploaded from the diagnostic device. In some embodiments, the patient data is anonymized to remove identifying information (e.g. name, address, etc). In some embodiments, the web portal or software application provides tools for parameter-based searching and/or sorting of uploaded data. In some embodiments, the healthcare provider enters information for a (healthcare provider) user profile. The information can include basic identifying information such as name, address, and services offered. In some cases, the healthcare provider enters information useful to promoting the ecosystem maintained by the healthcare platform described herein. Such information can include provider type, type and/or size of practice group(s) or employee categories, location, size, and insurance accepted.

In some embodiments, provided herein is a healthcare platform providing an interactive ecosystem comprising users (e.g. test subjects, patients), healthcare providers (e.g. hospitals, doctors), and third parties (e.g. insurance companies, pharmaceutical companies, universities, health research organizations, etc). In some embodiments, testing is carried out using the systems, devices, and methods described herein, and the results of said testing are uploaded for storage within one or more databases on the platform. In some embodiments, the testing results, analyses, user profile, responses to ads/questions, and any other information stored on the database(s) is encrypted to protect user identity. In some embodiments, the platform comprises a web portal or software application interface (e.g. an app on the user electronic device) allowing a user to review the user profile, testing results, and other information. In some embodiments, the web portal or application interface provides tools for the user to authorize other parties to access information such as testing results. In some embodiments, the tools provide a user with options to select parties to be given authorization to view or access user information, and options to select the type of user information that authorized parties can view or access. In some embodiments, the tools provide a user with the ability to anonymize his information for use by third parties such as, for example, in a research study by a University research group or for patient selection/screening for clinical trials by a pharmaceutical company.

In some embodiments, the web portal or software application provides tools for generating a provider profile for the healthcare provider required to access uploaded data. In some embodiments, the provider profile comprises information about the healthcare provider such as provider type (e.g. hospital, clinic, family doctor), type and/or size of practice group(s) or employee categories (e.g. number of nurse, pediatrician, radiologist, etc), location (e.g. address, city, town, county, state, country), size (e.g. number of employees, doctors, nurses), and insurance accepted. In some embodiments, the provider profile is associated with information obtained from ads and/or questions posed to healthcare providers utilizing the systems described herein. In some embodiments, the healthcare provider is presented with one or more ads selected from a plurality of ads in order to view the results of an analysis as with the consumer-facing diagnostic devices. Examples of ads that may be presented to a healthcare provider include advertisements of drugs, therapies, surgical tools, hospital equipment, medical malpractice insurance, medical business consulting, and political ads relating to healthcare legislation. In some embodiments, the healthcare provider is presented with one or more questions selected from a plurality of questions in order to view the results of an analysis. Examples of questions that may be presented to a healthcare provider include questions as to number of patients processed (e.g. in a day or week), frequency of various reasons for patient visits (e.g. cold symptoms, injury, heart condition, surgery, etc), price of various services, commonly prescribed drugs, preferred medications (e.g. favors prescribing brand-name vs generic), and willingness to change service/prescriptions based on factors such as price or effectiveness. In some embodiments, the ads presented to a healthcare provider are personalized based on the provider profile information and/or information gathered from previously viewed ads and/or answered questions. As an example, a personalized ad may be an advertisement for a generic drug touting that it is 10 times cheaper than the name-brand formulation while being just as effective based on the provider's response to a question indicating a willingness to switch to a generic prescription based on price so long as efficacy is equal. In some embodiments, multiple ads for the same product or service can be configured, each having a different angle or hook such as price, effectiveness, reputation, or other advertising approaches. The ad for the product or service may then be personalized by choosing one of the various approaches based on correlating the response rate of the ads (e.g. click, purchase, or conversion rate) to historical data. For example, analysis of historical ad/question response data for all or related healthcare providers may reveal that certain data predict increased susceptibility to particular advertising approaches than others. In some embodiments, the questions presented to a healthcare provider are personalized based on the provider profile information and/or information gathered from previously viewed ads and/or answered questions. As an example, a personalized question may ask the healthcare provider the reason the provider prescribes a name-brand medication instead of the generic formulation based on previous answers or profile information indicating this preference. In some embodiments, the healthcare provider is prompted to provide information while running a test using the diagnostic device. For example, the healthcare provider may be prompted to indicate the frequency, timing, and/or nature of the test (e.g. the $4^{th}$ daily test performed for a patient undergoing chemotherapy). In some embodiments, the diagnostic device automatically uploads metadata to the remote server or cloud-based network. In some embodiments, the metadata is linked to the healthcare provider and/or the patient whose biological sample is being tested. In some embodiments, the metadata is linked to the provider or patient anonymously such that the provider or patient identity cannot be determined. In some embodiments, anonymity is provided using encryption (e.g. asymmetric encryption).

In some embodiments, the diagnostic device is configured for use in a commercial setting such as, for example, in a pharmacy or retail stores (e.g. supermarket, department store, mall, etc). As an example, the diagnostic device may be configured as a kiosk or health station similar to the blood pressure health stations frequently placed in pharmacies. In some embodiments, a diagnostic device health station comprises an analyte analysis apparatus, one or more cartridges, and a digital processing device and/or communication interface. In some embodiments, the diagnostic device health station comprises multiple disposable cartridges that are discarded upon each use. In some embodiments, the diagnostic device health station comprises a digital processing device in communication with the analyte analysis apparatus for locally storing data, performing data analysis, communicating with a remote server or cloud-based network, selecting ads to present to the user, or any combination thereof. Alternatively, in some embodiments, the diagnostic device health station comprises a communication interface that communicates with a remote server or cloud-based network for storing data, performing data analysis, selecting ads to present to the user, or any combination thereof. In some embodiments, the diagnostic device health station comprises at least one display for showing a result of the analyte or data analysis, ads, questions/surveys, or other digital information.

Data Analysis Algorithms and Machine Learning Methods

In some embodiments, one or more computing devices carry out data analysis. In some embodiments, data analysis is performed using a computer program. In some embodiments, a computer program comprises a data analysis module configured to analyze signals of an assayed biological sample. In further embodiments, analyzing the signals comprises a use of a statistical analysis. In some cases, analyzing the signals comprises comparing the signals with a signal template. There are various analyses, which can be combined to assemble an analysis module in the computer program. Examples of analyzing the signals include: analyzing strength of the signals, analyzing a frequency of the signals, identifying a spatial distribution pattern of the signals, identifying a temporal pattern of the one or more signals, detecting a discrete fluctuation in the signals corresponding to a chemical reaction event, inferring a pressure level, inferring a temperature level, inferring a light intensity, inferring a color intensity, inferring a conductance level, inferring an impedance level, inferring a concentration of ions, analyzing patterns of one or more AC electrokinetic high field regions and one or more AC electrokinetic low field regions, and analyzing a chemical reaction event. In still further embodiments, a chemical reaction event comprises one or more of the following: a molecular synthesis, a molecular destruction, a molecular breakdown, a molecular insertion, a molecular separation, a molecular rotation, a molecular spinning, a molecular extension, a molecular hybridization, a molecular transcription, a sequencing reaction, and a thermal cycling.

In some embodiments, the data analysis module is configured to detect signals of an assayed biological sample. The signals can comprise one or more images taken of the assayed biological sample. The one or more images can comprise pixel image data. The one or more images can be received as raw image data. The data detection module can be configured to receive pixel image data from a mobile computing device. The pixel image data can be from an image captured by a camera on the mobile computing device. In various embodiments, the data analysis module performs image processing upon the pixel image data. A pixel in an image may be produced by a signal that is a combination of photons produced by the assayed sample and a background signal. Background signal can come from photons emitted or reflected by external light sources. In some cases, certain auto-fluorescent materials can interfere with fluorescence-based assays. Accordingly, measurements of optical signals using the unprocessed pixels may overestimate the signal of the assay. Image processing can be used to reduce noise or filter an image. Image processing can be used to improve signal quality. In various embodiments, the data analysis module performs calibration in order to correct for background noise level using a reference signal (e.g., a null sample). In various embodiments, the data analysis module processes the image to normalize contrast and/or brightness. The data analysis module may perform gamma correction. In some embodiments, the data analysis module converts the image into grayscale, RGB, or LAB color space.

In various embodiments, the data analysis module processes the pixel image data using data processing algorithms to convert the data into a distribution of numerical values based on signal intensity. The pixel image data can comprise spatial information and intensity for each pixel. In various embodiments, the data analysis module selects one or more subfields within the image to be used in determining the result. This process may be necessary in some circumstances. For example, the signal being detected may not fill up the entire field of view of a camera or may be out of position due to misalignment between the camera lens and the assayed biological sample (e.g., the sample may be off-center in the camera's field of view). The one or more subfields can be selected based on the distribution of numerical values. For example, the one or more subfields can be selected based on having a distribution of the highest numerical values. In some embodiments, the data analysis module divides an image into a plurality of subfields and selects one or more subfields to be used in determining the result (e.g., positive or negative detection of cell-free circulating tumor DNA). The data analysis module can use an algorithm to locate a sub-field having an area that comprises a distribution of numerical values representing the highest signal intensity out of a plurality of possible sub-fields. As an illustrative example, an assay that utilizes a fluorescent dye to detect an analyte can produce a fluorescent signal of a certain frequency or color. The data analysis module then divides the image into sub-fields and locates a sub-field having the highest signal intensity. The sub-field having the highest signal intensity may then be used for calculating whether the result is positive or negative for the presence of the analyte. In various embodiments, signal intensity for a sub-field is calculated based on an average, median, or mode of signal intensity for all pixels located within the sub-field. The spatial intensity of the signal can be captured as an image by a camera of a mobile computing device. The image can be converted into a distribution of numerical values based on signal intensity. In various embodiments, the data analysis module normalizes the pixel image set. In various embodiments, the data analysis module receives multiple images or sets of pixel image data corresponding to said multiple images for an assayed biological sample. The data analysis module can analyze the multiple images to generate a more accurate result than analyzing a single image. In some embodiments, the data analysis module analyzes at least 2, 3, 4, 5, 6, 7, 8, 9, 10, 15, 20, 30, 40, or 50 images for an assayed biological sample.

Various algorithms can be used to generate models that predict a result of the analyte testing. In some instances, machine learning methods are applied to the generation of such models (e.g. trained classifier). Such models can be generated by providing a machine learning algorithm with training data in which the expected output is known in advance.

Various algorithms can also be used to predict treatment and/or healthcare options for a user. In some embodiments, the systems, devices, and methods herein comprise a software module providing one or more recommendations to a user. In some embodiments, the software module provides a recommendation in response to a query entered by the user. Alternatively, or in combination, a user is presented with the results of analyte testing along with one or more recommendations based on the results and/or user profile. For example, the one or more recommendations can suggest the nearest hospital with the requisite facilities or resources for treating the specific disorder the user is suffering from (according to the test results and/or user profile information). In some embodiments, an algorithm utilizes a web crawler and/or database to identify the resources available at specific healthcare providers. In some embodiments, treatment information for users who follow the recommendation(s) are analyzed and incorporated to update the algorithm. For example, a user who obtains a positive test result for a highly infectious disease travels to the nearest hospital, for which no information is known according to the algorithm. However, during the course of the visit, the hospital turns out to have a quarantine space and established quarantine protocols that successfully resolve the potential outbreak. This information is uploaded to the platform's online databases along with other treatment information for the user. The algorithm then updates its decision making based on this information such that, for example, this hospital may be recommended for future users who require treatment for an infectious disease (pursuant to other relevant conditions such as proximity to the user or availability of comparable facilities). In some embodiments, the algorithm is a machine learning algorithm that is trained using previous treatment results. For example, a user suffering from a particular disease may be provided with a recommended treatment and/or healthcare provider based on a machine learning algorithm trained with data sets comprising data for subjects having similar conditions and outcome data for available treatments and/or healthcare providers.

Thus, a user suffering from condition A may be provided with a recommendation to visit hospital B based on an algorithm trained using outcome data for the matched cohort of patients who also suffered from condition A and visited hospitals B, C, and D (e.g. the hospitals within a certain driving distance of the user). In some cases, a user may be matched against a cohort of patients based on any of age, gender, disease or condition, duration of disease or condition, symptoms, and other relevant factors. In some embodiments, the algorithm provides one or more recommendations based on the user's own medical history. For example, the algorithm may provide a treatment recommendation based on the user's past responses to various treatments (e.g. a treatment option is removed from consideration because of past instances when the user experienced no effect or an adverse reaction to the treatment). In some embodiments, recommendations are only provided for predictions having an area under curve of at least about 0.6, about 0.7, about 0.8, about 0.9, about 0.95, or about 0.99 when assessed for predictive accuracy using data not used for training. In some embodiments, the systems, devices, and methods described herein comprise an application comprising a software module providing at least one of a treatment recommendation and a healthcare provider recommendation generated by a machine learning algorithm based on a user profile of the individual, the analyte, the result, a location of the digital processing device, historical treatment outcome data for a cohort of patients matched to the individual, healthcare provider information, or a combination thereof. In some embodiments, the software application comprises a software module receiving a user query to provide the one or more recommendations. In some embodiments, the software application comprises a software module automatically generating and providing the one or more recommendation along with the results of the analyte testing.

The classifier or trained machine learning algorithm of the present disclosure can comprise one feature space. In some cases, the classifier comprises two or more feature spaces. The two or more feature spaces may be distinct from one another. Each feature space can comprise types of information about a case, such as biomarker expression or the presence of genetic mutations. The accuracy of the classification may be improved by combining two or more feature spaces in a classifier instead of using a single feature space. The patient and treatment information generally make up the input features of the feature space and are labeled to indicate the classification of each test result for the given set of input features corresponding to that case. In many cases, the classification is the outcome of the test analysis. The training data is fed into the machine learning algorithm which processes the input features and associated outcomes to generate a model. In some cases, the machine learning algorithm is provided with training data that includes the classification (e.g., diagnostic or test result), thus enabling the algorithm to "learn" by comparing its output with the actual output to modify and improve the model. This is often referred to as supervised learning. Alternatively, the machine learning algorithm can be provided with unlabeled or unclassified data, which leaves the algorithm to identify hidden structure amongst the cases (referred to as unsupervised learning). Sometimes, unsupervised learning is useful for identifying the features that are most useful for classifying raw data into separate cohorts.

One or more sets of training data may be generated and used to train a machine learning algorithm. An algorithm may utilize a predictive model such as a neural network, a decision tree, a support vector machine, or other applicable model. Using the training data, an algorithm can form a classifier for classifying the case according to relevant features. The features selected for classification can be classified using a variety of viable methods. The machine learning algorithm may be selected from the group consisting of a supervised, semi-supervised and unsupervised learning, such as, for example, a support vector machine (SVM), a Naïve Bayes classification, a random forest, an artificial neural network, a decision tree, a K-means, learning vector quantization (LVQ), self-organizing map (SOM), graphical model, regression algorithm (e.g., linear, logistic, multivariate, association rule learning, deep learning, dimensionality reduction and ensemble selection algorithms. In some embodiments, the machine learning algorithm is selected from the group consisting of: a support vector machine (SVM), a Naïve Bayes classification, a random forest, and an artificial neural network. Machine learning techniques include bagging procedures, boosting procedures, random forest algorithms, and combinations thereof. Illustrative algorithms for analyzing the data include but are not limited to methods that handle large numbers of variables directly such as statistical methods and methods based on machine learning techniques. Statistical methods include penalized logistic regression, prediction analysis of microarrays (PAM), methods based on shrunken centroids, support vector machine analysis, and regularized linear discriminant analysis.

In some embodiments, the data analysis module performs feature extraction using a feature extraction algorithm to obtain relevant information about the signal while leaving out irrelevant information. Some examples of feature extraction algorithms include histogram of oriented gradients (HOG), scale-invariant feature transform (SIFT), and speeded up robust feature (SURF). Feature extraction algorithms can be used in image processing for threshold detection (thresholding), edge detection, corner detection, blob detection, and ridge detection. In view of the disclosure provided herein, those of skill in the art will recognize that many algorithms are available for performing feature extraction.

In some embodiments, the data analysis module uses a trained algorithm to determine a result for the sample (e.g., positive or negative detection of an analyte or microparticulate). The trained algorithm of the present disclosure as described herein can comprise one feature space. The trained algorithm of the present disclosure as described herein can comprise two or more feature spaces. The two or more feature spaces may be distinct from one another. Each feature space can comprise types of information about a sample, such as presence of a nucleic acid, protein, carbohydrate, lipid, or other macromolecule. Algorithms can be selected from a non-limiting group of algorithms including principal component analysis, partial least squares regression, and independent component analysis. Algorithms can include methods that analyze numerous variables directly and are selected from a non-limiting group of algorithms including methods based on machine learning processes. Machine learning processes can include random forest algorithms, bagging techniques, boosting methods, or any combination thereof. Algorithms can utilize statistical methods such as penalized logistic regression, prediction analysis of microarrays, methods based on shrunken centroids, support vector machine analysis, or regularized linear discriminant analysis. The algorithm may be trained with a set of sample data (e.g., images or pixel image data) obtained from various subjects. The sample data may be obtained from a database described herein such as, for example, an online database storing the results of analyte analyses. A set of samples can comprise samples from at least 10, 20, 30, 40, 50, 60, 70, 80, 90, 100, 150, 200, 250, 300, 350, 400, 450, 500, 600, 700, 800, 900, or 1000 or more subjects. The trained algorithm can be tested using independent samples to determine its accuracy, specificity, sensitivity, positive predictive value, negative predictive value, or any combination thereof. The trained algorithm can have an accuracy of at least 80, 90, 95, or 99%% for a set of at least 100 independent samples. The trained algorithm can have a positive predictive value of at least 80, 90, 95, or 99% for a set of at least 100 independent samples. The trained algorithm can have a specificity of at least 80, 90, 95, or 99% for a set of at least 100 independent samples.

As an example, in the case of algorithms providing treatment or healthcare provider recommendations, examples of features include the analyte, the result, a healthcare condition, age, gender, and other factors affecting the outcome. In some embodiments, the treatment and/or healthcare provider is pre-selected based on location and/or resource availability. For example, a user may enter constraints on treatment by limiting healthcare providers to within a 30 mile radius of the current device location. Next, the available healthcare providers within this radius are identified, their information extracted (e.g. using webcrawlers or existing databases), and then converted into data corresponding to the features of the algorithm. The data are fed into the algorithm to generate an output (e.g. a predicted outcome between 1.0 corresponding to positive outcome and 0.0 corresponding to negative outcome) for each healthcare provider. The providers are then ranked based on the outcome prediction, and the highest ranked provider is presented to the user as the recommended healthcare provider.

In some embodiments, various algorithms are applied to generate predictions or recommendations for third parties or healthcare providers rather than the user. In some embodiments, the recommendations include identified locations having specific healthcare needs. In some embodiments, machine learning algorithms can reveal areas having high clusters of specific types of medical needs (e.g. high rate of a certain infectious). For example, third parties such as epidemiologists can use this information to identify potential outbreaks. In addition, healthcare providers or government health organizations can identify areas requiring increased resources for responding to such healthcare needs. As another example, various algorithms can analyze uploaded user data to determine the fastest growing healthcare needs. Such information can be made accessible to healthcare providers or third parties who receive appropriate authorization. In some embodiments, access to this data is monetized to help make the testing systems, devices, and apparatuses described herein available to the patient population.

In some embodiments, the systems and methods described herein utilize one or more algorithms to perform patient data analytics. As an example, patient data may be analyzed using machine learning algorithm(s) to determine susceptibility to different diseases based on various factors (e.g. age, location, ethnicity, gender, etc). Accordingly, patients who are identified as having a predicted susceptibility to a certain disease may be provided with recommendations to see a doctor, obtain testing, or presented with questions directed to other risk factors or symptoms of the disease. In some embodiments, patient data is sorted into different cohorts based on such factors, allowing matching cohorts to be used to generate personalized recommendations or analyses for individual subjects. For example, ads for a certain treatment popular with a matched cohort of patients having similar demographics as an individual may be selected for presentation to that individual when carrying out analyte testing according to the systems and methods described herein. Similarly, unsupervised machine learning may be applied to a data set to carry out cluster analysis for identifying patient clusters that may be receptive to common treatment modalities. Individuals who are grouped into specific clusters may be targeted with certain ads or questions based on the common characteristics of the cluster.

In some embodiments, machine learning algorithms utilized herein comprise artificial neural networks, which mimic networks of neurons based on the neural structure of the brain. They process input data by comparing the classification of a specific case (e.g. a patient) with the known actual classification of the case (e.g. an outcome such as adverse event). Artificial neural networks are typically organized in layers comprising an input layer, an output layer, and at least one hidden layer, wherein each layer comprises one or more neurons or nodes. Each node in a given layer is connected to the nodes in the preceding layer and the nodes in the subsequent layer. A given node receives input from the nodes in the preceding layer, changes its internal state based on the value of the received input, and generates an output based on the input and activation. This output is sent to the nodes in the subsequent layer, and the process continues until the output layer generates the final output which may be a prediction. As a result, the input propagates through the layers of the neural network to generate a final output classification such as, for example, a value corresponding to a classification such as a known outcome represented by neurons in the output layer. As an example, the output layer may comprise a node corresponding to healthcare provider A or healthcare provider B in the case of an algorithm determining the provider to recommend a individual to for treatment. The output can be ranked according to the values of these respective nodes (which may be normalized to a value between 0 and 1). In a case where the node corresponding to healthcare provider A has a value of 0.9 while the node corresponding to healthcare provider B has a value of 0.1, the output can be ranked with provider A as the number one option and provider B as the number two option. In some cases, treatment options are not ranked and/or presented when they fall below a minimum significance threshold.

Systems

In certain aspects, computer-implemented systems, devices, media, and methods described herein function to coordinate use of a diagnostic device (e.g. an analyte analysis apparatus) with targeted advertisements and optionally a database of users and their results.

In some embodiments, the diagnostic device is an analyte detection system, for example, a dielectrophoresis and fluidics cartridge for isolating and detecting one or more analytes associated with a medical condition. In some embodiments, the diagnostic device comprises an analyte analysis apparatus, a cartridge, or both. In some embodiments, targeted advertisements are selected based on one or more of the user information such as user age, user height and weight, and user medical information. In some embodiments, the database is searchable by a user or patient. In some embodiments, the database is searchable by a research professional. In some embodiments, the database is searchable by a physician. In some embodiments, the database is searchable by a biotechnology or pharmaceutical company. In some embodiments, the online database is accessible to authorized third parties.

Provided herein are computer-implemented systems. Some such systems comprising: a digital processing device comprising: at least one processor, a memory, a display, and an operating system configured to perform executable instructions; an analyte analysis apparatus reversibly accepting and positioning the digital processing device and an analyte analysis cartridge configured to receive a biological material of an individual; a computer program stored in the memory of the digital processing device, the computer program including instructions executable by the digital processing device to create an application comprising: a software module controlling the cartridge to perform an analyte analysis of the biological material to generate a result; a software module presenting the result on the display of the digital processing device; and a software module selecting one or more ads from a population of ads to present in association with the result. In some embodiments, the analyte analysis apparatus positions the digital processing device and an analyte analysis cartridge relative to each other to perform the analyte analysis. In some embodiments, the digital processing device further comprises a camera and wherein the analyte analysis apparatus positions the analyte analysis cartridge such that the camera of the digital processing device can capture an image of a result field of the cartridge. In some embodiments, the image is analyzed by a machine learning algorithm to generate the result. In some embodiments, the digital processing device or the analyte analysis apparatus provides power to the cartridge. In some embodiments, the cartridge is a dielectrophoresis (DEP) cartridge. In some embodiments, the biological material is a biological fluid. In some embodiments, the biological fluid is whole blood, plasma, serum, saliva, cerebrospinal fluid, lymph fluid, urine, sweat, tears, amniotic fluid, aqueous humor, vitreous humor, pleural fluid, mucus, synovial fluid, exudate, interstitial fluid, peritoneal fluid, pericardial fluid, sebum, semen, or bile. In some embodiments, the one or more ads are selected based on a user profile of the individual, the analyte, the result, a location of the digital processing device, or a combination thereof. In some embodiments, the user profile comprises medical information. In some embodiments, the user profile comprises information pertaining to adherence to treatment regimen. In some embodiments, the one or more ads are targeted to the individual based on the individual undergoing a current treatment. In some embodiments, the software module selecting one or more ads receives instructions from a remote server to select the one or more ads, wherein the selection is based on analysis performed by the remote server. In some embodiments, a response by the individual to the one or more ads is added to a user profile of the individual. In some embodiments, the one or more ads are provided by a third-party ad network. In some embodiments, the application further comprises a software module providing an interface allowing upload of the result to an online database. In some embodiments, the application further comprises a software module providing a query interface allowing search of the online database. In some embodiments, the online database is searchable by a biotechnology or pharmaceutical company. In some embodiments, the online database is accessible to authorized third parties. In some embodiments, a user profile for the individual is stored on the online database. In some embodiments, the online database is encrypted. In some embodiments, third party applications are prevented from accessing private information stored in the online database. In some embodiments, the application further comprises a software module selecting one or more questions from a population of questions to present in association with the result. In some embodiments, the application further comprises a software module providing at least one of a treatment recommendation and a healthcare provider recommendation generated by a machine learning algorithm based on a user profile of the individual, the analyte, the result, a location of the digital processing device, historical treatment outcome data for a cohort of patients matched to the individual, healthcare provider information, or a combination thereof. In some embodiments, the software module selecting one or more questions receives instructions from the remote server to select the one or more questions, wherein the selection is based on analysis performed by the remote server. In some embodiments, the application provides the individual with a choice between the one or more ads and the one or more questions. In some embodiments, a response by the individual to the one or more questions is added to a user profile of the individual. In some embodiments, the result is geo-tagged with a location of the digital processing device and uploaded to a database. In some embodiments, analyte analysis comprises analyte capture, image acquisition, and data analysis. In some embodiments, data analysis is performed remotely through cloud computing. In some embodiments, the digital processing device sends a communication over a network to another device of the user. In some embodiments, the communication comprises one or more ads displayed on another device. In some embodiments, the another device is a cell phone, a smart phone, a tablet, a laptop, a television, an electronic reader (E-reader), a projector, or a monitor. In some embodiments, the communication comprises an alert that user interaction is needed. In some embodiments, the user interaction is selecting one or more ads for display by the digital processing device, selecting one or more questions for display by the digital processing device, viewing one or more ads, viewing one or more questions, or viewing the result. In some embodiments, the communication comprises one or more questions for display on another device. In some embodiments, the system further comprises a software module for obtaining usage statistics for the digital processing device. In some embodiments, the usage statistics are shared with a third party.

Additionally provided herein are computer-implemented systems comprising: a digital processing device comprising: at least one processor, a memory, and an operating system configured to perform executable instructions; an analyte analysis apparatus reversibly accepting and positioning the digital processing device and an analyte analysis cartridge configured to receive a biological material of an individual; a computer program stored in the memory of the digital processing device, the computer program including instructions executable by the digital processing device to create an application comprising: a software module controlling the cartridge to perform an analyte analysis of the biological material to generate a result; a software module transmitting the result to an online database, the online database searchable via a query interface; and a software module selecting one or more ads from a population of ads or one or more questions from a population of questions to present in association with one or more results in response to a search performed in the query interface by a data consumer. In some embodiments, the analyte analysis apparatus positions the digital processing device and an analyte analysis cartridge relative to each other to perform the analyte analysis. In some embodiments, the digital processing device further comprises a camera and wherein the analyte analysis apparatus positions the analyte analysis cartridge such that the camera of the digital processing device can capture an image of a result field of the cartridge. In some embodiments, the image is analyzed by a machine learning algorithm to generate the result. In some embodiments, the digital processing device or the analyte analysis apparatus provides power to the cartridge. In some embodiments, the cartridge is a dielectrophoresis (DEP) cartridge. In some embodiments, the biological material is a biological fluid. In some embodiments, the biological fluid is whole blood, plasma, serum, saliva, cerebrospinal fluid, lymph fluid, urine, sweat, tears, amniotic fluid, aqueous humor, vitreous humor, pleural fluid, mucus, synovial fluid, exudate, interstitial fluid, peritoneal fluid, pericardial fluid, sebum, semen, or bile. In some embodiments, the online database interfaces with a social network or other online community. In some embodiments, the query interface allows the data consumer to search by individual, by analyte, by result, or by a combination thereof. In some embodiments, the online database is searchable by a biotechnology or pharmaceutical company. In some embodiments, the online database is accessible to authorized third parties. In some embodiments, a user profile for the individual is stored on the online database. In some embodiments, the online database is encrypted. In some embodiments, third party applications are prevented from accessing private information stored in the online database. In some embodiments, the one or more ads are selected based on a user profile of the individual, the analyte, the result, a location of the digital processing device, or a combination thereof. In some embodiments, the user profile comprises medical information. In some embodiments, the user profile comprises information pertaining to adherence to treatment regimen. In some embodiments, the one or more ads are targeted to the individual based on the individual undergoing a current treatment. In some embodiments, the software module selecting one or more ads receives instructions from a remote server to select the one or more ads, wherein the selection is based on analysis performed by the remote server. In some embodiments, the one or more ads are provided by a third-party ad network. In some embodiments, the application further comprises a software module selecting one or more questions from a population of questions to present in association with one or more results in response to a search performed in the query interface by the data consumer. In some embodiments, the software module selecting one or more questions receives instructions from a remote server to select the one or more questions, wherein the selection is based on analysis performed by the remote server. In some embodiments, the application provides the data consumer with a choice between the one or more ads and the one or more questions. In some embodiments, the result is geo-tagged with a location of the digital processing device and uploaded to a database. In some embodiments, analyte analysis comprises analyte capture, image acquisition, and data analysis. In some embodiments, data analysis is performed remotely through cloud computing. In some embodiments, the digital processing device sends a communication over a network to another device of the user. In some embodiments, the communication comprises one or more ads displayed on another device. In some embodiments, the another device is a cell phone, a smart phone, a tablet, a laptop, a television, an electronic reader (E-reader), a projector, or a monitor. In some embodiments, the communication comprises an alert that user interaction is needed. In some embodiments, the user interaction is selecting one or more ads for display by the digital processing device, selecting one or more questions for display by the digital processing device, viewing one or more ads, viewing one or more questions, or viewing the result. In some embodiments, the communication comprises one or more questions for display on another device. In some embodiments, the system further comprises a software module for obtaining usage statistics for the digital processing device. In some embodiments, the usage statistics are shared with a third party.

Further provided herein are computer-implemented systems comprising: a digital processing device comprising: at least one processor, a memory, a display, and an operating system configured to perform executable instructions; an analyte analysis apparatus reversibly accepting and positioning the digital processing device and an analyte analysis cartridge configured to receive a biological material of an individual; a computer program stored in the memory of the digital processing device, the computer program including instructions executable by the digital processing device to create an application comprising: a software module controlling the cartridge to perform an analyte analysis of the biological material to generate a result; a software module presenting the result on the display of the digital processing device; a software module selecting at least one first ad from a population of ads to present in association with the result; a software module transmitting the result to an online database, the online database searchable via a query interface; and a software module selecting at least one second ad from the population of ads to present in association with one or more results in response to a search performed in the query interface by a data consumer. In some embodiments, the at least one first ad and the at least one second ad are provided by one or more third-party ad networks.

In some embodiments, disclosed herein are non-transitory computer readable storage media encoded with a program including instructions executable by at least one processor of a digital processing device to create an application carrying out the methods or steps described herein.

Methods

Computer-implemented methods herein coordinate use of an at home diagnostic device with targeted advertisements and optionally a database of users and their results. In some embodiments, the at home diagnostic device comprises a dielectrophoresis and fluidics cartridge for isolating and detecting one or more analytes associated with a medical condition. In some embodiments, targeted advertisements are selected based on one or more of the user information such as user age, user height and weight, and user medical information. In some embodiments, the database is searchable by a user. In some embodiments, the database is searchable by a research professional. In some embodiments, the database is searchable by a physician. In some embodiments, the database is searchable by a biotechnology or pharmaceutical company.

Also provided herein are computer-implemented methods. Such methods comprising transmitting, by a digital processing device, a control signal to a cartridge of an analyte analysis apparatus to perform an analyte analysis of a biological material of an individual to generate a result; presenting, by the digital processing device, the result on a display of a digital processing device; and selecting, by the digital processing device, one or more ads from a population of ads or one or more questions from a population of questions to present in association with the result. In some embodiments, the cartridge is configured to receive the biological material of the individual. In some embodiments, the analyte analysis apparatus reversibly accepts and positions the digital processing device and the cartridge. In some embodiments, the analyte analysis apparatus positions the digital processing device and an analyte analysis cartridge relative to each other to perform the analyte analysis. In some embodiments, the digital processing device comprises a camera and wherein the analyte analysis apparatus positions the analyte analysis cartridge such that the camera of the digital processing device can capture an image of a result field of the cartridge. In some embodiments, the image is analyzed by a machine learning algorithm to generate the result. In some embodiments, the digital processing device or the analyte analysis apparatus provides power to the cartridge. In some embodiments, the cartridge is a dielectrophoresis (DEP) cartridge. In some embodiments, the biological material is a biological fluid. In some embodiments, the biological fluid is whole blood, plasma, serum, saliva, cerebrospinal fluid, lymph fluid, urine, sweat, tears, amniotic fluid, aqueous humor, vitreous humor, pleural fluid, mucus, synovial fluid, exudate, interstitial fluid, peritoneal fluid, pericardial fluid, sebum, semen, or bile. In some embodiments, the one or more ads are selected based on a user profile of the individual, the analyte, the result, a location of the digital processing device, or a combination thereof. In some embodiments, the user profile comprises medical information. In some embodiments, the user profile comprises information pertaining to adherence to treatment regimen. In some embodiments, the one or more ads are targeted to the individual based on the individual undergoing a current treatment. In some embodiments, the digital processing device receives instructions from a remote server to select the one or more ads, wherein the selection is based on analysis performed by the remote server. In some embodiments, a response by the individual to the one or more ads is added to a user profile of the individual. In some embodiments, the one or more ads are provided by a third-party ad network. In some embodiments, the method further comprises providing, by the digital processing device, an interface allowing upload of the result to an online database. In some embodiments, the method further comprises providing, by the digital processing device, a query interface allowing search of the online database. In some embodiments, the online database is searchable by a biotechnology or pharmaceutical company. In some embodiments, the online database is accessible to authorized third parties. In some embodiments, a user profile for the individual is stored on the online database. In some embodiments, the online database is encrypted. In some embodiments, third party applications are prevented from accessing private information stored in the online database. In some embodiments, the method further comprises selecting, by the digital processing device, one or more questions from a population of questions to present in association with the result. In some embodiments, the method further comprises providing, by the digital processing device, at least one of a treatment recommendation and a healthcare provider recommendation generated by a machine learning algorithm based on a user profile of the individual, the analyte, the result, a location of the digital processing device, historical treatment outcome data for a cohort of patients matched to the individual, healthcare provider information, or a combination thereof. In some embodiments, the digital processing device receives instructions from a remote server to select the one or more questions, wherein the selection is based on analysis performed by the remote server. In some embodiments, the digital processing device provides the individual with a choice between the one or more ads and the one or more questions. In some embodiments, a response by the individual to the one or more questions is added to a user profile of the individual. In some embodiments, the result is geo-tagged with a location of the digital processing device and uploaded to a database. In some embodiments, analyte analysis comprises analyte capture, image acquisition, and data analysis. In some embodiments, data analysis is performed remotely through cloud computing. In some embodiments, the digital processing device sends a communication over a network to another device of the user. In some embodiments, the communication comprises one or more ads displayed on another device. In some embodiments, the another device is a cell phone, a smart phone, a tablet, a laptop, a television, an electronic reader (E-reader), a projector, or a monitor. In some embodiments, the communication comprises an alert that user interaction is needed. In some embodiments, the user interaction is selecting one or more ads for display by the digital processing device, selecting one or more questions for display by the digital processing device, viewing one or more ads, viewing one or more questions, or viewing the result. In some embodiments, the communication comprises one or more questions for display on another device. In some embodiments, the method further comprises obtaining usage statistics for the digital processing device. In some embodiments, the usage statistics are shared with a third party.

Additionally provided herein are computer-implemented method comprising: transmitting, by a digital processing device, a control signal to a cartridge of an analyte analysis apparatus to perform an analyte analysis of a biological material of an individual to generate a result; providing, by the digital processing device, an interface allowing upload of the result to an online database; providing, by the digital processing device, a query interface allowing search of the online database; and selecting, by the digital processing device, one or more ads from a population of ads or one or more questions from a population of questions to present in association with one or more results in response to a search performed in the query interface. In some embodiments, the cartridge is configured to receive the biological material of the individual. In some embodiments, the analyte analysis apparatus reversibly accepts and positions a digital processing device and the cartridge. In some embodiments, the analyte analysis apparatus positions the digital processing device and an analyte analysis cartridge relative to each other to perform the analyte analysis. In some embodiments, the digital processing device comprises a camera and wherein the analyte analysis apparatus positions the analyte analysis cartridge such that the camera of the digital processing device can capture an image of a result field of the cartridge. In some embodiments, the image is analyzed by a machine learning algorithm to generate the result. In some embodiments, the digital processing device or the analyte analysis apparatus provides power to the cartridge. In some embodiments, the cartridge is a dielectrophoresis (DEP) cartridge. In some embodiments, the biological material is a biological fluid. In some embodiments, the biological fluid is whole blood, plasma, serum, saliva, cerebrospinal fluid, lymph fluid, urine, sweat, tears, amniotic fluid, aqueous humor, vitreous humor, pleural fluid, mucus, synovial fluid, exudate, interstitial fluid, peritoneal fluid, pericardial fluid, sebum, semen, or bile. In some embodiments, the online database interfaces with a social network or other online community. In some embodiments, the query interface allows the data consumer to search by individual, by analyte, by result, or by a combination thereof. In some embodiments, the online database is searchable by a biotechnology or pharmaceutical company. In some embodiments, the online database is accessible to authorized third parties. In some embodiments, a user profile for the individual is stored on the online database. In some embodiments, the online database is encrypted. In some embodiments, third party applications are prevented from accessing private information stored in the online database. In some embodiments, the one or more ads are selected based on a user profile of the individual, the analyte, the result, a location of the digital processing device, or a combination thereof. In some embodiments, the user profile comprises medical information. In some embodiments, the user profile comprises information pertaining to adherence to treatment regimen. In some embodiments, the one or more ads are targeted to the individual based on the individual undergoing a current treatment. In some embodiments, the digital processing device receives instructions from a remote server to select the one or more ads, wherein the selection is based on analysis performed by the remote server. In some embodiments, the one or more ads are provided by a third-party ad network. In some embodiments, the method further comprises selecting, by the digital processing device, one or more questions from a population of questions to present in association with one or more results in response to a search performed in the query interface. In some embodiments, the digital processing device receives instructions to select the one or more questions from a remote server, wherein the selection is based on analysis performed by the remote server. In some embodiments, the digital processing device provides the individual with a choice between the one or more ads and the one or more questions. In some embodiments, the result is geo-tagged with a location of the digital processing device and uploaded to a database. In some embodiments, analyte analysis comprises analyte capture, image acquisition, and data analysis. In some embodiments, data analysis is performed remotely through cloud computing. In some embodiments, the digital processing device sends a communication over a network to another device of the user. In some embodiments, the communication comprises one or more ads displayed on another device. In some embodiments, the another device is a cell phone, a smart phone, a tablet, a laptop, a television, an electronic reader (E-reader), a projector, or a monitor. In some embodiments, the communication comprises an alert that user interaction is needed. In some embodiments, the user interaction is selecting one or more ads for display by the digital processing device, selecting one or more questions for display by the digital processing device, viewing one or more ads, viewing one or more questions, or viewing the result. In some embodiments, the communication comprises one or more questions for display on another device. In some embodiments, the method further comprises obtaining usage statistics for the digital processing device. In some embodiments, the usage statistics are shared with a third party.

Further provided herein are computer-implemented methods comprising: transmitting, by a digital processing device, a control signal to a cartridge of an analyte analysis apparatus to perform an analyte analysis of a biological material of an individual to generate a result; presenting, by the digital processing device, the result on a display; selecting, by the digital processing device, at least one first ad from a population of ads to present in association with the result; providing, by the digital processing device, an interface allowing upload of the result to an online database; providing, by the digital processing device, a query interface allowing search of the online database; and selecting, by the digital processing device, at least one second ad from the population of ads to present in association with one or more results in response to a search performed in the query interface. In some embodiments, the at least one first ad and the at least one second ad are provided by one or more third-party ad networks.

In some embodiments, disclosed herein are non-transitory computer readable storage media encoded with a program including instructions executable by at least one processor of a digital processing device to create an application carrying out the methods or steps described herein.

Analyte Analysis Apparatus

Also provided herein are analyte analysis apparatuses for use with detection methods herein, which are small enough to be easily carried or transported and have very low power requirements. In some embodiments, an analyte analysis apparatus is a compact device. An exemplar compact device is described in PCT/US2017/024149, which is incorporated in its entirety. In some embodiments, the analyte analysis apparatus or compact device reversibly accepts and positions the digital processing device and an analyte analysis cartridge. In some embodiments, the analyte analysis apparatus or compact device performs an analyte analysis. In some embodiments, the compact device is used only for analyte capture and image acquisition while analyte analysis is performed remotely in the cloud. In some embodiments, digital processing devices herein include a mobile computing device such as a mobile phone, smartphone, tablet, wearable computing device (e.g. smartwatch, head-mounted display), personal data assistant (PDA), handheld gaming console, portable media player, personal navigation device, mobile internet device (MID), or laptop computer. In some embodiments, an analyte analysis apparatus integrates various components described herein.

Size

In various embodiments, analyte analysis apparatuses herein are sized to be easily carried by an average person with one hand. In some embodiments, the size and shape of the apparatus is variable depending on the type of mobile computing device to be used in combination with the analyte analysis apparatus. In some embodiments, an analyte analysis apparatus comprises a housing frame to hold a mobile computing device, at least one microfluidic channel, and a fluidic cartridge. In some embodiments, analyte analysis apparatus sized to be used with a mobile computing device is configured to be portable. In some embodiments, a analyte analysis apparatus herein has a height ranging from about 130 mm to about 320 mm, for example about 130, 140, 150, 160, 170, 180, 190, 200, 210, 220, 230, 240, 250, 260, 270, 280, 290, 300, 310, or 320 mm. In some embodiments, analyte analysis apparatuses herein have a width ranging from about 60 mm to about 230 mm, for example about 60, 70, 80, 90, 100, 110, 120, 130, 140, 150, 160, 170, 180, 190, 200, 210, 220, or 230 mm. In some embodiments, analyte analysis apparatuses herein have a depth ranging from about 20 mm to about 100 mm, for example about 20, 30, 40, 50, 60, 70, 80, 90, or 100 mm. In some embodiments, the housing frame is adapted to hold a range of possible mobile computing devices of varying sizes such as, for example, a mobile phone, a mini tablet, or a tablet. In some embodiments, the housing frame comprises one or more members for holding the mobile computing device in place. In some embodiments, the members are adjustable members. In some embodiments, the housing frame comprises one or more adjustable members positioned at a top and/or bottom of the mobile computing device. In some embodiments, the housing frame comprises one or more adjustable members positioned at a left and/or right side of the mobile computing device. In some embodiments, the housing frame comprises one or more adjustable members positioned at a front or back of the mobile computing device. In some embodiments, the members are adjustable via translational or axial movement, rotation, or expansion. In some embodiments, a member is slidable. In some embodiments, a member is flexible. In some embodiments, a member comprises a clamp for gripping the mobile computing unit, wherein the clamp is adjustable (e.g., claws of the clamp are slidable relative to each other for opening and closing their grip). In some embodiments, each member comprises a surface for engaging with a surface of the mobile computing device. In some embodiments, the surface of each member comprises a high friction material (e.g. rubber, non-slip plastic, a textured fabric, foam, polymers, etc.) to prevent sliding of the mobile computing device. In some embodiments, the housing frame comprises a cradle for receiving and positioning the mobile computing device.

In some embodiments, an analyte analysis apparatus is configured to accept and position a mobile computing device so that a camera of the mobile computing device is aligned with an optical pathway to enable the device to take an image, photo, or video. In some embodiments, the analyte analysis apparatus is configured to accept and position a front facing camera of the mobile computing device. In some embodiments, the analyte analysis apparatus is configured to accept and position a rear facing camera of the mobile computing device. In some embodiments, the analyte analysis apparatus accepts and positions a mobile computing device so that a camera of the device is aligned with an optical pathway while also not obstructing a display screen of the device. This configuration provides the advantage of allowing a user to watch ads, answer questions, or otherwise use the device while the test or assay is being performed. In some embodiments, the analyte analysis apparatus comprises an optical pathway that blocks out external light from entering the camera for taking the image. In some embodiments, the device is connected and communicating via internal network to other devices in user's environment, alerting user that interaction needed (Ex: smart home, "the test is done" alert, with ads being displayed on TV instead of phone etc, etc). In some embodiments, the optical pathway comprises a light seal (e.g., a foam light seal) that, upon engagement with the surface of the device, prevents external light from entering the camera aperture.

Power

In various embodiments, analyte analysis apparatuses described herein have the feature of running on very low power, for example on the power provided by a USB or micro USB port. In some cases, the power is provided by the digital processing device. In some cases, the power is provided by a battery pack. In some cases, the power is provided by a solar charger. In some cases, the power is provided by a wall outlet. In some cases, the power is provided by a headphone jack.

In some embodiments, a power supply is embedded into a digital processing device.

In some embodiments, it is contemplated that analyte analysis apparatuses herein are configured to use multiple power sources depending on the source that is available at the time.

Power provided by a USB port is typically understood to be about 5 volts. The maximum current recommended to be drawn from a USB port is about 500 mA. The maximum load of power to be generated by a USB port is 2.5 Watts. Therefore, analyte analysis apparatuses described herein, in some embodiments, have lower power requirements than 5 volts, 500 mA, or 2.5 Watts. In some embodiments, analyte analysis apparatuses herein are powered by a battery pack or wall outlet and have larger power requirements, for example about 2.5 to about 10 Watts. In some embodiments, analyte analysis apparatuses herein have power requirements of less than 0.01 to 10 Watts. In some embodiments, analyte analysis apparatuses herein require less than about 10, 9.5, 9.0, 8.5, 8.0, 7.5, 7.0, 6.5, 6.0, 5.9, 5.8, 5.7, 5.6, 5.5, 5.4, 5.3, 5.2, 5.1, 5.0, 4.9, 4.8, 4.7, 4.6, 4.5, 4.4, 4.3, 4.2, 4.1, 4.0, 3.9, 3.8, 3.7, 3.6, 3.5, 3.4, 3.3, 3.2, 3.1, 3.0, 2.9, 2.8, 2.7, 2.6, 2.5, 2.4, 2.3, 2.2, 2.1, 2.0, 1.9, 1.8, 1.7, 1.6, 1.5, 1.4, 1.3, 1.2, 1.1, 1.0, 0.9, 0.8, 0.7, 0.6, 0.5, 0.4, 0.3, 0.2, 0.1, 0.09, 0.08, 0.07, 0.06, 0.05, 0.04, 0.03, 0.02, or 0.01 Watts.

In some embodiments, analyte analysis apparatuses described herein are contemplated to couple to a digital processing device via a connection port, such as a USB connection port or a micro USB connection port. Connection of the analyte analysis apparatuses to the digital processing device, in some embodiments, allows the analyte analysis apparatus to draw power and also allows the digital processing device to control the analyte analysis apparatus. In some embodiments, analyte analysis apparatuses herein comprise more than one connection port. In some embodiments, analyte analysis apparatuses herein comprise a connection port adapter that allows a user to connect different digital processing devices to the analyte analysis apparatus.

In some embodiments, max power that is drawn from a USB port on a phone is 2.5 W. In some embodiments, the USB port provides 500 mA at 5V.

Communication

In various embodiments, the subject matter disclosed herein includes a communication interface. In some embodiments, a communication interface is embedded in a digital processing device. In some embodiments, a communication interface operates on one or more of the following transmission technologies: 3G communication protocols, 4G communication protocols, 5G communication protocols, IEEE 802.11 standards (e.g. Wi-Fi), Bluetooth protocols, short range, RF communications, satellite communications, visible light communications, and infrared communications. In some embodiments, the analyte analysis apparatus communicates with a digital processing device using one or more wired network protocols or architectures.

In some embodiments, a communication interface is embedded in an analyte analysis apparatus. In some embodiments, the analyte analysis apparatus is configured to communicate with a digital processing device such as a mobile phone, a tablet, a laptop, a personal computer, a router, or other computing device. In some embodiments, the analyte analysis apparatus is configured to communicate wirelessly with a digital processing device. In some embodiments, the analyte analysis apparatus is configured to communicate with a digital processing device via a wired connection. In some embodiments, the analyte analysis apparatus is configured to communicate wirelessly with a remote server or cloud-based network. The remote server or cloud-based can provide data storage and/or data analysis, which can reduce energy usage by the analyte analysis apparatus or the digital processing device. Alternatively, in some embodiments, the data storage and/or data analysis is performed by the analyte analysis apparatus or the digital processing device. In some embodiments, data is temporarily stored locally on the analyte analysis apparatus or digital processing device, and optionally uploaded onto a database on a remote server or cloud-based network. In some embodiments, data is temporarily stored locally on the analyte analysis apparatus or digital processing device when there is no network or internet signal available for data uploading. In further embodiments, the data is uploaded once the network or internet signal is established, and the locally stored data is optionally deleted.

In some embodiments, a communication interface comprises a wired communication interface. Examples include USB, microUSB, Ethernet, lightning port, IEEE 1394 (e.g. FireWire), TCP/IP, RJ45, serial ports, and parallel ports.

Optics

In various embodiments, the subject matter disclosed herein includes a camera or an imaging device to obtain a measurement. In some embodiments, the camera or imaging device obtains a measurement by detecting and/or measuring light. In some embodiments, the camera or imaging device captures an image. In some embodiments, the camera or imaging device captures a photo and/or video. In some embodiments, an image is processed to obtain a measurement. For example, in some embodiments, a measurement comprises quantification of an amount of signal such as light. In some embodiments, a camera or an imaging device is embedded in a digital processing device; for instance, a camera of a mobile computing device, such as a camera on a phone, tablet, or laptop computer. It is contemplated that analyte analysis apparatuses described herein comprise at least one optical pathway through which the camera of the mobile computing device can obtain an image. Cameras on digital processing devices, in some embodiments are integrated into the digital processing devices, such as a camera on a phone, a tablet, or a laptop computer. In some embodiments, external lenses can be adapted onto a camera on a digital processing device to enable the camera to obtain a better image. In some embodiments, the camera is a 12 megapixel camera. In some embodiments, the camera is a 10, 9, 8, 7, 6, 5, 4, or 3 megapixel camera.

In some embodiments, analyte analysis apparatuses herein comprise an optical pathway through which the camera on the mobile computing device is able to obtain an image (e.g., of an assayed biological sample). Optical pathways in analyte analysis apparatuses herein, in some embodiments comprise a typical epi-fluorescence optical pathway, known by those of skill in the art, which detect fluorescent signals via a camera sensor in the digital processing device or an external CMOS (complementary metal-oxide-semiconductor) or CCD (charged coupled device) sensor to determine a quantity of an analyte of interest in a sample. In some embodiments, the optical pathway comprises a microscope objective. In some embodiments, the optical pathway comprises an endoscope objective.

In some embodiments, analyte analysis apparatuses herein comprise a camera and an optical pathway through which the camera is able to obtain an image. In some embodiments, an analyte analysis apparatus is a stand-alone device that does not require a digital processing device such as a smartphone to capture an image, carry out analyte analysis, or upload data (e.g. captured image or analyte analysis result) for storage. In some embodiments, the analyte analysis apparatus comprises an optical sensor capable of imaging the assayed biological sample. Optical pathways in analyte analysis apparatuses herein, in some embodiments comprise a typical epi-fluorescence optical pathway, known by those of skill in the art, which detect fluorescent signals via a camera sensor in the digital processing device or an external CMOS (complementary metal-oxide-semiconductor) or CCD (charged coupled device) sensor to determine a quantity of an analyte of interest in a sample. In some embodiments, the optical pathway comprises a microscope objective.

Fluidics

Analyte analysis apparatuses herein are capable of using a variety of mechanisms for moving fluids through the device including a syringe, a peristaltic pump, or a piezo pump. Fluids move through the device using a compact fluidics chamber of a fluidics cartridge. Exemplary fluidics cartridges are described herein and in the case of analyte analysis apparatus, are sized and shaped to fit inside or dock with the analyte analysis apparatus. In some embodiments, the fluidics cartridge is inserted into the analyte analysis apparatus. In some embodiments, the fluidics cartridge is connected to the analyte analysis apparatus by a hinge. In some embodiments, the fluidics cartridge comprises a slider to cover the sample input port. In some embodiments, the fluidics cartridge comprises a reservoir, for example a sample reservoir, a buffer reservoir, and a waste reservoir. In some embodiments, the fluidics cartridge comprises at least two chambers, for example a test chamber and a control solution chamber. In some embodiments, the fluidics cartridge comprises a port, for example a sample input port, a sample reservoir port, a waste reservoir port, and a buffer reservoir port. In some embodiments, the buffer reservoir port also comprises a pump interface location. In some embodiments, the fluidics cartridge comprises a chip. In some embodiments, the fluidics cartridge comprises two or more chips. In some embodiments, the fluidics cartridge comprises a DEP chip. In some embodiments, the fluidics cartridge and chip comprise an analyte analysis cartridge. In some embodiments, the fluidics cartridge comprises a result field.

In some embodiments, disclosed herein are interchangeable or disposable cartridges for use with the methods and devices disclosed herein. In some embodiment, the cartridge comprises a sample receiver. In other embodiments, the cartridge comprises at least one fluidic channel. In yet other embodiments, the cartridge comprises a sensor. Exemplary embodiments of analyte analysis apparatuses (e.g. compact device) and cartridges that can be used with the methods and devices disclosed herein can be found, for example, in U.S. Provisional Application 62/313,120 entitled "Disposable Fluidic Cartridge and Components," filed Mar. 24, 2016, which is incorporated herein in its entirety for this disclosure.

Electronics

In various embodiments, an analyte analysis apparatus disclosed herein comprises an electronic chip to control the analyte analysis apparatus. In some embodiments, an electronic chip comprises a signal amplifier. In some designs, an electronic chip comprises a differential amplifier.

In various embodiments, an electronic chip is configured to control the cartridge to receive the biological sample. In further embodiments, an electronic chip is configured to control the cartridge to assay the biological sample.

In some embodiments, an electronic chip is configured to energize the biological sample. In further embodiments, energizing the biological sample comprises one or more of the following: an ionization in the biological sample and applying an electric current to the biological sample.

In some embodiments, an electronic chip is configured to acquire signals from the assayed biological sample. Examples of signals include, but not limited to, fluorescence, non-fluorescence, electric, chemical, a current of ions, a current of charged molecules, a pressure, a temperature, a light intensity, a color intensity, a conductance level, an impedance level, a concentration level (e.g., a concentration of ions), and a kinetic signal.

In certain embodiments, signals comprise an alternating current (AC) electrokinetic signal. In some cases, the signals comprise one or more AC electrokinetic high field regions and one or more AC electrokinetic low field regions.

Sensors

In various embodiments, the system, devices, and methods described herein include one or more sensors, or use the same. Examples of sensors include, but not limited to, RF tags, speed sensors, acoustic sensors, water sensors, direction sensors, temperature sensors, infrared sensors, liquid sensors, gas sensors, carbon dioxide sensors, carbon monoxide sensors, oxygen sensors, hydrogen sensors, ozone sensors, electrochemical gas sensors, radiation sensors, breathalyzers, holographic sensors, motion sensors, acceleration sensors, pressure sensors, torque sensors, force sensors, gyroscopes, electric current sensors, and electric voltage sensors.

In some embodiments, an array of sensors is implemented on a device. In some embodiments, the sensors in the array are connected. In some embodiments, two or more sensors in an array are different types and/or shapes, or all sensors are the same type/shape. In some embodiments, three or more sensors in an array are a mix of sensors sharing the same type and/or shape and sensors having different types and/or shapes.

In some applications, where multiple chip designs are employed, it is advantageous to have a chip sandwich where two devices are facing each other, separated by a spacer, to form a flow cell. In various embodiments, devices are run sequentially or in parallel. In some embodiments, multiple chip designs are used to narrow the size range of material collected creating a band pass filter. In some instances, current chip geometry (e.g., 80 um diameter electrodes on 200 um center-center pitch (80/200) acts as 500 bp cutoff filter (e.g., using voltage and frequency conditions around 10 Vpp and 10 kHz). In such instances, a nucleic acid of greater than 500 bp is captured, and a nucleic acid of less than 500 bp is not. Alternate electrode diameter and pitch geometries have different cutoff sizes such that a combination of chips should provide a desired fragment size. In some instances, a 40 um diameter electrode on 100 um center-center pitch (40/100) has a lower cutoff threshold, whereas a 160 um diameter electrode on 400 um center-center pitch (160/400) has a higher cutoff threshold relative to the 80/200 geometry, under similar conditions. In various embodiments, geometries on a single chip or multiple chips are combined to select for a specific sized fragments or particles. For example, when a 600 bp cutoff chip leaves a nucleic acid of less than 600 bp in solution, then that material is optionally recaptured with a 500 bp cutoff chip (which is opposing the 600 bp chip). This leaves a nucleic acid population comprising 500-600 bp in solution. In some embodiments, size selection is accomplished using a single electrode geometry, wherein nucleic acid of >500 bp is isolated on the electrodes, followed by washing, followed by reduction of the ACEK high field strength (change voltage, frequency, conductivity) in order to release nucleic acids of <600 bp, resulting in a supernatant nucleic acid population between 500-600 bp.

In some embodiments, the devices and methods described herein allow for selection of nucleic acids of about 100 bp to about 1,000 bp. In some embodiments, the devices and methods described herein allow for selection of nucleic acids of at least about 100 bp. In some embodiments, the devices and methods described herein allow for selection of nucleic acids of at least about 100 bp, 150 bp, 200 bp, 250 bp, 300 bp, 350 bp, 400 bp, 450 bp, or about 500 bp. In some embodiments, the devices and methods described herein allow for selection of nucleic acids of at most about 1,000 bp. In some embodiments, the devices and methods described herein allow for selection of nucleic acids of at most about 250 bp, 300 bp, 350 bp, 400 bp, 450 bp, 500 bp, 550 bp, 600 bp, 650 bp, 700 bp, 750 bp, 800 bp, 850 bp, 900 bp, 950 bp, or about 1,000 bp. In some embodiments, the devices and methods described herein allow for selection of nucleic acids of about 100 bp to about 150 bp, about 100 bp to about 200 bp, about 100 bp to about 250 bp, about 100 bp to about 300 bp, about 100 bp to about 400 bp, about 100 bp to about 500 bp, about 100 bp to about 600 bp, about 100 bp to about 700 bp, about 100 bp to about 800 bp, about 100 bp to about 900 bp, about 100 bp to about 1,000 bp, about 150 bp to about 200 bp, about 150 bp to about 250 bp, about 150 bp to about 300 bp, about 150 bp to about 400 bp, about 150 bp to about 500 bp, about 150 bp to about 600 bp, about 150 bp to about 700 bp, about 150 bp to about 800 bp, about 150 bp to about 900 bp, about 150 bp to about 1,000 bp, about 200 bp to about 250 bp, about 200 bp to about 300 bp, about 200 bp to about 400 bp, about 200 bp to about 500 bp, about 200 bp to about 600 bp, about 200 bp to about 700 bp, about 200 bp to about 800 bp, about 200 bp to about 900 bp, about 200 bp to about 1,000 bp, about 250 bp to about 300 bp, about 250 bp to about 400 bp, about 250 bp to about 500 bp, about 250 bp to about 600 bp, about 250 bp to about 700 bp, about 250 bp to about 800 bp, about 250 bp to about 900 bp, about 250 bp to about 1,000 bp, about 300 bp to about 400 bp, about 300 bp to about 500 bp, about 300 bp to about 600 bp, about 300 bp to about 700 bp, about 300 bp to about 800 bp, about 300 bp to about 900 bp, about 300 bp to about 1,000 bp, about 400 bp to about 500 bp, about 400 bp to about 600 bp, about 400 bp to about 700 bp, about 400 bp to about 800 bp, about 400 bp to about 900 bp, about 400 bp to about 1,000 bp, about 500 bp to about 600 bp, about 500 bp to about 700 bp, about 500 bp to about 800 bp, about 500 bp to about 900 bp, about 500 bp to about 1,000 bp, about 600 bp to about 700 bp, about 600 bp to about 800 bp, about 600 bp to about 900 bp, about 600 bp to about 1,000 bp, about 700 bp to about 800 bp, about 700 bp to about 900 bp, about 700 bp to about 1,000 bp, about 800 bp to about 900 bp, about 800 bp to about 1,000 bp, or about 900 bp to about 1,000 bp. As described herein, selection of nucleic acids of a certain size or range indicate that at least 70%, 80%, 90%, 95%, or 99% of the selected nucleic acids are within that size or range. As an illustrative example, selection of nucleic acids of about 300 bp to about 600 bp can indicate that about 90% of the nucleic acids are about 300 bp to about 600 bp. In some embodiments, sensor readout is fully multiplexed. In further embodiments, multiplexing is based on rows and/or columns. A multiplexing example is 5 bit by 4 bit—nine control lines and one additional signal line, resulting in a total of ten lines.

In some embodiments, a DEP electrode I/O is advantageously laid out as more than one line.

In some embodiments, a sensor comprises a surface passivation organic layer.

In another embodiment, a destructive sensing method would be to not implement a hydrogel coating on the chip surface, turn on the DEP field, and allow the analytes of interest to burn or denature on the surface of the electrodes (usually the hydrogel layer is there as a protective layer to prevent this very thing from occurring). As these analytes accumulate on the surface of the electrodes, the electrical characteristics of the electrodes (resistance, capacitance, impedance, or a combination thereof) would change, and these changes are measurable by using sense circuitry built into the analyte analysis apparatus. Alternatively, in other embodiments discussed earlier herein, this method looks for a change in impedance/resistance with the hydrogel layer still on the surface of the chip.

In another embodiment, the hydrogel is functionalized with different moieties that can be used for sensing such as RGD peptides for cell adhesion, glucose sensor, ion sensors for water purification, thermally responsive hydrogels for characterization of biochemical reactions. By determining the ionic change in the hydrogel, the rate or levels of activity can be determined.

Digital Processing Device

Figure 5:
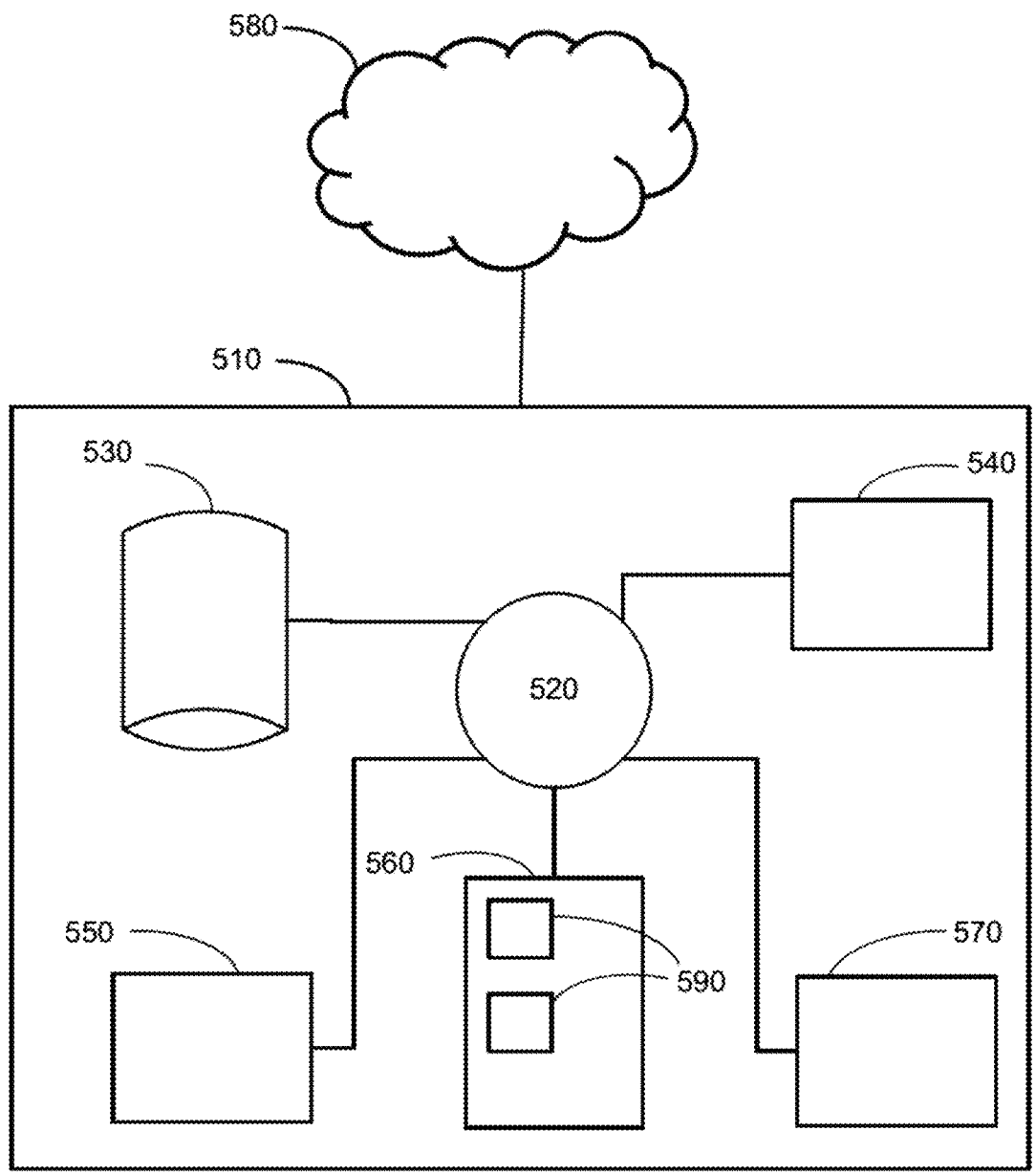
FIG. 5 schematically illustrates a computer control system that is programmed or configured to implement methods provided herein.

In various embodiments, the subject matter described herein include a digital processing device, or use of the same. FIG. 5 shows a digital processing device 510 that is programmed or otherwise configured to carry out executable instructions. In some embodiments, the digital processing device is programmed to select one or more ads and/or one or more questions based on user information and/or setting information. In some embodiments, the digital processing device is an electronic device of a user. In some embodiments, the digital processing device is a computer system that is remotely located with respect to the user (e.g., a remote server). In some embodiments, the digital processing device is a mobile computing device. In further embodiments, the digital processing device includes one or more hardware central processing units (CPU) 520 that carry out the device's functions. In still further embodiments, the digital processing device further comprises an operating system and/or application 560 configured to perform executable instructions. In some embodiments, the operation system or application 560 comprises one or more software modules 590 configured to perform executable instructions (e.g., a data analysis module). In some embodiments, the digital processing device is optionally connected a computer network 580. In further embodiments, the digital processing device is optionally connected to the Internet such that it accesses the World Wide Web. In still further embodiments, the digital processing device is optionally connected to a cloud computing infrastructure. In other embodiments, the digital processing device is optionally connected to an intranet. In other embodiments, the digital processing device is optionally connected to a data storage device.

In accordance with the description herein, suitable digital processing devices include, by way of non-limiting examples, server computers, desktop computers, laptop computers, notebook computers, sub-notebook computers, netbook computers, netpad computers, set-top computers, handheld computers, Internet appliances, mobile smartphones, tablet computers, personal digital assistants, video game consoles, and vehicles. Those of skill in the art will recognize that many smartphones are suitable for use in the system described herein. Non-limiting examples of smartphones include those using mobile operating systems such as Android, iOS, Tizen, Sailfish OS, BlackBerry OS, Windows Mobile, Symbian, Bada, webOS, Palm OS, and Ubuntu Touch. Those of skill in the art will also recognize that select televisions, video players, and digital music players with optional computer network connectivity are suitable for use in the system described herein. Suitable tablet computers include those with booklet, slate, and convertible configurations, known to those of skill in the art.

In some embodiments, the digital processing device includes an operating system 560 configured to perform executable instructions. The operating system is, for example, software, including programs and data, which manages the device's hardware and provides services for execution of applications. Those of skill in the art will recognize that suitable server operating systems include, by way of non-limiting examples, FreeBSD, OpenBSD, NetBSD®, Linux, Apple® Mac OS X Server®, Oracle® Solaris®, Windows Server®, and Novell® NetWare®. Those of skill in the art will recognize that suitable personal computer operating systems include, by way of non-limiting examples, Microsoft® Windows®, Apple® Mac OS X®, UNIX®, and UNIX-like operating systems such as GNU/Linux®. In some embodiments, the operating system is provided by cloud computing.

In some embodiments, the device includes a storage 530 and/or memory device 550. The storage and/or memory device is one or more physical apparatuses used to store data or programs on a temporary or permanent basis. In some embodiments, the device is volatile memory and requires power to maintain stored information. In some embodiments, the device is non-volatile memory and retains stored information when the digital processing device is not powered. In further embodiments, the non-volatile memory comprises flash memory. In some embodiments, the non-volatile memory comprises dynamic random-access memory (DRAM). In some embodiments, the non-volatile memory comprises ferroelectric random access memory (FRAM). In some embodiments, the non-volatile memory comprises phase-change random access memory (PRAM). In other embodiments, the device is a storage device including, by way of non-limiting examples, CD-ROMs, DVDs, flash memory devices, magnetic disk drives, magnetic tapes drives, optical disk drives, and cloud computing based storage. In further embodiments, the storage and/or memory device is a combination of devices such as those disclosed herein.

In some embodiments, the digital processing device includes a display 540 to send visual information to a user. In some embodiments, the display is a cathode ray tube (CRT). In some embodiments, the display is a liquid crystal display (LCD). In further embodiments, the display is a thin film transistor liquid crystal display (TFT-LCD). In some embodiments, the display is an organic light emitting diode (OLED) display. In various further embodiments, on OLED display is a passive-matrix OLED (PMOLED) or active-matrix OLED (AMOLED) display. In some embodiments, the display is a plasma display. In other embodiments, the display is a video projector. In some embodiments, the display is a touchscreen. In still further embodiments, the display is a combination of devices such as those disclosed herein.

In some embodiments, the digital processing device includes an interface 570 for interacting with and/or receiving information from a user. In some embodiments, the interface comprises a touchscreen. In some embodiments, the interface comprises an input device. In some embodiments, the input device is a keyboard. In some embodiments, the input device is a pointing device including, by way of non-limiting examples, a mouse, trackball, track pad, joystick, game controller, or stylus. In some embodiments, the input device is a touch screen or a multi-touch screen. In other embodiments, the input device is a microphone to capture voice or other sound input. In other embodiments, the input device is a camera or video camera to capture motion or visual input. In still further embodiments, the input device is a combination of devices such as those disclosed herein.

In some embodiments, user data (e.g. user profile, user information, and analyte analysis) stored in the digital processing device is encrypted. In some embodiments, third party applications are blocked from accessing private information stored on the digital processing device.

User Interface

In various embodiments, the subject matter herein includes a user interface for an individual to input information and select analytes to be tested as well as to receive the results of the assay.

In various embodiments, a user interface comprises one or more interface elements allowing a user to interact with devices, apparatuses, or systems described herein. In various embodiments, the user interface comprises physical interactive elements such as hard buttons (e.g., physically tangible buttons), knobs, sliders, switches, a keypad, microphones, and/or cameras. In some embodiments, physical interactive elements provide haptic or tactile feedback in response to a touch action. In various embodiments, a user interface comprises a display. In some embodiments, the display is a touchscreen such as a resistive touchscreen or a capacitive touchscreen. In some embodiments, a touchscreen comprises one or more soft interface elements. In some embodiments, a soft interface element on the touchscreen is a soft button or icon for receiving user input or instructions. In some embodiments, a touchscreen provides haptic or tactile feedback in response to a touch action on the touchscreen. In some embodiments, the interface provides a selection of assays or tests for the user to select. In some embodiments, the interface displays a time to completion for a selected assay or test. In some embodiments, the interface displays a selection of ads for a user to select for viewing. In some embodiments, the display 540 is part of the interface 570.

In some embodiments, the interface comprises a security protocol to prevent unauthorized access to user information. In some embodiments, the interface requires user authentication before allowing a user to view results of an analyte analysis. In some embodiments, the interface requires user authentication before allowing a user to open an analyte analysis program. In some embodiments, user information is encrypted and requires user authentication to be decrypted. In some embodiments, user authentication is provided via at least one of biometric authentication (e.g. fingerprint scanner, retina scanner), password authentication, and security question authentication.

In some embodiments, the interface is a web portal allowing user access to information. In some embodiments, the web portal comprises HIPAA-compliant security protocols to protect user information. In some embodiments, the web portal enables a user to track information specific to the user. In some embodiments, the web portal enables an authorized user to track information not specific to the user (e.g. a doctor authorized to track information for his patient).

Non-Transitory Computer Readable Storage Medium

In various embodiments, the subject matter disclosed herein include one or more non-transitory computer readable storage media encoded with a program including instructions executable by the operating system of an optionally networked digital processing device. In further embodiments, a computer readable storage medium is a tangible component of a digital processing device. In still further embodiments, a computer readable storage medium is optionally removable from a digital processing device. In some embodiments, a computer readable storage medium includes, by way of non-limiting examples, CD-ROMs, DVDs, flash memory devices, solid state memory, magnetic disk drives, magnetic tape drives, optical disk drives, cloud computing systems and services, and the like. In some cases, the program and instructions are permanently, substantially permanently, semi-permanently, or non-transitorily encoded on the media.

Computer Program

In various embodiments, the subject matter disclosed herein include at least one computer program, or use of the same. A computer program includes a sequence of instructions, executable in the digital processing device's CPU, written to perform a specified task. Computer readable instructions may be implemented as program modules, such as functions, objects, Application Programming Interfaces (APIs), data structures, and the like, that perform particular tasks or implement particular abstract data types. In light of the disclosure provided herein, those of skill in the art will recognize that a computer program may be written in various versions of various languages.

The functionality of the computer readable instructions may be combined or distributed as desired in various environments. In some embodiments, a computer program comprises one sequence of instructions. In some embodiments, a computer program comprises a plurality of sequences of instructions. In some embodiments, a computer program is provided from one location. In other embodiments, a computer program is provided from a plurality of locations. In various embodiments, a computer program includes one or more software modules. In various embodiments, a computer program includes, in part or in whole, one or more web applications, one or more mobile applications, one or more standalone applications, one or more web browser plug-ins, extensions, add-ins, or add-ons, or combinations thereof.

In some implementations, analyte analysis apparatuses herein are controlled by a user using a computer program on a digital processing device, such as a phone, tablet, or laptop computer. Computer programs for analyte analysis apparatuses are also capable of performing analysis of the output data.

In some embodiments, a computer program comprises a software module comprising a data analysis module configured to analyze signals of an assayed biological sample. In further embodiments, analyzing the signals comprises a use of a statistical analysis. In some cases, analyzing the signals comprises comparing the signals with a signal template. There are various analyses, which can be combined to assemble an analysis module in the computer program. Examples of analyzing the signals include: analyzing strength of the signals, analyzing a frequency of the signals, identifying a spatial distribution pattern of the signals, identifying a temporal pattern of the one or more signals, detecting a discrete fluctuation in the signals corresponding to a chemical reaction event, inferring a pressure level, inferring a temperature level, inferring a light intensity, inferring a color intensity, inferring a conductance level, inferring an impedance level, analyzing patterns of one or more AC electrokinetic high field regions and one or more AC electrokinetic low field regions, and analyzing a chemical reaction event. In still further embodiments, a chemical reaction event comprises one or more of the following: a molecular synthesis, a molecular destruction, a molecular breakdown, a molecular insertion, a molecular separation, a molecular rotation, a molecular spinning, a molecular extension, a molecular hybridization, a molecular transcription, a sequencing reaction, and a thermal cycling. In some embodiments, a computer program comprises a software module presenting a result obtained by the data analysis module on a display of a digital processing device. In some embodiments, a computer program comprises a software module providing an interface to allow upload of a result to an online database. In some embodiments, a computer module comprises a software module providing a query interface allowing search of the online database.

User Information, Ads, and Questions

In some embodiments, the systems and methods described herein comprise a software module for collecting user information to develop a user profile. In some embodiments, user information comprises one or more of a user name, a user ethnic background, a user age, a user height, a user weight, a user body fat percentage, medical history, and other medical information, such as a diagnosis and one or more symptoms. In some embodiments, medical information includes one or more of a diagnosis, past or present treatment regimen (e.g., dosage, frequency, duration, etc) and outcome, past and/or present symptoms, genetic profile (including elevated risk associations with certain diseases), family history of illness, drug or other allergies, blood type, past injuries or illnesses, surgery, past and/or current medication, mental health history, and information pertaining to adherence to treatment regimen (e.g., pharmacy records indicating whether user regularly refills prescription, self-reporting, physician reports, electronic recordings, and blood or urine assays). In some embodiments, the user profile includes price information for drug(s). In some embodiments, price information for drug(s) is obtained from the user (e.g., during setup of the user profile and/or via question(s) presented to the user during analyte analysis). In some embodiments, user information comprises non-medical information such as one or more of user home address, user zip code, user income, user family income, user job sector, user job function, any owned or operated business, type of business, number of employees, size and location(s) of the business, user credit rating, user insurance coverage (e.g., health insurance, home insurance, vehicle insurance, life insurance, etc.), education (e.g., degrees, licenses, credentials, or certifications), marital status, number and/or age of children, language(s), information on relatives of the user (e.g., relationship with user, location, marital status, number and/or age of children, or degree of contact), user interest in various topics (e.g., entertainment, movies, sports, automobiles, politics, economics, health, law, education, science, or technology), user brand preferences, user spending information (e.g., amount spent on traveling, food, entertainment, and/or clothing in the past year), and social media information (e.g., Twitter handle, Facebook profile, user preference settings in social media). In some embodiments, user information is obtained through one or more methods as described herein such as, for example, presenting questions to the user or accessing user information from the digital processing device. In some embodiments, user information is obtained by accessing publicly available information. Publicly available information can include type of home and price (e.g., based on latest recorded sale obtained from a county recorder), social media postings, marriage and/or divorce records, warrants and/or arrests, court cases, obituaries, immigration records, professional licensing records, and business licenses.

In some embodiments, the systems and methods described herein comprise a software module for geo-tagging an analyte analysis result with a current location of the digital processing device where the analyte analysis takes place. In some embodiments, the location of the digital processing device is obtained without geo-tagging the analyte analysis. In some embodiments, the location is a real-time location. As used herein, geo-tagging refers to the process of adding geographical identification metadata. For example, in some embodiments, a geo-tagged analyte analysis comprises geographical location metadata indicating the analyte analysis was carried out in a certain geographic location. In some embodiments, the geographic location comprises one or more of a continent, a nation, a state, a province, a territory, an island, a city/town/village, an address, and coordinates (e.g. longitude and latitude). In some embodiments, the geographic location is a specific location or an area around a location. In some embodiments, a result (e.g. of an analyte analysis) is time-stamped. For example, an analyte analysis that is performed is optionally time-stamped with the date and/or time when the result was generated.

In some embodiments, the systems and methods described herein comprise an online database. In some embodiments, the online database stores information for an individual (e.g. test or analyte analysis results, user profile, etc). In some embodiments, the online database obtains information for an individual from the social network or other online community. In some embodiments, the online database provides information for the individual to the social network or other online community. In some embodiments, an online database interface allows an individual or user to transfer information between the online database and the social network or online community. For example, in some embodiments, an individual posts a clean test result stored on the online database on a social network. In some embodiments, the online database comprises a social network or other online community.

In some embodiments, the systems and methods described herein comprise a software module for obtaining usage statistics (e.g. operating system, cellular network, Wi-Fi network) from the digital processing device. In some embodiments, the software module obtains usage statistics for one or more of email use, web browsing, video streaming, web searching, app usage, online shopping, ad views, and ad clicks. In some embodiments, usage statistics are shared with a third party such as, for example, a pharmaceutical company.

Figure 3:
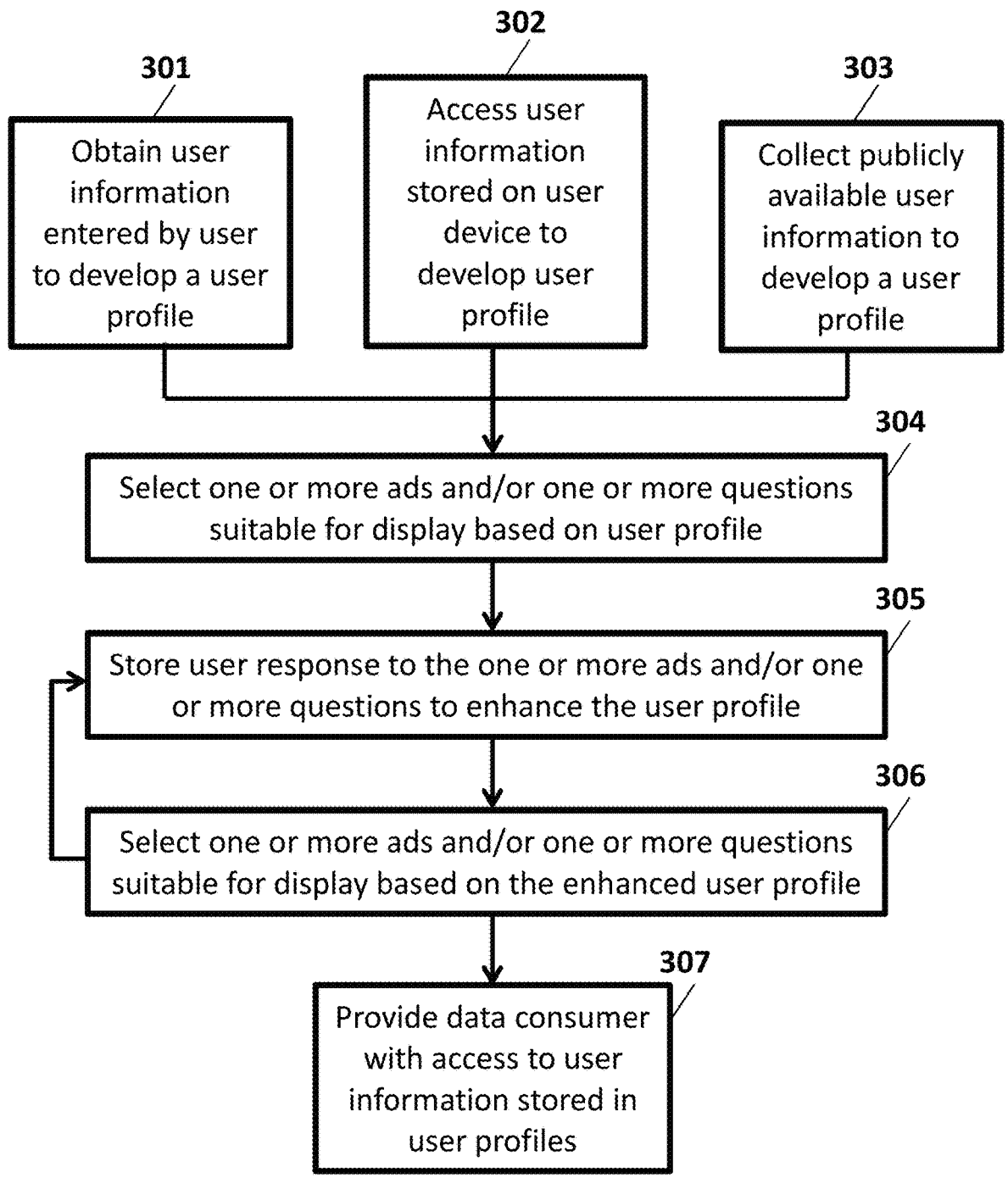
FIG. 3 illustrates an example ad and/or question selection flow chart.

FIG. 3 provides an illustrative flow chart of one process for selecting ads and/or questions suitable for presenting to a user. In some embodiments, a user profile is developed using information entered by a user 301 (e.g., when a user first sets up a profile). A user profile is developed using information obtained from the digital processing device of the user 302. For example, in some embodiments, information stored on the device is accessed after obtaining authorization from the user to access one or more of a contact list, browsing history, social media, email, text messages, or other user information on the digital processing device. In further embodiments, a user optionally chooses to authorize access in place of being presented with one or more ads and/or one or more questions in association with a result (e.g., a dielectrophoresis-based test result). In further embodiments, authorization to access user information is limited to meta-data and/or non-identifying information. In some embodiments, user information is obtained from publicly available information such as a social media profile and public postings by the user. In some embodiments, a user profile is developed using publicly available information about the user 303.

Figure 6A:
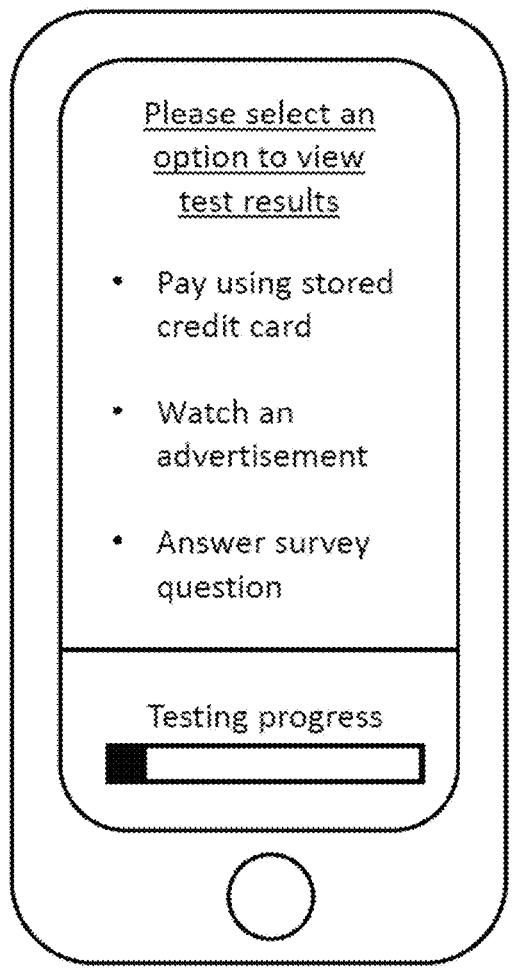
FIG. 6A illustrates an exemplary display of an electronic device showing options for viewing a test result.
Figure 6B:
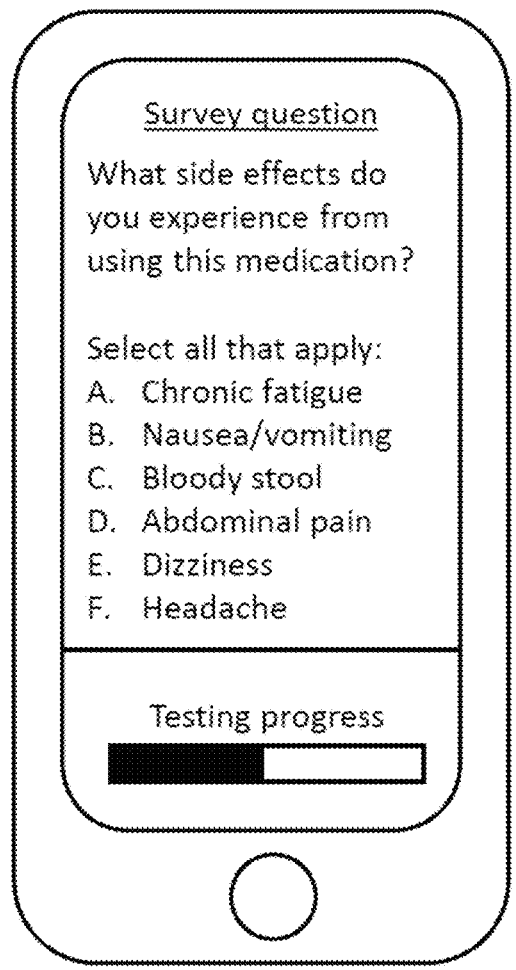
FIG. 6B illustrates an exemplary display of an electronic device showing a survey question presented in association with a test result.
Figure 6C:
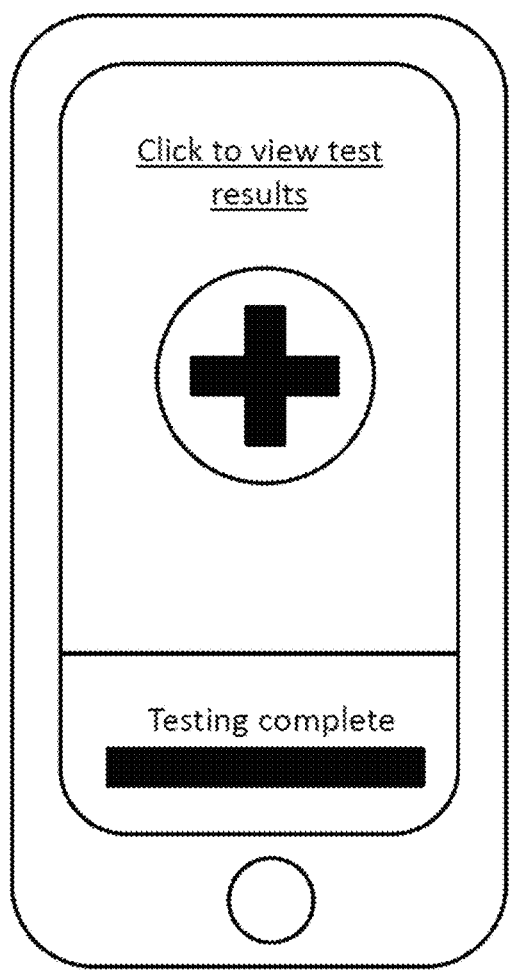
FIG. 6C illustrates an exemplary display of an electronic device allowing a user to view the results of a completed test.
Figure 6D:
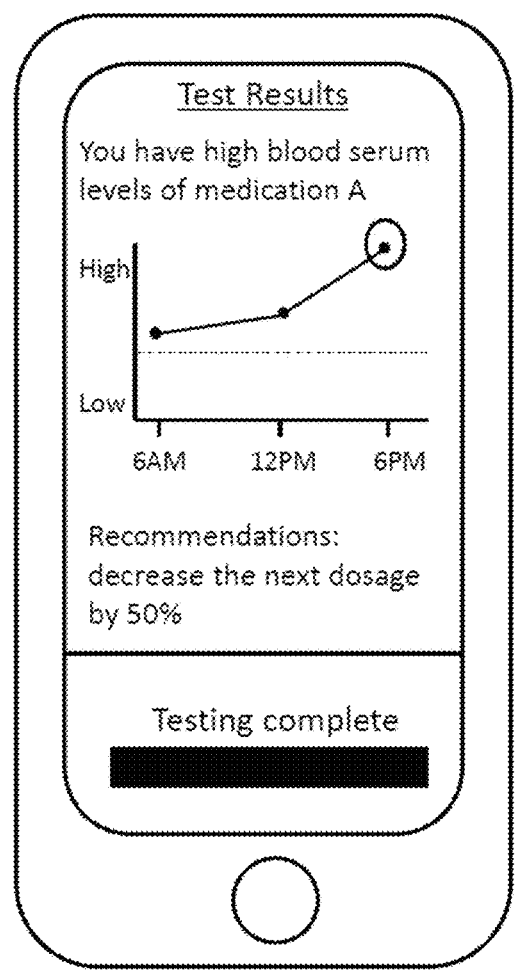
FIG. 6D illustrates an exemplary display of an electronic device showing the results of a completed test and an accompanying recommendation.
Figure 6E:
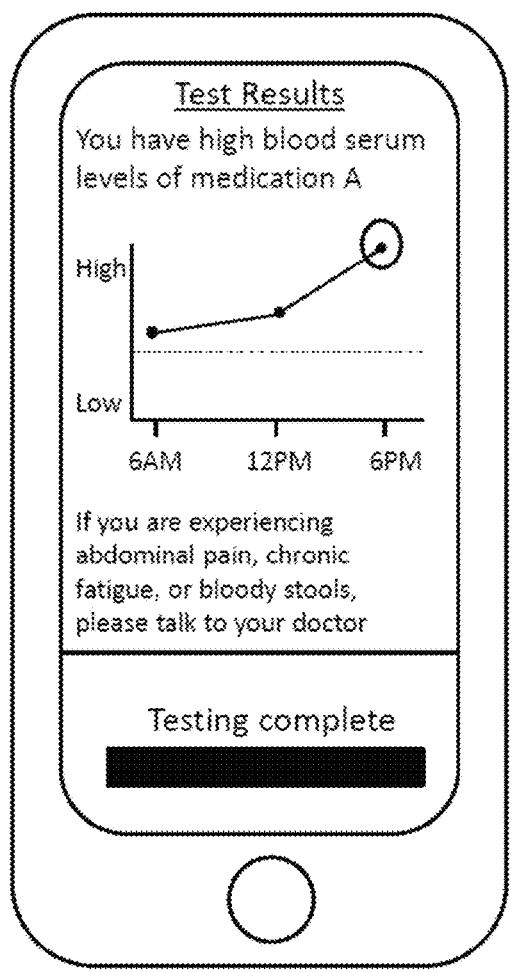
FIG. 6E illustrates another exemplary display of an electronic device showing the results of a completed test and an accompanying recommendation.

In some embodiments, a user is presented with one or more ads in association with an assay or test (e.g., the user has to watch one or more ads in order to obtain a test result generated using the systems or methods described herein). In other embodiments, a user is presented with one or more questions to be answered in association with an assay or test. In some embodiments, a user chooses between watching one or more ads and answering one or more questions in association with an assay or test. In some embodiments, the result of the assay or test is locked until the user watches one or more ads or answers one or more questions presented in association with the assay or test. In some embodiments, the user has a choice of watching one or more ads, answering one or more survey questions, or paying for the assay or test. In some embodiments, the user makes this choice when configuring a user profile. In some embodiments, a user is presented with one or more ads and one or more questions in association with an assay or test. FIGS. 6A-6F illustrate an exemplar embodiment of the process by which a user utilizes the systems and devices described herein to execute analyte testing and view the test results. An exemplary embodiment of an application interface or display of an electronic device is shown in FIG. 6A in which the user is presented with several options for viewing the test result. Once the user makes his choice, the display may then show the selected choice such as the exemplary survey question shown in FIG. 6B. In some cases, testing progress may be indicated such as by a progress bar as shown. After the user has made a choice and viewed or answered the ad or question, respectively, the device may allow the user to view the test results (FIG. 6C). The optional recommendations accompanying the test results may vary (e.g. depending on user profile, past treatment information, etc) such as shown in FIGS. 6D and 6E. Finally, the user may choose from various options in a software application or web portal such as the health portal shown in FIG. 6F. The health portal may provide options to perform a test, view or configure the user profile, view testing history (time and results of previous tests), data sharing, search, ask anything, and settings. In various embodiments, the health portal allows the user to conduct testing such as by the analyte analysis apparatuses described herein. The data sharing option can allow a user to give authorization to other entities or persons such as healthcare providers or third parties to view certain health data. In some cases, the search option allows a user to search through his or her test results, identify healthcare providers, find treatment options, and obtain other relevant information. The "ask anything" option may leverage the algorithms described herein to address user queries such as, for example, utilizing a machine learning algorithm to identify a suggested treatment based on the user profile, past treatment history, and treatment availability. The settings may be used to setup user preferences (e.g. whether to pay, view an ad, or answer a survey question in order to view test results).

The one or more ads and one or more questions can be presented at different stages during the assay or test. For example, in some embodiments, a user is presented with an ad while the assay or test is running, and then presented with a question in order to unlock the result for viewing. In various embodiments, the one or more ads or one or more questions are selected as suitable for presenting to the user 304. In some embodiments, suitable ads and/or questions are selected based on how the ads/questions (or setting information for said ads/questions) match up with the user profile as described throughout this application. In some embodiments, the user response to the ads and/or questions is stored and used to further develop the user profile 305. For example, a negative response to a question of whether the user likes horror movies can be added to the user profile to screen out the user from receiving ads for horror movies in the future. As another example, a user's decision to select a movie ad in order to view an extended trailer associated with the ad is stored as an indication of user interest in that movie, the movie genre, the director, the actor(s), or other aspects of the movie. Accordingly, the next selection of suitable ads or questions will be based on the user profile enhanced with this additional information 306. In some embodiments, the process of selecting suitable ads and/or questions to be displayed to a user and then enhancing the user profile with the responses is an iterative process that is further enhanced as additional information about the user is obtained with each cycle (305, 306). In various embodiments, the systems and methods described herein provide data consumers with access to the plurality of user profiles and/or the information they contain 307. In some embodiments, one or more ads comprise at least 1, 2, 3, 4, 5, 6, 7, 8, 9, or 10 or more ads. In some embodiments, one or more ads comprise no more than 1, 2, 3, 4, 5, 6, 7, 8, 9, or 10 or more ads. In some embodiments, one or more ads comprise between 1 and 5, 2 and 6, 3 and 7, 4 and 8, 5 and 9, or 6 and 10 ads. In some embodiments, one or more questions comprise at least 1, 2, 3, 4, 5, 6, 7, 8, 9, or 10 or more questions. In some embodiments, one or more questions comprise no more than 1, 2, 3, 4, 5, 6, 7, 8, 9, or 10 or more questions. In some embodiments, one or more questions comprise between 1 and 5, 2 and 6, 3 and 7, 4 and 8, 5 and 9, or 6 and 10 questions.

In some embodiments, one or more questions presented to a user are configured to obtain additional health information. In some embodiments, one or more questions presented to a user are configured to obtain additional non-health information. In some embodiments, the questions are based on user information and/or test results. In some embodiments, the questions are configured as multiple choice questions, fill in the blank, true or false, binary choice, short answer, matching, preference rankings, or other format. In some embodiments, a user is asked one or more questions of varying question types (and sometimes in combination with ads) in a progression over time as the user repeatedly uses the systems or devices described herein. As an illustrative example, a user is presented with a binary question on whether he or she is interested in movies in order to access the first test result. If the user answers yes, then the next question during a second test asks the user to rank a preference for movie genres from highest to lowest for action, romantic, drama, comedy, and horror. Based on these choices, during the third test, the user is presented with an ad for an upcoming movie release in the user's highest rated movie genre. In some embodiments, a user is presented with a choice between different ads to view. In some embodiments, the choice includes a description of each ad. In some embodiments, a user is presented with a choice between one or more ads or questions. As an illustrative example, a user is presented with a choice between watching an ad for a drug or an ad for a car and answering a question about his sports preference. As another example, a user is presented with a first question asking whether the user is taking a particular medication, and if the user answers in the affirmative, a second question is presented asking the price of the medication. In some embodiments, one or more ads are presented to a user based on a disease/condition and/or treatment (e.g. provided by a user during user profile setup or answered in a question). For example, in some embodiments, ads for a group of drugs commonly administered together as part of a chemotherapeutic treatment regimen are presented to a user who indicated he was just diagnosed with cancer. In some embodiments, an ad comprises clinical trial information and is presented to a user whose user profile information makes the user an eligible clinical trial participant.

In some embodiments, user profile information is used to enhance treatment. For example, in some embodiments, user blood type is used to identify potential organ donors for a user suffering from or at risk for organ failure.

In some embodiments, one or more ads or questions are presented to a user of the digital processing device based on the location of the device. For example, a user uses a digital processing device and an analyte analysis apparatus described herein to perform an analyte analysis of a biological material of an individual (in this case, the user himself). The analyte analysis is geo-tagged with the location of the user and his device based on GPS and/or Wi-Fi triangulation data obtained from the device. The geo-tagged analyte analysis is then uploaded to a database comprising a plurality of geo-tagged analyte analyses. In some embodiments, the database is accessible to an authorized user. For example, in some embodiments, an authorized user is a governmental organization such as the CDC, a non-governmental organization, an epidemiologist, a researcher or research institution, or a drug company. In some embodiments, the authorized user uses the geo-tagged analyte analyses to determine changes to a disease, demand for a drug or treatment, spread of a disease, and/or identify a need for aid in a geographic location.

In some embodiments, the location of the device/user is used to select ad(s) and/or question(s) to present to a user. In some embodiments, the location is matched against one or more ads or questions to determine relevant ads or questions. For example, a user uses a digital processing device and an analyte analysis apparatus described herein to perform an analyte analysis of a biological material. The device determines its location and provides the location to a remote server. The remote server then compares the location against a database of ads/questions to select one or more ads or questions to present to the user. In this example, the user is located in a particular geographic region known for having a high UV index. Accordingly, the remote server selects an ad for sunscreen and an ad for UV-protecting rash guards for the digital processing device to present to the user. In some embodiments, an algorithm automatically selects one or more ads or questions based on location of the device without requiring human input.

In some embodiments, an ad is targeted to a category or demographic. In some embodiments, a demographic comprises one or more of an age range, a gender, an ethnicity, a nationality, household income, geographic location, home ownership, disabilities, education, employment status, health status (e.g. cancer diagnosis), children, type of car(s), marital status, and credit rating. In some embodiments, an ad is targeted to a healthy demographic (e.g. lacking a particular disease diagnosis). In some embodiments, an ad for cancer screening and/or detection is targeted to a healthy demographic.

In some embodiments, user information obtained using the systems and methods described herein is used to build a user profile (as used herein, user profile encompasses provider profile, which is a type of user profile limited to healthcare providers). In some embodiments, a plurality of user profiles is stored on one or more databases accessible by a data consumer. In some embodiments, a data consumer is a user (e.g., person who is getting tested), a physician, a nurse, a healthcare worker, a pharmaceutical company, an advertiser, a researcher or research group, a university, a government agency, or other individual or organization. In some embodiments, a data consumer pays for access to the user and/or provider profiles. In some embodiments, a data consumer is authorized to access user/provider profiles and/or data associated with said profiles. For example, data associated with said profiles can include metadata (e.g. timing/frequency of certain tests performed by diagnostic devices). In some embodiments, a data consumer agrees to view one or more ads and/or answer one or more questions in exchange for accessing user profiles. In some embodiments, the systems and methods described herein comprise a software module for processing and curating the user information and/or user profiles so that they allow searching and/or filtering of data by data consumers. In some embodiments, user profiles are anonymized to remove identifying information and/or presented to data consumers in accordance with HIPAA requirements (e.g., the "limited health data" described elsewhere herein). In some embodiments, data consumers are divided into paying and non-paying data consumers based on their classification. For example, in some embodiments, a pharmaceutical company or large organization pays to obtain access, while individuals (e.g., a user utilizing the systems and methods herein to obtain test results) view ads and/or answer questions to obtain access to the information. In some embodiments, the user profile comprises health information relevant to a data consumer such as, for example, a pharmaceutical company. As an illustrative example, a pharmaceutical company looking for ideal participants in a clinical trial for a new breast cancer drug screens the plurality of anonymized user profiles to select for early stage breast cancer patients between the ages of 20 and 35 who do not smoke and are indicated as having high adherence to treatment regimen (e.g., based on pharmacy refill records for a past treatment regimen). The company then is able to send an anonymized message (i.e., company does not know identities of the recipients) to eligible candidates inviting them to participate in the clinical trial. In some embodiments, the message comprises one or more questions presented to each user. Alternatively, in another example, a pharmaceutical company is interested in marketing a complementary therapy for users being treated for a particular illness or condition. Accordingly, the pharmaceutical company screens user profiles for users who are currently being treated for the illness or condition and have indicated (e.g., by answering questions) a willingness to try complementary therapies with certain benefits such as, for example, mitigating side effects of their main treatment regimen. The company then targets ads for complementary therapies to this group of users using the systems and methods described herein.

In some embodiments, a user profile comprises non-health information that is useful to an advertiser. As an illustrative example, a mortgage company wants to target home mortgage re-financing ads to users who have recently bought a home. First, the mortgage company screens the user profiles for users who have purchased a home in the past five years. This information is obtained either from the user directly answering the question or from public records such as, for example, obtaining purchase records for the property located at the user's home address. The mortgage company further screens for users who exceed a minimum income threshold or other factors relevant to suitability for home mortgage re-financing. The company then targets home mortgage re-financing ads to this user group.

In some embodiments, the systems and methods described herein comprise a software module soliciting and/or receiving user feedback on the performance or accuracy of the analyte analysis. In some embodiments, user feedback is used in product development to improve performance of the systems and methods for performing analyte analysis.

In some embodiments, advertisers or third-party party ad networks provide one or more ads to be presented to one or more users. In some embodiments, the ads are targeted ads generated based on user information from user profiles. In some embodiments, advertisers provide one or more questions to be presented to one or more users. In some embodiments, the one or more questions presented to users are from surveys. In some embodiments, a survey is broken up into separate rounds of questions presented to users over time. As an illustrative example, a survey of 6 questions are divided into groups of one or more questions that are presented each time a user answers questions in association with the assay or test. In some embodiments, surveys are market description surveys, market profiling surveys, tracking surveys, purchase analysis surveys, customer expectation surveys, new product concept surveys, brand equity surveys, habits and uses surveys, or other surveys.

In some embodiments, a computer program comprises a software module that selects one or more ads from a population of ads. In some embodiments, the selected ad is presented in association with the result obtained by the data analysis module. In some embodiments, the selected ad is presented prior to the performance of an assay or test. In some embodiments, the selected ad is presented during the performance of an assay or test. In some embodiments, the selected ad is presented during a data analysis step to obtain a result by the data analysis module. In some embodiments, the ad is selected based on the individual. For example, in some embodiments, the selected ad is targeted based on user information for the individual (e.g., an ad for a local sports team based on the individual's address). In some embodiments, the ad is selected based on the analyte. For example, an ad for genome sequencing is selected that includes sequencing a gene associated with the analyte. In some embodiments, the ad is selected based on the result. As an illustrative example, a health insurance ad is selected when the result is a positive indication for a biomarker associated with an illness. In some embodiments, the ad is presented on a display of a digital processing device. In some embodiments, the ad is provided by one or more third-party ad networks.

Figure 4:
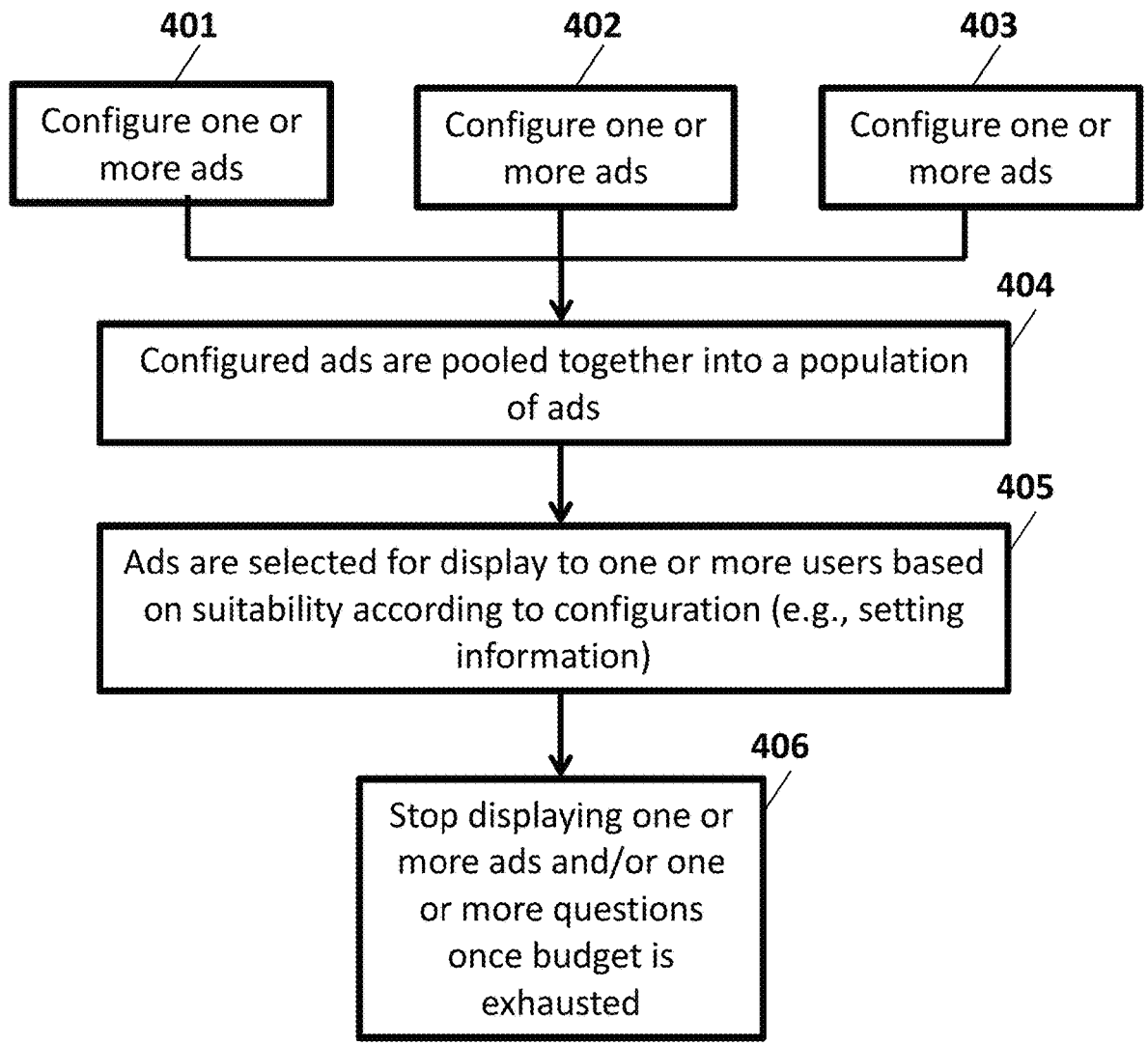
FIG. 4 illustrates an example ad selection flow chart.

FIG. 4 shows an illustrative embodiment of a process by which advertisers configure ads to be displayed to users. In some embodiments, a population of ads comprises ads configured by one or more third-party ad networks (401, 402, 403). In some embodiments, third-party ad networks are advertisers or advertising agencies. In some embodiments, advertisers configure one or more ads with a certain budget (e.g., a certain number of ad displays at a certain rate per view and/or rate per click). In some embodiments, an ad is configured with various information settings by the third-party ad network. In some embodiments, information settings include one or more of advertising type (e.g., product, service, and/or informational), payment (price or free), product, or service type (e.g., medication, entertainment, counseling, etc.). In some embodiments, information settings include one or more advertiser preferences such as, for example, target demographic information such as age, gender, ethnicity, nationality, income, occupation, marital status, and other user information as described elsewhere herein. In some embodiments, an advertiser selects the target population of user profiles to be presented with an ad (e.g., by filtering the plurality of user profiles to arrive at a defined target group of users). In other embodiments, an advertiser selects advertiser preferences, and the ads are displayed to users based on said preferences without being limited to a pre-defined user group. As an illustrative example, an advertiser preference specifies that an ad is to be displayed to users who fit a certain target demographic profile or who select the ad when presented with two or more choices. The configured ads are then pooled together into a population of ads 404. In some embodiments, as users begin to use the systems and methods described herein, configured ads are selected as suitable for display based on user profile and the ad information 405 (e.g., advertiser preferences, setting information, ad content, etc.). In some embodiments, configured ads are no longer selected once the associated advertising budget is depleted 406.

In some embodiments, one or more ads are selected based on user information. In some embodiments, the ads are selected by matching advertiser-configured information settings for the ads against user information. In some embodiments, the systems and methods described herein comprise a software module for performing cohort analysis or behavioral analytics on the plurality of user profiles stored on one or more databases. In some embodiments, cohort analysis comprises dividing the plurality of user profiles into groups or cohorts based on common user information shared between members of each cohort (e.g., a cohort of cancer patients who have stage I colon cancer). In some embodiments, cohort analysis is used to help advertisers or data consumers better understand user behavior. As an illustrative example, a pharmaceutical company looking for participants in a clinical trial for a cancer treatment does not have access to a sufficiently large set of user profiles with information on adherence to treatment regimen. In this example, the treatment has a strict dosage and schedule that must be adhered to in order to result in a positive outcome. Thus, the pharmaceutical company uses the systems and methods described herein to perform cohort analysis using the cohort of users who do have information on adherence to treatment regimen to identify factors relevant to adherence. The company discovers that certain user information correlates with adherence to treatment regimen and is therefore able to use that information to identify more potential clinical trial participants.

In some embodiments, an ad comprises a data link (e.g., an Internet link) to additional content (e.g., a YouTube video, a product website, or an online store). In some embodiments, an ad is optionally selectable to cause the digital processing device to access additional content. In various embodiments, the systems and methods described herein comprise a software module for storing information on selection and/or non-selection of ads by a user. In some embodiments, the information is analyzed to estimate responsiveness of the user to ads in general or to certain ad categories. In some embodiments, user responsiveness is then used to enhance future targeted ads. For example, a user who frequently selects movie ads (e.g., clicks on the ad) will be directed to additional content such as the movie website or an extended trailer is assigned a high movie ad responsiveness score (e.g., as a percentile amongst the plurality of user profiles). As a result, some movie advertisers choose to target movie ads to users in the top 50% of movie ad responsiveness out of the plurality of user profiles.

In some embodiments, one or more of the result, the individual, and the analyte is transmitted to a server or a database, where an ad is selected from a population of ads provided by one or more third-party ad networks. The ad is then configured by selecting one or more ad content file(s) (e.g., text file, graphics file, video file, and interactive file). In some embodiments, the ad content file is selected based on user profiles. For example, in the plurality of user profiles, some users have a preference for watching video ads, while other users have a preference for graphics files. Accordingly, in some embodiments, an ad for the same product or service is shown to different users using different content catered to the individual preference of each user. In some embodiments, these preferences are determined using user information from questions answered in association with a test or assay. Alternatively, in some embodiments, these preferences are determined by analyzing user responsiveness to various ad types. For example, in some embodiments, a user who predominantly (e.g., at least 50%, 60%, 70%, 80% or 90%) interacts with video file ads is determined to prefer video content files to other forms of content files.

Many types of ad content files are suitable. In some embodiments, suitable ad content files include text, documents, e-books, audio, images (e.g., photographs, illustrations, etc.), videos, multimedia (e.g., interactive elements, games, etc.), or combinations of the same.

Many text formats are suitable including, by way of non-limiting examples, Rich Text Format (RTF), TXT, ASCII, UTF-8, and HTML formatted text. Many document formats are suitable including, by way of non-limiting examples, Microsoft® Office Word®, Microsoft® Office PowerPoint®, Microsoft® Office Excel®, DocBook, HTML, OpenDocument, PalmDoc, Portable Document Format (PDF), Rich Text Format (RTF), and WordPerfect.

Many e-book formats are suitable including, by way of non-limiting examples, plain text, hypertext markup language (HTML), Amazon® Kindle™, Open Electronic Package, TomeRaider, Arghos Diffusion, Flip Books, ANSI/NISO Z39.86 (DAISY), FictionBook, Text Encoding Initiative, Plucker, Compressed HM, Portable Document Format, PostScript, DjVu, Microsoft LIT, eReader, Desktop Author, Newton eBook, Founder Electronics, Libris, Mobipocket, EPUB, Broadband eBooks (BBeB), SSReader, TealDoc, IEC 62448, and Comic Book Archive file. Suitable e-books include those formatted for viewing on, by way of non-limiting examples, Apple® iPad®, Amazon® Kindle™, Barnes & Noble Nook™, Sony® Reader™, iRex iLiad, the Jinke Hanlin eReader, Bookeen CyBook, Endless Ideas BeBook, and the Kobo™ eReader.

Many audio formats are suitable including, by way of non-limiting examples, MP3, WAV, AIFF, AU, Apple® Lossless, MPEG-4, Windows Media®, Vorbis, AAC, and Real Audio®.

Many raster image formats are suitable including, by way of non-limiting examples, Joint Photographic Experts Group (JPEG), JPEG 2000, Exchangeable image file format (EXIF), Tagged Image File Format (TIFF), RAW, Portable Network Graphics (PNG), Graphics Interchange Format (GIF), Windows® bitmap (BMP), portable pixmap (PPM), portable graymap (PGM), portable bitmap file format (PBM), wireless bitmap (WBMP), and WebP. In some embodiments, images are uncompressed (e.g., RAW format). In other embodiments, images are compressed. Both lossy and lossless image CODECs are suitable. Many vector image formats are suitable including, by way of non-limiting examples, CGM and SWF. Both two-dimensional and three-dimensional vector images are suitable.

Many video formats are suitable including, by way of non-limiting examples, Windows® Media Video (WMV), Windows® Media®, Motion Picture Experts Group (MPEG), Audio Video Interleave (AVI), Apple® QuickTime®, RealMedia®, Flash Video, Motion JPEG (M-JPEG), WebM, and Advanced Video Coding High Definition (AVCHD). In some embodiments, video is uncompressed (e.g., RAW format). In other embodiments, video is compressed. Both lossy and lossless video CODECs are suitable including, by way of non-limiting examples, DivX™, Cineform, Cinepak, Dirac, DV, FFV1, H.263, H.264, H.264 lossless, JPEG 2000, MPEG-1, MPEG-2, MPEG-4, On2 Technologies (VP5, VP6, VP7, and VP8), RealVideo, Snow lossless, Sorenson Video, Theora, and Windows Media Video (WMV).

In some embodiments, image and/or video media are standard-definition. In other embodiments, image and/or video media are high-definition. In further embodiments, a high-definition image or video frame includes at least 1280× about 720 pixels or at least 1920× about 1080 pixels.

Many multimedia formats are suitable including, by way of non-limiting examples, Adobe® Flash®, Apple® QuickTime®, Microsoft® Silverlight®, Java™, HTML 5, XHTML 5, and Unity®.

In some embodiments, an ad content file includes text and graphics suitable for display on a user interface of a compact electronic device.

In some embodiments, the systems and methods described herein comprise a software module providing information on nearby health systems. In some embodiments, a nearby health system is a lab, a hospital, a doctor, a clinic, a test facility, or other healthcare facility. In some embodiments, the information on a nearby healthcare system comprises one or more of a location of a healthcare system, service(s) offered, hours of operations, contact information, and travel distance/time based on a current location of the user.

In some embodiments, the systems and methods described herein comprise a software module providing notifications and/or reminders. In some embodiments, a reminder is provided to a user to run a test. In some embodiments, a reminder is provided to a user to take medication. In some embodiments, a notification is provided to a user informing the user of doctor(s) and/or nearby support group(s).

In some embodiments, the systems and methods described herein comprise a software module providing a pay wall for a user to obtain ad-free testing. In some embodiments, a user pays a flat fee to obtain ad-free testing (e.g., ad-free and question-free). In some embodiments, a user pays a subscription to obtain ad-free testing.

Databases

In various embodiments, the subject matter disclosed herein includes one or more databases, or use of the same to store biological sequences, reference sequences, and test or assay results. In view of the disclosure provided herein, those of skill in the art will recognize that many databases are suitable for storage and retrieval of the sequence information. In various embodiments, suitable databases include, by way of non-limiting examples, relational databases, non-relational databases, object oriented databases, object databases, entity-relationship model databases, associative databases, and XML databases. In some embodiments, a database is internet-based. In further embodiments, a database is web-based. In still further embodiments, a database is cloud computing-based. In other embodiments, a database is based on one or more local computer storage devices.

In some embodiments, a database comprises a network of individuals or subjects. In some embodiments, the network of individuals or subjects is a social network. In some embodiments, the individuals are data consumers. In some embodiments, the database comprises data analysis results obtained by the individuals. In some embodiment, the database comprises a list of analytes. In some embodiments, the individuals are anonymous. In some embodiments, the database is searchable using a query interface. In some embodiments, the database is searchable by an individual. In some embodiments, the database is searchable by a physician. In some embodiments, the database is searchable by a researcher.

In some embodiments, the database stores user profiles and/or user information associated with the test or assay results. In some embodiments, the database is searchable by an advertiser. The database can be searchable with varying restrictions based on the party performing the search. For example, in some embodiments, an advertiser is limited to anonymized user profile information without having access to any health information, while the physician of a user is able to access health information for that user. Meanwhile, a researcher is able to access anonymized user profile information and anonymized HIPAA-compliant health information. In some embodiments, data stored in one or more databases is encrypted. In some embodiments, third party applications are blocked from accessing private information stored in the one or more databases.

In some embodiments, the systems and methods described herein comprise a first database having public access (e.g., members of the general public can access the database). In some embodiments, the first database is anonymized and otherwise HIPAA-compliant. In some embodiments, the first database provides limited access to information or data stored within. For example, in some embodiments, the first database only provides statistical information such as prostate cancer rate in a certain age group, and does not allow access to individual information. In some embodiments, the systems and methods described herein comprise a second database for non-public access. In some embodiments, researchers or research institutions, corporations, healthcare providers, or other non-public groups have access to the second database. In some embodiments, the second database is anonymized and otherwise HIPAA-compliant. In some embodiments, the second database provides limited access to information or data stored within. In some embodiments, one or more databases or phone applications interface with healthcare system applications to share and/or retrieve information. In some embodiments, one or more databases connect to one or more exercise applications on a phone to obtain user information (e.g., to add to the user profile).

Assays and Applications

In some embodiments, the methods described herein allow for isolating and detecting an analyte using an assay, such as an immunoassay or a nucleic acid or protein assay. In some embodiments, the assay uses devices and systems suitable for isolating or separating analytes from a fluid composition. In various aspects, assays herein allow for a rapid procedure that requires a minimal amount of material and/or results in a high purity DNA isolated from biological samples. Assays and applications herein comprise applying the biological sample to a cartridge comprising an array of electrodes capable of generating AC electrokinetic forces when the array of electrodes is energized. In some embodiments a dielectrophoretic field is a component of AC electrokinetic force effects. In some embodiments, the AC electrokinetic force, including dielectrophoretic fields, comprises high-field regions (positive DEP area where there is a strong concentration of electric field lines due to a non-uniform electric field) and/or low-field regions (negative DEP area where there is a weak concentration of electric field lines due to a non-uniform electric field). In some embodiments, the analyte comprises a biomarker. In some embodiments, the analyte comprises a nucleic acid. In some embodiments, the analyte comprises a protein.

In specific instances, the analytes are isolated in a field region (e.g., a high field region) of the dielectrophoretic field. In some embodiments, the assay further includes one or more of the following steps: concentrating cells of interest in a first dielectrophoretic field region (e.g., a low field DEP region), lysing cells in the first dielectrophoretic field region, and/or concentrating nucleic acid in a second dielectrophoretic field region (e.g., a high field DEP region). In other embodiments, the assay includes one or more of the following steps: concentrating cells in a first dielectrophoretic field region (e.g., a low field DEP region), concentrating nucleic acid in a second dielectrophoretic field region (e.g., a high field DEP region), and washing away the cells and residual material. The assay also optionally includes devices and/or systems capable of performing one or more of the following steps: washing or otherwise removing residual (e.g., cellular) material from the nucleic acid (e.g., rinsing the array with water or buffer while the nucleic acid is concentrated and maintained within a high field DEP region of the array), degrading residual proteins (e.g., residual proteins from lysed cells and/or other sources, such degradation occurring according to any suitable mechanism, such as with heat, a protease, or a chemical), flushing degraded proteins from the nucleic acid, and collecting the nucleic acid. In some embodiments, the result of the assays described herein is an isolated nucleic acid, optionally of suitable quantity and purity for enzymatic reactions, such as PCR or DNA sequencing.

In some embodiments, the methods described herein allow for performing enzymatic reactions. In other embodiments, the methods described herein allow for performing polymerase chain reaction (PCR), isothermal amplification, ligation reactions, restriction analysis, nucleic acid cloning, transcription or translation assays, or other enzymatic-based molecular biology assay.

In some embodiments, the methods described herein are performed in a short amount of time. In some embodiments, the period of time is short with reference to the "procedure time" measured from the time between adding the fluid to the device and detecting changes in the analyte. In some embodiments, the procedure time is less than 3 hours, less than 2 hours, less than 1 hour, less than 30 minutes, less than 20 minutes, less than 10 minutes, or less than 5 minutes. In another aspect, the period of time is short with reference to the "hands-on time" measured as the cumulative amount of time that a person must attend to the procedure from the time between adding the fluid to the device and measuring the changes in the analyte. In some embodiments, the hands-on time is less than 20 minutes, less than 10 minutes, less than 5 minute, less than 1 minute, or less than 30 seconds.

In some embodiments, the methods described herein comprise amplifying the isolated nucleic acid by polymerase chain reaction (PCR). In some embodiments, the device or system comprise a heater and/or temperature control mechanisms suitable for thermocycling. PCR is optionally done using traditional thermocycling by placing the reaction chemistry analytes in between two efficient thermoconductive elements (e.g., aluminum or silver) and regulating the reaction temperatures using TECs. Additional designs optionally use infrared heating through optically transparent material like glass or thermo polymers. In some instances, designs use smart polymers or smart glass that comprise conductive wiring networked through the substrate. This conductive wiring enables rapid thermal conductivity of the materials and (by applying appropriate DC voltage) provides the required temperature changes and gradients to sustain efficient PCR reactions. In certain instances, heating is applied using resistive chip heaters and other resistive elements that will change temperature rapidly and proportionally to the amount of current passing through them.

In some embodiments, the methods described herein are used in conjunction with traditional fluorometry (CCD, pmt, other optical detector, and optical filters), fold amplification is monitored in real-time or on a timed interval. In certain instances, quantification of final fold amplification is reported via optical detection converted to AFU (arbitrary fluorescence units correlated to analyze doubling) or translated to electrical signal via impedance measurement or other electrochemical sensing.

In some instances, light delivery schemes are utilized to provide the optical excitation and/or emission, and/or detection of fold amplification. In certain embodiments, this includes using the flow cell materials (thermal polymers like acrylic (PMMA) cyclic olefin polymer (COP), cyclic olefin co-polymer, (COC), etc.) as optical wave guides to remove the need to use external components. In addition, in some instances light sources—light emitting diodes—LEDs, vertical-cavity surface-emitting lasers—VCSELs, and other lighting schemes are integrated directly inside the flow cell or built directly onto the micro electrode array surface to have internally controlled and powered light sources. Miniature PMTs, CCDs, or CMOS detectors can also be built into the flow cell. This minimization and miniaturization enables compact devices capable of rapid signal delivery and detection while reducing the footprint of similar traditional devices (e.g. a standard bench top PCR/QPCR/Fluorometer).

In some embodiments, the isolated sample disclosed herein is further utilized in a variety of assay formats. For instance, in some embodiments, devices which are addressed with nucleic acid probes or amplicons are utilized in dot blot or reverse dot blot analyses, base-stacking single nucleotide polymorphism (SNP) analysis, SNP analysis with electronic stringency, or in STR analysis. In addition, such methods described herein are utilized in formats for enzymatic nucleic acid modification, or protein-nucleic acid interaction, such as, e.g., gene expression analysis with enzymatic reporting, anchored nucleic acid amplification, or other nucleic acid modifications suitable for solid-phase formats including restriction endonuclease cleavage, endo- or exo-nuclease cleavage, minor groove binding protein assays, terminal transferase reactions, polynucleotide kinase or phosphatase reactions, ligase reactions, topoisomerase reactions, and other nucleic acid binding or modifying protein reactions.

In addition, in some embodiments, the methods described herein are useful in immunoassays. For instance, in some embodiments, some of the methods described herein are used with antigens (e.g., peptides, proteins, carbohydrates, lipids, proteoglycans, glycoproteins, etc.) in order to assay for antibodies in a bodily fluid sample by sandwich assay, competitive assay, or other formats. Alternatively, in some embodiments, the locations of the device are addressed with antibodies, in order to detect antigens in a sample by sandwich assay, competitive assay, or other assay formats. In some embodiments, the isolated nucleic acids are useful for use in immunoassay-type arrays or nucleic acid arrays.

Enzymes

In some embodiments, the method includes introduction of enzymes to the sample. In some embodiments, the enzyme is a restriction enzyme. Non limiting examples of a restriction enzyme are AcII, HindIII, SspI, MluCI Tsp509I, PciI, AgeI, BspMI, BfuAI, SexAI, MluI, BceAI, HpyCH4IV, HpyCH4III, BaeI, BsaXI, AflIII, SpeI, BsrI, BmrI, BglII, AfeI, AluI, StuI, ScaI, ClaI, PI-SceI, NsiI, AseI, SwaI, CspCI, MfeI, BssSI, BmgBI, PmlI, DraIII, AleI, EcoP15I, PvuII, AlwNI, BtsIMutI, TspRI, NdeI, NlaIII, CviAII, FatI, MslI, FspEI, XcmI, BstXI, PflMI, BccI, NcoI, BseYI, FauI, SmaI, XmaI TspMI, Nt,CviPII, LpnPI, AciI, SacII, BsrBI, MspI HpaII, ScrFI, BssKi StyD4I, BsaJI, BslI, BtgI, NciI, AvrII, MnII, BbvCI, Nb.BbvCI, Nt.BbvCI, SbfI, BpU10I, Bsu36I, EcoNI, HpyAV, BstNI, PspGI, StyI, BcgI, PvuI BstUI, EagI, RsrII, BbiEI, BsiWI, BsmBI, Hpy99I, MspA1I, MspJI, SgrAI, BfaI, BspCNI, XhoI, EarI, AcuI, PstI, BpmI, DdeI, SfcI, AflII, BpuEI, SmlI, AvaI BsoBI, MboII, BbsI, XmnI, BsmI, Nb.BsmI, EcoRI, HgaI, AarII, ZraI, Tth111IPflFI, PshAI, AhdI, DrdI, Eco53kI, SacI, BseRI, PleI, Nt.BstNBI, MlyI, HinfI, EcoRV, MboI Sau3AI, DpnI, BsaBI, TfiI, BsrDI, Nb.BsrDI, BbvI, BtsI, Nb.BtsI, BstAPI, SfaNI, SphI, SrfI, MneAIII, NaeI, NgoMIV, BglI, AsiSI, BtgZI, HinP1I, HhaI, BssHII, NotI, Fnu4HI, Cac8I, MwoI, NheI, BmtI, SapI, Nt.BspQI, BlpI, TseI ApeKI, Bsp1286I, AlwI, Nt.AlwI, BamHI, FokI, BtsCI, HaeIII, FseI, SfiI, NarI, KasI, SfoI PluTI, AscI, EciI, BsmFI, ApaI, PspOMI, Sau96I, NlaIV, KpnI, Acc65I, BsaI, HphI, BstEII, AvaII, BanI, BaeGI, BsaHI, BanII, RsaI, CviQI BstZ17I, BciVI, SalI, Nt.BsmAI, BsmAI BcoDI, ApaLI, BsgI AccI, Hpy166II, Tsp45I, HpaI, PmeI, HincII, BsiHKAI, ApoI, NspI, BsrFI, BstYI, HaeII, CviKI-1, EcoO109I, PpuMI, I-CeuI SnaBI, I-SceI, BspHI, BspEI, MmeI, Taq-I, Nrul, Hpy188I, Hpy188III, XbaI, BclI, HpyCH4V, FspI, PI-PspI, MscI, BsrGI, MseI MacI, PsiI, BstBI, DraI, PspXI, BsaWI, BsaAI, and EaeI.

In other embodiments, the enzyme is an exonuclease. Non limiting examples of an exonuclease are Lambda Exonuclease, T7 Exonuclease, Exonuclease III, RecJ$_f$ Exonuclease I, Exonuclease I, Exonuclease V, Nuclease BAL-31, Mung Bean Nuclease, DNase I, Micrococcal Nuclease, T7 Endonuclease I, and T5 Exonuclease.

In other embodiments, the enzyme is a protease. Non limiting examples of a protease are Achromopeptidase, Aminopeptidase, Ancrod, Angiotensin Converting Enzyme, Bromelain, Calpain, Calpain I, Calpain II, Carboxypeptidase A, Carboxypeptidase B, Carboxypeptidase G, Carboxypeptidase P, Carboxypeptidase W, Carboxypeptidase Y, Caspases (general), Caspase 1, Caspase 2, Caspase 3, Caspase 4, Caspase 5, Caspase 6, Caspase 7, Caspase 8, Caspase 9, Caspase 10, Caspase 11, Caspase 12, Caspase 13, Cathepsin B, Cathepsin C, Cathepsin D, Cathepsin E, Cathepsin G, Cathepsin H, Cathepsin L, Chymopapain, Chymase, Chymotrypsin, Clostripain, Collagenase, Complement Clr, Complement Cls, Complement Factor D, Complement factor I, Cucumisin, Dipeptidyl Peptidase IV, Elastase leukocyte, Elastase pancreatic, Endoproteinase Arg-C, Endoproteinase Asp-N, Endoproteinase Glu-C, Endoproteinase Lys-C, Enterokinase, Factor Xa, Ficin, Furin, Granzyme A, Granzyme B, HIV Protease, IGase, Kallikrein tissue, Leucine Aminopeptidase (General), Leucine aminopeptidase, cytosol, Leucine aminopeptidase, microsomal, Matrix metalloprotease, Methionine Aminopeptidase, Neutrase, Papain, Pepsin, Plasmin, Prolidase, Pronase E, Prostate Specific Antigen, Protease, Alkalophilic from *Streptomyces griseus*, Protease from *Aspergillus*, Protease from *Aspergillus saitoi*, Protease from *Aspergillus sojae*, Protease (*B. licheniformis*) (Alkaline), Protease (*B. licheniformis*) (Alcalase), Protease from *Bacillus polymyxa*, Protease from *Bacillus* sp, Protease from *Bacillus* sp (Esperase), Protease from *Rhizopus* sp., Protease S, Proteasomes, Proteinase from *Aspergillus oryzae*, Proteinase 3, Proteinase A, Proteinase K, Protein C, Pyroglutamate aminopeptidase, Renin, Rennin, Streptokinase, Subtilisin, Thermolysin, Thrombin, Tissue Plasminogen Activator, Trypsin, Tryptase, and Urokinase In other embodiments, the enzyme is a lipase. Non limiting examples of a lipase are biological lipases such as bile salt-dependent lipase, pancreatic lipase, lysosomal lipase, hepatic lipase, lipoprotein lipase, hormone-sensitive lipase, gastric lipase, endothelial lipase, pancreatic lipase related protein, pancreatic lipase related protein 1, lingual lipase, lipase members H, I, J, K, M and N, monoglyceride lipase, dicylglycerol lipase alpha, diacylglycerol lipase beta, and carboxyl ester lipase.

Removal of Residual Material

In some embodiments, following isolation of the analytes, the method includes optionally flushing residual material from the isolated analytes. In some embodiments, the methods described herein optionally and/or comprise a reservoir comprising a fluid suitable for flushing residual material from the analytes. "Residual material" is anything originally present in the sample, originally present in the cells, added during the procedure, created through any step of the process including but not limited to cells (e.g. intact cells or residual cellular material), and the like. For example, residual material includes intact cells, cell wall fragments, proteins, lipids, carbohydrates, minerals, salts, buffers, plasma, and the like. In some embodiments, a certain amount of analyte is flushed with the residual material.

In some embodiments, the residual material is flushed in any suitable fluid, for example in water, TBE buffer, or the like. In some embodiments, the residual material is flushed with any suitable volume of fluid, flushed for any suitable period of time, flushed with more than one fluid, or any other variation. In some embodiments, the method of flushing residual material is related to the desired level of isolation of the analyte, with higher purity analyte requiring more stringent flushing and/or washing. In other embodiments, the method of flushing residual material is related to the particular starting material and its composition. In some instances, a starting material that is high in lipids requires a flushing procedure that involves a hydrophobic fluid suitable for solubilizing lipids.

In some embodiments, the method includes degrading residual material including residual protein. For example, proteins are degraded by one or more of chemical degradation (e.g. acid hydrolysis) and enzymatic degradation. In some embodiments, the enzymatic degradation agent is a protease. In other embodiments, the protein degradation agent is Proteinase K. The optional step of degradation of residual material is performed for any suitable time, temperature, and the like. In some embodiments, the degraded residual material (including degraded proteins) is flushed from the isolated analytes.

In some embodiments, the agent used to degrade the residual material is inactivated or degraded. In some embodiments, an enzyme used to degrade the residual material is inactivated by heat (e.g., 50 to 95° C. for 5-15 minutes). For example, enzymes including proteases, (for example, Proteinase K) are degraded and/or inactivated using heat (typically, 15 minutes, 70° C.). In some embodiments wherein the residual proteins are degraded by an enzyme, the method further comprises inactivating the degrading enzyme (e.g., Proteinase K) following degradation of the proteins. In some embodiments, heat is provided by a heating module in the device (temperature range, e.g., from 30 to 95° C.).

The order and/or combination of certain steps of the method can be varied. In some embodiments, the methods are capable of performing certain steps in any order or combination. For example, in some embodiments, the residual material and the degraded proteins are flushed in separate or concurrent steps. That is, the residual material is flushed, followed by degradation of residual proteins, followed by flushing degraded proteins from the isolated analytes. In some embodiments, the residual proteins are first degraded, and then both the residual material and degraded proteins are flushed from the analytes in a combined step.

In some embodiments, the analytes are used in PCR, enzymatic assays, or other procedures that analyze, characterize or amplify the analytes.

For example, in some embodiments, the isolated analyte is a nucleic acid, and the methods described herein are capable of performing PCR or other optional procedures on the isolated nucleic acids. In other embodiments, the nucleic acids are collected and/or eluted from the device. In some embodiments, the methods described herein are capable of allowing collection and/or elution of nucleic acid from the device or system. Exemplary eluents include water, TE, TBE, and L-Histidine buffer.

In some embodiments, isolated nucleic acids will be in native state, e.g. still associated with proteins or trapped in exosomes, in comparison to other isolation techniques where digestion/lysis steps are taken in order to isolate the nucleic acids.

Isolated protein components can also be called immunoproteins with clinical application such as CEA, CA-125, PAS, CA 27.29, CA15-3, Cyfra-21, AFP, BHCG, etc. Since the isolation occurs selectively thru antibody binding, the protein will be free of other aggregates and will be in a solution such as to prevent aggregation and denaturation.

Samples

In some embodiments, the sample comprises a fluid or a sample fluid. In one aspect, the sample is a biological sample. In one aspect, the sample is a biological material. In one aspect, the biological material is a biological fluid. In one aspect, the biological fluid is blood. In one aspect, the sample comprises cells or other particulate material. In some embodiments, the sample does not comprise cells. In another aspect, the sample is an environmental sample.

In some embodiments, the sample is a liquid, optionally water, an aqueous solution, or dispersion. In some embodiments, the sample is a bodily fluid. Exemplary bodily fluids include whole blood, plasma, serum, saliva, cerebrospinal fluid, lymph fluid, urine, sweat, tears, amniotic fluid, aqueous humor, vitreous humor, pleural fluid, mucus, synovial fluid, exudate, interstitial fluid, peritoneal fluid, pericardial fluid, sebum, semen, bile, and the like. In some embodiments, analytes are measured within bodily fluids using the methods described herein are part of a medical therapeutic or diagnostic procedure, device, or system. In some embodiments, the sample is tissues and/or cells solubilized and/or dispersed in a fluid medium. For example, the tissue can be a cancerous tumor from which analytes, such as nucleic acids, can be isolated using the methods, devices, or systems described herein.

In some embodiments, the sample is an environmental sample. In some embodiments, the environmental sample is assayed or monitored for the presence of a particular nucleic acid sequence indicative of a certain contamination, infestation incidence, or the like. The environmental sample can also be used to determine the source of a certain contamination, infestation incidence or the like using the methods, devices, or systems described herein. Exemplary environmental samples include municipal wastewater, industrial wastewater, water or fluid used in or produced as a result of various manufacturing processes, lakes, rivers, oceans, aquifers, ground water, storm water, plants or portions of plants, animals or portions of animals, insects, municipal water supplies, and the like.

In some embodiments, the sample is a food or beverage. The food or beverage can be assayed or monitored for the presence of a particular analyte indicative of a certain contamination, infestation incidence, or the like. The food or beverage can also be used to determine the source of a certain contamination, infestation incidence or the like using the methods described herein. In various embodiments, the methods described herein can be used with one or more of bodily fluids, environmental samples, and foods and beverages to monitor public health or respond to adverse public health incidences.

In some embodiments, the sample is a growth medium. The growth medium can be any medium suitable for culturing cells, for example lysogeny broth (LB) for culturing *E. coli*, Ham's tissue culture medium for culturing mammalian cells, and the like. The medium can be a rich medium, minimal medium, selective medium, and the like. In some embodiments, the medium comprises or consists essentially of a plurality of clonal cells. In some embodiments, the medium comprises a mixture of at least two species. In some embodiments, the cells comprise clonal cells, pathogen cells, bacteria cells, viruses, plant cells, animal cells, insect cells, and/or combinations thereof.

In some embodiments, the sample is water.

In some embodiments, the sample comprises other particulate material. In some embodiments, such particulate material are, for example, inclusion bodies (e.g., ceroids or Mallory bodies), cellular casts (e.g., granular casts, hyaline casts, cellular casts, waxy casts and pseudo casts), Pick's bodies, Lewy bodies, fibrillary tangles, fibril formations, cellular debris, or other particulate material. In some embodiments, particulate material is an aggregated protein (e.g., beta-amyloid).

In some embodiments, the sample is a small volume of liquid including less than 10 ml. In some embodiments, the sample is less than 8 ml. In some embodiments, the sample is less than 5 ml. In some embodiments, the sample is less than 2 ml. In some embodiments, the sample is less than 1 ml. In some embodiments, the sample is less than 500 µl. In some embodiments, the sample is less than 200 µl. In some embodiments, the sample is less than 100 µl. In some embodiments, the sample is less than 50 µl. In some embodiments, the sample is less than 10 µl. In some embodiments, the sample is less than 5 µl. In some embodiments, the sample is less than 1 µl.

In some embodiments, the quantity of sample used in the method comprises less than about 100,000,000 cells. In some embodiments, the sample comprises less than about 10,000,000 cells. In some embodiments, the sample comprises less than about 1,000,000 cells. In some embodiments, the sample comprises less than about 100,000 cells. In some embodiments, the sample comprises less than about 10,000 cells. In some embodiments, the sample comprises less than about 1,000 cells.

In some embodiments, isolation of an analyte from a sample methods described herein takes less than about 30 minutes, less than about 20 minutes, less than about 15 minutes, less than about 10 minutes, less than about 5 minutes or less than about 1 minute. In other embodiments, isolation of an analyte from a sample with methods described herein takes no more than 30 minutes, no more than about 20 minutes, no more than about 15 minutes, no more than about 10 minutes, no more than about 5 minutes, no more than about 2 minutes, or no more than about 1 minute. In additional embodiments, isolation of an analyte from a sample with the methods described herein takes less than about 15 minutes, less than about 10 minutes, or less than about 5 minutes.

In some embodiments, the analyte is a macroscale analyte.

In some embodiments, the methods described herein are used to obtain, isolate, or separate any desired analyte. In some embodiments, the analyte is a nucleic acid. In other embodiments, the nucleic acids isolated by the methods described herein include DNA (deoxyribonucleic acid), RNA (ribonucleic acid), and combinations thereof. In some embodiments, the analyte is protein fragments. In some embodiments, the nucleic acid is isolated in a form suitable for sequencing or further manipulation of the nucleic acid, including amplification, ligation, or cloning.

In some embodiments, the sample consists of a combination of micron-sized entities or cells, larger nanoparticulates, and smaller nanoparticulates or biomolecules. In some embodiments, the micron-sized entities comprise blood cells, platelets, bacteria, and the like. In some embodiments, larger nanoparticulates comprise particulates in the range of about 10 nm and about 900 nm effective stokes diameter, and comprise exosomes, high mw nucleic acids, including high mw DNA, oligo-nucleosome complexes, aggregated proteins, vesicle bound DNA, cell membrane fragments, and cellular debris dispersed in the sample. In some embodiments, smaller nanoparticulates (<10 nm effective stokes diameter) comprise proteins such as immunoglobulins, human serum albumin, fibrinogen and other plasma proteins, smaller apoptotic DNA, and free ions.

In some embodiments, the assays and methods disclosed herein are capable of selectively isolating target particulates, including micron-sized entities, larger nanoparticulates, and/or smaller nanoparticulates. In some embodiments, the assays and methods disclosed herein are capable of selectively isolating target particulates, including micron-sized entities, larger nanoparticulates, and/or smaller nanoparticulates in complex biological or environmental samples. The target particulates are isolated in different field regions at or near the surface of the array or cartridge, allowing non-target particulates or particulates that are not isolated at or near the surface of the array or cartridge to be flushed from the array or cartridge.

In some embodiments, the larger nanoparticulate molecular target includes exosomes, high mw nucleic acids, including high mw DNA, oligo-nucleosome complexes, aggregated proteins, vesicle bound DNA, cell membrane fragments, and cellular debris. In other embodiments, the target circulating cell-free biomarker includes mutations, deletions, rearrangements or methylated nucleic acid of circulating, cell-free DNA, micro RNA, RNA from microvesicles, or a combination thereof. In still other embodiments, the detection of the cell-free biomarker provides information useful for cancer diagnosis, cancer prognosis or treatment response in a patient. In yet other embodiments, the tumor cell-free biomarker is associated with CNS tumors, neuroblastoma, gliomas, breast cancer, endometrial tumors, cervical tumors, ovarian tumors, hepatocellular carcinoma, pancreatic carcinoma, esophageal tumors, Stoch tumors, colorectal tumors, head and neck tumors, nasopharyngeal carcinoma, thyroid tumors, lymphoma, leukemia, lung cancer, non-small cell lung carcinoma, small cell lung carcinoma, testicular tumors, kidney tumors, prostate carcinoma, skin cancer, malignant melanoma, squamous cell carcinoma or a combination thereof. In some embodiments, the tumor cell-free biomarker is GFAP, VEGF, EGFR, b-FGF, KRAS, YKL-40, MMP-9, or combinations thereof.

In other embodiments, the target biomarker is chosen from the group consisting of proteins, lipids, antibodies, high molecular weight DNA, tumor cells, exosomes, nucleosomes and nanosomes. In still other embodiments, the bound nucleic acid is eluted from the first chamber for further characterization. In yet other embodiments, the eluted nucleic acid is amplified or sequenced.

In various embodiments, the analyte is a composition that is free from at least 99% by mass of other materials, free from at least 99% by mass of residual cellular material, free from at least 98% by mass of other materials, free from at least 98% by mass of residual cellular material, free from at least 95% by mass of other materials, free from at least 95% by mass of residual cellular material, free from at least 90% by mass of other materials, free from at least 90% by mass of residual cellular material, free from at least 80% by mass of other materials, free from at least 80% by mass of residual cellular material, free from at least 70% by mass of other materials, free from at least 70% by mass of residual cellular material, free from at least 60% by mass of other materials, free from at least 60% by mass of residual cellular material, free from at least 50% by mass of other materials, free from at least 50% by mass of residual cellular material, free from at least 30% by mass of other materials, free from at least 30% by mass of residual cellular material, free from at least 10% by mass of other materials, free from at least 10% by mass of residual cellular material, free from at least 5% by mass of other materials, or free from at least 5% by mass of residual cellular material.

In various embodiments, the analyte has any suitable purity. For example, if an enzymatic assay requires analyte samples having about 20% residual cellular material, then isolation of the analyte to 80% is suitable. In some embodiments, the isolated analyte comprises less than about 80%, less than about 70%, less than about 60%, less than about 50%, less than about 40%, less than about 30%, less than about 20%, less than about 10%, less than about 5%, or less than about 2% non-analyte cellular material and/or protein by mass. In some embodiments, the isolated analyte comprises greater than about 99%, greater than about 98%, greater than about 95%, greater than about 90%, greater than about 80%, greater than about 70%, greater than about 60%, greater than about 50%, greater than about 40%, greater than about 30%, greater than about 20%, or greater than about 10% analyte by mass.

Nucleic Acids

The analytes are isolated in any suitable form including unmodified, derivatized, fragmented, non-fragmented, and the like. In some embodiments, when the analyte is a nucleic acid, the nucleic acid is collected in a form suitable for sequencing. In some embodiments, the nucleic acid is collected in a fragmented form suitable for shotgun-sequencing, amplification, or other manipulation. In some embodiments, the nucleic acid is collected in a solution comprising reagents used in, for example, a DNA sequencing procedure, such as nucleotides as used in sequencing by synthesis methods.

When the analyte is a nucleic acid, the nucleic acid isolated using the methods described herein is high-quality and/or suitable for DNA sequencing, nucleic acid amplification, such as PCR, or other nucleic acid manipulation, such as ligation, cloning or further translation or transformation assays. In some embodiments, the collected nucleic acid comprises at most 0.01% protein. In some embodiments, the collected nucleic acid comprises at most 0.5% protein. In some embodiments, the collected nucleic acid comprises at most 1% protein. In some embodiments, the collected nucleic acid comprises at most 2% protein. In some embodiments, the collected nucleic acid comprises at most 3% protein. In some embodiments, the collected nucleic acid comprises at most 4% protein. In some embodiments, the collected nucleic acid comprises at most 5% protein Protein When the analyte is a protein or protein fragment, the protein or protein fragment isolated using the methods described herein is high-quality and/or suitable for using directly in downstream procedures. In some embodiments, the collected protein or protein fragment comprises at most 0.01% non-target protein. In some embodiments, the collected protein or protein fragment comprises at most 0.5% non-target protein. In some embodiments, the collected protein or protein fragment comprises at most 0.1% non-target protein. In some embodiments, the collected protein or protein fragment comprises at most 1% non-target protein. In some embodiments, the collected protein or protein fragment comprises at most 2% non-target protein. In some embodiments, the collected protein or protein fragment comprises at most 3% non-target protein. In some embodiments, the collected protein or protein fragment comprises at most 4% non-target protein. In some embodiments, the collected protein or protein fragment comprises at most 5% non-target protein.

Detection and Characterization of Cancer Using Cell-Free Biomarkers

In some embodiments, assays are performed on circulating cell-free high molecular weight DNA (>300 bp) and other target cell-free biomarkers isolated using the methods and devices disclosed herein to characterize cancer in patients using target specific cell-free biomarkers. "Characterization" of cancer includes, but is not limited to, detection and diagnosis of cancer, prognosis of disease, treatment response monitoring and other actions related to cancer analysis and treatment therein.

In some embodiments, the characterization is performed via molecular profiling of cell-free biomarkers. The profiling includes, but is not limited to, enumeration of analytes, specific detection of analytes, including, but not limited to, proteins, lipids, antibodies, tumor DNA, tumor cells, exosomes, nucleosomes, nanosomes detection of specific gene sequences, detection of mutant gene sequences, detection of loss of heterozygosity, determination of methylation status, detection of alterations, detection of deletions, and other molecular profiling assays used in the analysis and characterization of physical and/or biochemical status of a patient or subject.

Cell-free biomarkers can be derived from proteins or molecules associated with cellular exocytosis, necrosis, or secretion processes. Examples of biomarkers include: high molecular weight DNA (>300 bp), nucleosomes, exosomes, aggregated proteins, cell membrane fragments, mitochondria, cellular vesicles, extracellular vesicles, and other markers related to cellular exocytosis, necrosis, or secretion.

Examples of candidates for circulating cell-free biomarkers include, but are not limited to, cell-free circulating tumor DNA (ctDNA), including mutations or deletions, rearrangement, methylated nucleic acid, loss of heterozygosity, and other DNA alterations. In some embodiments, RNA is also used, including, but not limited to, micro RNA (miRNA), RNA from microvesicles and other RNA forms that provide useful information with regards to the characterization of, for example, cancer diagnosis, prognosis, and treatment response in a patient. In some embodiments, tumor cells are directly monitored, as well as cell free proteins, including, but not limited to, GFAP, VEGF, EGFR, b-FGF, KRAS, YKL-40, and MMP-9.

The methods and devices disclosed herein for characterization of, for example, cancer patients and subjects uses AC Electrokinetics to isolate cell free target biomarkers directly from whole blood, serum, plasma, or other bodily fluid or sample. The methods and devices disclosed herein use minimal amounts of sample, for example, up to 10 µl, up to 20 µl, up to 30 µl, up to 40 µl, up to 50 µl, up to 60 µl, up to 70 µl, up to 80 µl, up to 90 µl, up to 100 µl, up to 200 µl, up to 300 µl, up to 400 µl, up to 500 µl, or more of sample. In some embodiments, the methods and devices disclosed herein use less than 500 µl, less than 400 µl, less than 300 µl, less than 200 µl, less than 100 µl, less than 90 µl, less than 80 µl, less than 70 µl, less 60 µl, less than 50 µl, less than 40 µl, less than 30 µl, less than 20 µl, less than 10 µl, or less than 5 µl of sample. In some embodiments, the methods and devices disclosed herein use between about 50 µl of sample and about 500 µl of sample.

The methods and devices disclosed herein for characterization of, for example, cancer patients and subjects use intercalating dyes, antibody labeling, or other traditional staining techniques to enable direct quantification using fluorescence microscopy or other detection techniques. In some embodiments, the methods and devices disclosed herein also use DNA/RNA hybridization techniques to detect specific alleles implicated in cancer. In some embodiments, the methods and devices disclosed herein also use Quantitative Real Time PCR, including of nuclear or mitochondrial DNA or other target nucleic acid molecule markers, enzyme-linked immunosorbent assays (ELISA), direct SYBR gold assays, direct PicoGreen assays, or loss of heterozygosity (LOH) of microsatellite markers, optionally followed by electrophoresis analysis, including, but not limited to, capillary electrophoresis analysis, sequencing and/or cloning, including next generation sequencing, methylation analysis, including, but not limited to, modified semi-nested or nested methylation specific PCR, DNA specific PCR (MSP), quantification of minute amounts of DNA after bisulfitome amplification (qMAMBRA), as well as methylation on beads, mass-based analysis, including, but not limited to, MALDI-ToF (matrix-assisted laser desorption/ionization time of flight analysis, optionally in combination with PCR, and digital PCR.

In some embodiments, the methods and devices disclosed herein employ dyes, including intercalating dyes, antibody labeling, stains and other imaging molecules that enable direct quantification of the cell-free biomarker materials directly on or in use with the embodied devices, including the use of fluorescence microscopy. Examples of fluorescent labeling of nucleic acids (e.g. DNA and RNA) include, but are not limited to, cyanine dimers high-affinity stains (Life Technologies). Among them YOYO®-1, YOYO®-3, POPO™-1, POPO™-3, TOTO®-1, and TOTO®-3 are optionally chosen staining dyes. Fluorescent labeling of protein for detection and quantitation in conjunction with the methods and devices disclosed herein include, but are not limited to, Quanti-iT™ protein quantitation assay, NanoOrange™ protein quantitation assay, CBQCA protein quantitation assay (Life Technologies). In some embodiments, fluorescent quantitation of other cancer biomarkers is used including mitochondria, labelling dyes such as MitoTracker® Green FM® and MitoTracker® Red FM®.

In some embodiments, the methods and devices disclosed herein are used in conjunction with DNA/RNA hybridization techniques to detect specific alleles implicated in cancer. In some embodiments, specific electrodes and corresponding electrode trace lines can be designed to individually control separate electrodes so as to achieve a unique electric field distribution. In some embodiments, by designing non-uniform electric field distribution, specific DNA/RNA are manipulated.

Additionally, in some embodiments, the microelectrode arrays disclosed herein are further functionalized, for example, by covering the array with a reactive hydrogel. In some embodiments, the hydrogel comprises binding partners, including biotin binding protein; alternatively, the hydrogel is functionalized by acylation or by surface modification to chemisorb oligonucleotides on the surface. In some embodiments, the methods and devices disclosed herein are manipulated to attain control of hybridization and detection of specific alleles, for example, through the use of a Complimentary Metal-Oxide Semiconductor (CMOS) device that controls the microelectrode array in a manner that allows for multiple use of the array and high-throughput screening of matching oligonucleotides.

In some embodiments, the methods and devices disclosed herein enable elution of circulating cell-free target biomarkers such as nucleosomes, high molecular weight DNA, exosomes and proteins for post-genetic analysis and for quantification and further analysis using quantitative PCR, reverse transcriptase (RT) PCR, and sequencing analytical techniques for identifying proteins or nucleic acids of interest in the isolated and eluted sample DNA. Post-genetic analysis is performed on nucleosomal or nucleoprotein complexed dsDNA (greater than 300 bp), on exosomal dsDNA or RNA (greater than 100 bp), and/or on mitochondrial DNA.

Certain Terminology

The articles "a", "an" and "the" are non-limiting. For example, "the method" includes the broadest definition of the meaning of the phrase, which can be more than one method.

As used herein, the term "about" a particular value refers to a range of 10% above the value to 10% below the value. For example, "about 100" refers to 90 to 110.

EXAMPLES

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein are employed in practicing the invention. It is intended that the following claims define the scope of the invention and that methods and structures within the scope of these claims and their equivalents be covered thereby.

Example 1: Detecting Nanoscale Analytes in Complex Biological Samples

Using the devices and methods disclosed herein, 50 uL sample of blood from a subject is inserted into a cartridge and the cells are lysed using a 100 milli-second 100V DC pulse using an HP 3245A function generator. The nucleic acids from the blood cells are then gathered on the electrode surface using 10 kHz, 10 Vp-p.

Example 2: Monitoring a Disease State in an Individual

An individual who is being treated for lung cancer wishes to monitor treatment progress using a portable device. The portable device is powered by and controlled by a mobile phone. An application on the mobile phone is used to run the diagnostic assay. The individual creates a user profile in the application that includes a medical diagnosis, treatment regimen, and demographic information. The individual obtains a 50 µl sample of blood, inputs the sample into the device, and selects an assay appropriate to monitor treatment progress for lung cancer. The assay carried out by the portable device uses dielectrophoresis to isolate cell free nucleic acid particles from larger cellular particles in the blood. The cell free nucleic acid particles are visualized and quantitated using the camera of the mobile phone. While the assay is carried out, the user interface of the application shows advertisements targeted to the individual based on the user profile and the assay selected. When the assay is complete, the individual is given a result. The result is also transmitted to the individual's healthcare provider.

Example 3: Monitoring a Disease State in an Population

A population of individuals treated for lung cancer wish to monitor treatment progress using a portable device. The portable device is powered by and controlled by a mobile phone. An application on the mobile phone is used to run the diagnostic assay. Each individual creates a user profile in the application that includes a medical diagnosis, treatment regimen, and demographic information. Each individual obtains a 50 µl sample of blood, inputs the sample into the device, and selects an assay appropriate to monitor treatment progress for lung cancer. The assay carried out by the portable device uses dielectrophoresis to isolate cell free nucleic acid particles from larger cellular particles in the blood. The cell free nucleic acid particles are visualized and quantitated using the camera of the mobile phone. While the assay is carried out, the user interface of the application shows advertisements targeted to each individual based on the user profile and the assay selected. When the assay is complete, each individual is given a result. The result is also transmitted to each individual's healthcare provider and to an online database. Each individual's user profile and results are present in the online database which is searchable by each individual, each individual's healthcare provider, and medical researchers. The online database provides a resource to monitor treatment results in a population of individuals undergoing treatment. The online database also provides a resource for individuals undergoing treatment to compare their results and to connect with other individuals and other healthcare providers.

Example 4: Choice of Advertising or Answering Questions

An individual who is being treated for lung cancer is provided with a portable device for monitoring treatment progress free of charge by his healthcare provider. The portable device is an analyte analysis apparatus powered by and controlled by a tablet. The portable device has an adapter that accounts for the larger size of the table relative to mobile phones when positioning the tablet to run the diagnostic assay. An application on the tablet is used to run the diagnostic assay. The individual creates a user profile in the application that includes a medical diagnosis, treatment regimen, and demographic information. The user profile is also enhanced with social media information and preferences imported from the individual's Facebook profile. Every week, the individual uses the portable device to monitor his treatment progress. The individual obtains a 50 µl sample of blood, inputs the sample into the device, and selects an assay appropriate to monitor treatment progress for lung cancer. The assay carried out by the portable device uses dielectrophoresis to isolate cell free nucleic acid particles from larger cellular particles in the blood. The cell free nucleic acid particles are visualized and quantitated using the camera of the tablet. While the assay is carried out, the user interface of the application presents a choice of answering questions or watching advertisements targeted to the individual based on the user profile and the assay selected. The questions are from a paid survey provided by a third-party. The individual selects survey and answers the questions. When the assay is complete, the individual is given a result. The result is also transmitted to the individual's healthcare provider. The next week, the individual runs the diagnostic assay again. Because the individual indicated his cancer diagnosis and treatment regimen in his user profile, a remote server compares this information against a database of ads to determine a pool of relevant ads, and then selects from this pool an ad for a novel lung cancer treatment to present to the user. The healthcare provider receives payment for the targeted ad. Over time, repeated payments for ads/questions over time serves to offset the cost of the portable device for the healthcare provider, thereby allowing the individual access to the portable device for self-monitoring of treatment progress without being required to pay for the device.

Example 5: Selection of Advertisements and Questions

An individual who is being treated for lung cancer wishes to monitor treatment progress on a weekly basis using a portable device. The portable device is powered by and controlled by a mobile phone. An application on the phone is used to run the diagnostic assay. The individual creates a user profile in the application that includes a medical diagnosis, treatment regimen, and demographic information. The user profile is uploaded to a remote server storing a plurality of user profiles. A first software module at the server analyzes the user profile and compares it against a population of ads configured by advertisers to determine one or more ads suitable for display. The first software module selects an ad for an action movie based on the user age and gender falling within an advertiser preference for males aged between 18 and 35 for the ad. A second software module analyzes the user profile and compares it against a population of questions to determine one or more questions suitable for presenting to the individual. The second software module selects a set of three questions asking about the individual's taste in movies based on the individual's answer to a question during a previous test that he is interested in movies. The selection of ads and questions are provided by the remote server to the application of the device. The individual loads a sample into the portable device. While the assay is being carried out by the device, the user interface of the application presents a choice of answering the selected questions or watching the selected advertisement. The individual selects the advertisement, which is then displayed as a movie teaser on a display of the mobile phone. The individual then selects the movie teaser, which opens a link to a website containing a full length movie trailer. The individual's decision to select the movie teaser is added to the person's user profile on the remote server. When the assay is complete, the individual is given a result. The result is also transmitted to the individual's healthcare provider. The first and second software modules analyze the updated user profile and compare it against the population of ads and the population of questions to determine suitable ads and/or questions.

Example 6: Monitoring a Disease State in a Population

Portable devices for monitoring malaria infections are distributed throughout medical clinics in a third world country. Individuals who receive treatment at the clinics monitor their response to treatment using the portable devices, which upload geo-tagged and time-stamped analyte analysis results to an encrypted database. Epidemiologists at an infectious disease research institute are granted permission to access anonymized, HIPAA-compliant information in the database as authorized users. They analyze the geographic distribution of the results over time to determine that the malaria infection rate in an eastern geographic region has increased substantially over the past 6 months. The epidemiologists contact a non-governmental organization involved in combating malaria and provide this information. The non-governmental organization then deploys personnel and resources to the eastern geographic region to deliver additional mosquito netting and repellent as well as anti-malarial medication. The epidemiologists continue monitoring the situation over the next 6 months and determine that the humanitarian efforts by the NGO have halted the increased malaria infection rate.

Example 7: Targeted Advertising to a Healthy Individual

An otherwise healthy individual without any disease diagnosis obtains a portable device to monitor her health. The individual generates a user profile using her digital processing device and authorizes access to her social media accounts on Facebook and Twitter to build her user profile. The individual also provides a detailed family health history including a history of breast cancer on her mother's side of the family. Based on this information, when she uses the portable device to conduct a test, she is presented with a targeted ad for early breast cancer screening.

Example 8: Treatment Recommendation in Association with Analyte Testing

Figure 6F:
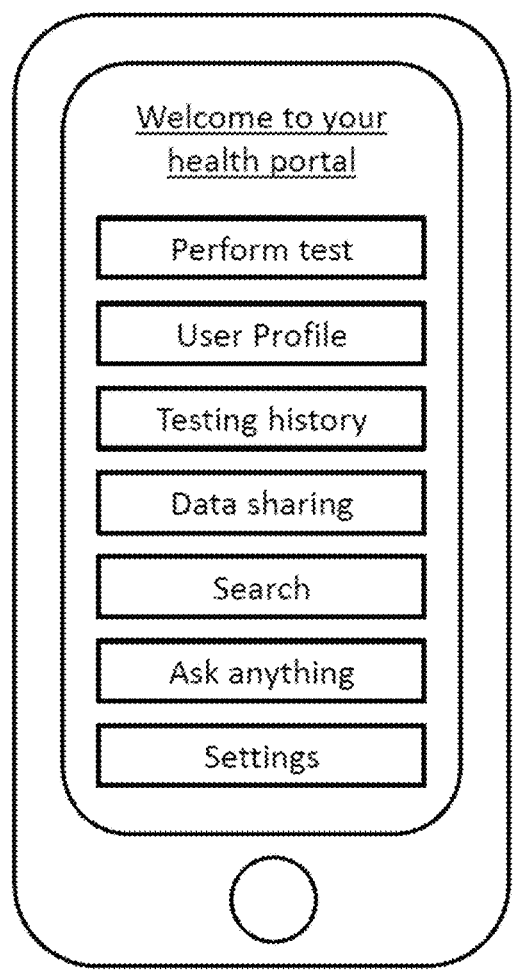
FIG. 6F illustrates an exemplary display of an electronic device showing a user portal.

An individual who is diabetic selects a portable device for periodically monitoring the blood plasma concentration of a medication he is taking. The selected portable device is an implantable medication monitor configured with a network element for communicating with the individual's smartphone. The monitor has been adapted to have minimal hardware and software components to minimize the resources needed for manufacture, and has been provided to the individual for free. As such, the monitor comprises a sensor and any hardware needed to conduct the testing, and the network element, but lacks a user interface (aside from a power switch), a display, or other conventional features present in diagnostic devices. After the individual implants the monitor and turns it on, the device automatically pairs with the individual's smartphone via the network element. An application on the phone communicates with the monitor and sends instructions to the monitor to conduct analyte testing according to a treatment regimen provided by the individual when setting up his profile on the user portal (FIG. 6F). The user profile is setup to include the medication, the disease or condition treated by the medication, treatment regimen, address, and demographic information.

Following profile setup, the individual selects the "perform test" option in the user portal on his smartphone. The phone sends instructions to the monitor to begin testing and presents the user with the option to pay for the testing, watch an advertisement, or answer a survey question in order to view the result (FIG. 6A). The individual selects the option to answer the survey question and is presented with a question targeted towards the medication he is monitoring (FIG. 6B). The individual selects "dizziness" as a side effect of the medication. After answering the question, the individual is given the ability to view his test results once the testing has been completed (FIG. 6C). The test results are then shown indicating that the user's current medication level is high. These test results are also uploaded to a remote server for further analysis and generation of one or more recommendations accompanying the test result. Since the treatment regimen is known, an algorithm analyzes the dosing frequency and dosage to calculate a dosage reduction for reducing the blood plasma concentration to normal levels. This recommendation is then transmitted to the individual's smartphone and presented on the phone's display (FIG. 6D). In addition, another algorithm has analyzed the outcome data for a matched cohort of subjects who also have taken the same medication for treating the same condition to generate a prediction of an adverse response requiring medical attention based upon similar blood plasma concentrations. Although the individual did not select any of the more serious symptoms requiring medical attention in answering the survey question, this algorithm determines that there is a moderate risk of adverse response and provides a warning to see a doctor in case the individual notices more serious symptoms (FIG. 6E).

About six hours later, the individual begins experiencing abdominal pain while traveling. Recalling the warning presented on his smartphone, he opens up the user portal on his phone and selects the "search" function (FIG. 6F). He uses the search function to identify a healthcare provider in proximity to his location. In response to his search query, an algorithm is executed on a remote server that filters healthcare providers for capability to deal with overdoses and symptoms related to the individual's medication. The algorithm then computes estimated times to treatment as the sums of estimated times to arrival to the healthcare provider locations and the estimated wait times using current traffic conditions and historical wait times for the providers. The providers are then listed in order of estimated time to treatment. The individual selects the provider, a nearby emergency room, with the shortest estimated time to treatment, and his phone opens up a map application with directions to the provider's location. The individual visits emergency room and receives treatment. During the visit, the individual selects the "Ask anything" function on his phone's application portal and requests to communicate with his doctor who prescribed the medication. The portal lists options to send a text message, email, audio message, or video message. The individual chooses to send a message to his doctor informing him of his condition. A few days later, while using the monitor to test himself, he is prompted with a survey question inquiring about whether he has suffered any adverse response due to the previous high blood plasma concentration of his medication. The individual answers that he has had to visit the hospital for treatment due to abdominal pain. This information is then anonymized, and uploaded onto an encrypted database in a remote server.

What is claimed is:

1. A computer-implemented system for performing a biological assay, comprising:
   a) a mobile computing device comprising: at least one processor, a memory, a display, a camera, and an operating system configured to perform executable instructions;
   b) an analyte analysis apparatus configured to reversibly accept and position the mobile computing device and an analyte analysis cartridge such that the camera of the mobile computing device is positioned to capture an image of a result field of the analyte analysis cartridge, said analyte analysis cartridge being configured to receive and process a biological material of an individual; and
   c) a computer program stored in the memory of the mobile computing device, the computer program including instructions executable by the at least one processor to create an application comprising:
      i) a software module controlling the analyte analysis apparatus to carry out the biological assay by performing analyte testing of the biological material using the analyte analysis cartridge, wherein said analyte testing generates an optical signal based on an analyte in the biological sample, and controlling the camera to capture the image of the optical signal in the result field;
      ii) a software module performing data analysis on the image to generate a result, wherein the data analysis comprises performing image processing on pixel image data;
      iii) a software module presenting the result on the display of the mobile computing device; and
      iv) a software module selecting one or more ads from a population of ads or one or more questions from a population of questions to present during at least one of the analyte testing or the data analysis before presenting the result, wherein the result is locked until the one or more ads have been presented or the one or more questions have been answered, wherein the one or more ads or one or more questions are targeted to the individual based on at least the biological assay and optionally in combination with one or more of a user profile of the individual, the analyte, a prior analyte testing result, or a location of the mobile computing device.

2. The system of claim 1, wherein the analyte analysis cartridge is a dielectrophoresis (DEP) cartridge.

3. The system of claim 1, wherein a response by the individual to the one or more ads or the one or more questions is added to the user profile of the individual.

4. The system of claim 1, wherein the software module selecting the one or more ads or the one or more questions receives instructions from a remote server for selection of the one or more ads from the population of ads or the one or more questions from the population of questions, wherein the selection is based on analysis performed by the remote server.

5. The system of claim 1, wherein the one or more ads or the one or more questions are provided by a third-party ad network.

6. The system of claim 1, wherein the application further comprises a software module providing an interface allowing upload of the result to an online database.

7. The system of claim 1, wherein the application further comprises a software module providing a query interface allowing search of an online database.

8. The system of claim 1, wherein the application further comprises a software module providing at least one of a treatment recommendation and a healthcare provider recommendation generated by a machine learning algorithm based on the user profile of the individual, the analyte, the result, the location of the mobile computing device, historical treatment outcome data for a cohort of patients matched to the individual, healthcare provider information, or a combination thereof.

9. The system of claim 1, wherein the result is geo-tagged with the location of the mobile computing device and uploaded to a database.

10. A computer-implemented method for performing a biological assay, comprising:
   a) communicating, by a mobile computing device, with an analyte analysis apparatus configured to reversibly accept and position the mobile computing device and an analyte analysis cartridge such that a camera of the mobile computing device is positioned to capture an image of a result field of the analyte analysis cartridge, said analyte analysis cartridge being configured to receive and process a biological material of an individual;
   b) transmitting, by the mobile computing device, a control signal to the analyte analysis apparatus to carry out the biological assay by performing analyte testing of the biological material of the individual using the analyte analysis cartridge, wherein said analyte testing generates an optical signal based on an analyte in the biological sample, and controlling the camera of the mobile computing device to capture the image of the optical signal in the result field;
   c) performing data analysis on the image to generate a result, wherein the data analysis comprises performing image processing on pixel image data;
   d) presenting, by the mobile computing device, the result on a display; and
   e) selecting, by the mobile computing device, one or more ads from a population of ads or one or more questions from a population of questions to present during at least one of the analyte testing or the data analysis before presenting the result, wherein the result is locked until the one or more ads have been presented or the one or more questions have been answered, wherein the one or more ads or one or more questions are targeted to the individual based on at least the biological assay and optionally in combination with one or more of a user profile of the individual, the analyte, a prior analyte testing result, or a location of the mobile computing device.

11. The method of claim 10, wherein the mobile computing device or the analyte analysis apparatus provides power to the analyte analysis cartridge.

12. The method of claim 11, wherein the analyte analysis cartridge is a dielectrophoresis (DEP) cartridge.

13. The method of claim 10, wherein the mobile computing device receives instructions from a remote server for selection of the one or more ads from the population of ads or the one or more questions from the population of questions, wherein the selection is based on analysis performed by the remote server.

14. The method of claim 10, further comprising providing at least one of a treatment recommendation and a healthcare provider recommendation generated by a machine learning algorithm based on the user profile of the individual, the analyte, the result, the location of the mobile computing device, historical treatment outcome data for a cohort of patients matched to the individual, healthcare provider information, or a combination thereof.

15. The method of claim 10, wherein the result is geo-tagged with the location of the mobile computing device and uploaded to a database.

16. Non-transitory computer readable storage media encoded with a program including instructions executable by at least one processor of a mobile computing device to create an application for performing a biological assay, said application comprising:
- a) a software module communicating with an analyte analysis apparatus configured to reversibly accept and position the mobile computing device and an analyte analysis cartridge such that a camera of the mobile computing device is positioned to capture an image of a result field of the analyte analysis cartridge, said analyte analysis cartridge being configured to receive and process a biological material of an individual;
- b) a software module transmitting a control signal to an analyte analysis apparatus to carry out the biological assay by performing analyte testing of the biological material of the individual using the analyte analysis cartridge, wherein said analyte testing generates an optical signal based on an analyte in the biological sample, and controlling the camera to capture the image of the optical signal in the result field of the analyte analysis cartridge;
- c) a software module performing data analysis on the image to generate a result, wherein the data analysis comprises performing image processing on pixel image data;
- d) a software module presenting the result on a display of the mobile computing device; and
- e) a software module selecting one or more ads from a population of ads or one or more questions from a population of questions to present during at least one of the analyte testing or the data analysis before presenting the result, wherein the result is locked until the one or more ads have been presented or the one or more questions have been answered, wherein the one or more ads or one or more questions are targeted to the individual based on at least the biological assay and optionally in combination with one or more of a user profile of the individual, the analyte, a prior analyte testing result, or a location of the mobile computing device.

17. The media of claim 16, wherein the application further comprises a software module providing at least one of a treatment recommendation and a healthcare provider recommendation generated by a machine learning algorithm based on the user profile of the individual, the analyte, the result, the location of the mobile computing device, historical treatment outcome data for a cohort of patients matched to the individual, healthcare provider information, or a combination thereof.

18. The media of claim 16, wherein the result is geo-tagged with the location of the mobile computing device.

19. A computer-implemented system for performing a biological assay, comprising:
- a) a mobile computing device comprising: at least one processor, a memory, a display, a camera, and an operating system configured to perform executable instructions;
- b) an analyte analysis apparatus configured to reversibly accept and position the mobile computing device and an analyte analysis cartridge such that the camera of the mobile computing device is positioned to capture an image of a result field of the analyte analysis cartridge, said analyte analysis cartridge being configured to receive and process a biological material of an individual; and
- c) a computer program stored in the memory of the mobile computing device, the computer program including instructions executable by the at least one processor to create an application comprising:
  - i) a software module controlling the analyte analysis apparatus to carry out the biological assay by performing analyte testing of the biological material using the analyte analysis cartridge, wherein said analyte testing generates an optical signal based on an analyte in the biological sample, and controlling the camera to capture the image of the optical signal in the result field;
  - ii) a software module performing data analysis on the image to generate a result, wherein the data analysis comprises performing image processing on pixel image data;
  - iii) a software module presenting the result on the display of the mobile computing device; and
  - iv) a software module selecting one or more ads from a population of ads or one or more questions from a population of questions to present during at least one of the analyte testing or the data analysis before presenting the result, wherein the result is locked until the one or more ads have been presented or the one or more questions have been answered, wherein the one or more ads or one or more questions are targeted to the individual based on user information comprising a user profile of the individual, the analyte, a prior analyte testing result, a location of the mobile computing device, or a combination thereof, wherein the user information is updated based on at least the result of the analyte testing.

* * * * *